United States Patent
Scholz et al.

(10) Patent No.: US 9,826,770 B2
(45) Date of Patent: Nov. 28, 2017

(54) ANTIMICROBIAL COMPOSITIONS COMPRISING ESTERS OF HYDROXYCARBOXYLIC ACIDS

(75) Inventors: Matthew T. Scholz, Woodbury, MN (US); Danli Wang, Shoreview, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1646 days.

(21) Appl. No.: 11/908,244

(22) PCT Filed: Mar. 10, 2006

(86) PCT No.: PCT/US2006/009008
§ 371 (c)(1),
(2), (4) Date: Jun. 9, 2008

(87) PCT Pub. No.: WO2006/099358
PCT Pub. Date: Sep. 21, 2006

(65) Prior Publication Data
US 2008/0287538 A1    Nov. 20, 2008

Related U.S. Application Data

(60) Provisional application No. 60/660,594, filed on Mar. 10, 2005.

(51) Int. Cl.
*A61K 31/22* (2006.01)
*A01N 37/00* (2006.01)
(Continued)

(52) U.S. Cl.
CPC ............ *A23L 3/3517* (2013.01); *A61K 31/22* (2013.01); *A61K 31/25* (2013.01); *A61L 2/0088* (2013.01); *A61L 2/18* (2013.01)

(58) Field of Classification Search
CPC .. A61K 31/506; A61K 9/0053; A61K 9/2013; A61K 9/2027; A61K 9/2031; A61K 9/4858; A61K 9/4866
See application file for complete search history.

(56) References Cited

U.S. PATENT DOCUMENTS 2,818,390 A    12/1957    Beaver et al.
3,048,266 A    8/1962    Hackhel et al.
(Continued)

FOREIGN PATENT DOCUMENTS

AU    16317/95    11/1995
AU    2000 49587    12/2000
(Continued)

OTHER PUBLICATIONS

Van Putten, P.L.; "Mandelic acid and urinary tract infections"; Antonie van Leeuwenhoek, International Journal of General and Molecular Microbiology 1979 NL; vol. 45, No. 4, 1979 pp. 622.
(Continued)

*Primary Examiner* — Savitha Rao

(57) ABSTRACT

Antimicrobial compositions, especially those useful when applied topically, particularly to mucosal tissues (i.e., mucous membranes), including, in particular, a fatty alcohol ester of a hydroxycarboxylic acid, alkoxylated derivatives thereof, or combinations thereof. The compositions can also include an enhancer component, a surfactant component, a hydrophobic component, and/or a hydrophilic component. Such compositions provide effective topical antimicrobial activity and are accordingly useful in the treatment and/or prevention of conditions that are caused, or aggravated by, microorganisms (including viruses).

10 Claims, 1 Drawing Sheet

(51) Int. Cl.
*A01N 37/06* (2006.01)
*A01P 1/00* (2006.01)
*A61K 31/25* (2006.01)
*A61P 31/00* (2006.01)
*A23L 3/3517* (2006.01)
*A61L 2/00* (2006.01)
*A61L 2/18* (2006.01)

(56) References Cited

U.S. PATENT DOCUMENTS

| | | | |
|---|---|---|---|
| 3,489,148 A | 1/1970 | Duncan et al. ............... 128/284 |
| 3,806,615 A | 4/1974 | Frankenfeld et al. |
| 3,983,214 A | 9/1976 | Misato et al. |
| 3,985,903 A | 10/1976 | Hasegawa |
| 4,002,775 A | 1/1977 | Kabara |
| 4,010,252 A | 3/1977 | Hewitt |
| 4,067,997 A | 1/1978 | Kabara |
| 4,113,854 A | 9/1978 | Andrews et al. |
| 4,160,820 A | 7/1979 | Wagenknecht |
| 4,189,481 A | 2/1980 | Kabara |
| 4,252,834 A | 2/1981 | Inamine et al. |
| 4,284,653 A | 8/1981 | Shigeoka et al. |
| 4,299,852 A | 11/1981 | Ueno et al. |
| 4,338,342 A | 7/1982 | Tan et al. |
| 4,364,929 A | 12/1982 | Sasmor |
| 4,485,029 A | 11/1984 | Kato et al. |
| 4,512,987 A | 4/1985 | Schindlery et al. |
| 4,557,935 A | 12/1985 | af Ekenstam et al. |
| 4,597,975 A | 7/1986 | Woodward et al. |
| 4,599,233 A | 7/1986 | Misato et al. |
| 4,648,876 A | 3/1987 | Becker et al. |
| 4,722,941 A | 2/1988 | Eckert et al. |
| 4,724,149 A | 2/1988 | Gul et al. |
| 4,840,738 A | 6/1989 | Hardy et al. |
| 4,894,220 A | 1/1990 | Nabi et al. |
| 4,931,282 A | 6/1990 | Asmus et al. |
| 4,962,093 A | 10/1990 | Ohkawa et al. |
| 4,963,555 A | 10/1990 | Jones et al. |
| 4,980,163 A | 12/1990 | Blackburn et al. |
| 4,983,394 A | 1/1991 | Hussein et al. |
| 4,983,595 A | 1/1991 | Benjamin et al. |
| 4,985,242 A | 1/1991 | Sekine et al. |
| 4,997,851 A | 3/1991 | Isaacs et al. |
| 5,017,617 A | 5/1991 | Kihara et al. |
| 5,084,096 A | 1/1992 | Stovicek |
| 5,093,140 A | 3/1992 | Watanabe |
| 5,098,694 A | 3/1992 | Komp et al. |
| 5,135,910 A | 8/1992 | Blackburn et al. |
| 5,145,685 A | 9/1992 | Carmody |
| 5,188,822 A | 2/1993 | Viccaro et al. |
| 5,192,802 A | 3/1993 | Rencher |
| 5,208,257 A | 5/1993 | Kabara |
| 5,217,950 A | 6/1993 | Blackburn et al. |
| 5,219,887 A | 6/1993 | Andrews et al. |
| 5,225,473 A | 7/1993 | Duan |
| 5,231,087 A | 7/1993 | Thornfeldt |
| 5,234,719 A | 8/1993 | Richter et al. |
| 5,260,271 A | 11/1993 | Blackburn et al. |
| 5,270,188 A | 12/1993 | Yamaguchi et al. |
| 5,304,540 A | 4/1994 | Blackburn et al. |
| 5,314,915 A | 5/1994 | Rencher |
| 5,318,955 A | 6/1994 | Mueller et al. |
| 5,320,772 A | 6/1994 | Tricca |
| 5,326,567 A | 7/1994 | Capelli |
| 5,334,582 A | 8/1994 | Blackburn et al. |
| 5,346,724 A | 9/1994 | Ohgake et al. |
| 5,362,555 A | 11/1994 | Lal |
| 5,364,650 A | 11/1994 | Guthery |
| 5,378,731 A | 1/1995 | Andrews et al. |
| 5,380,756 A | 1/1995 | Andrews et al. |
| 5,389,374 A | 2/1995 | Brown-Skrobot |
| 5,408,022 A | 4/1995 | Imazato et al. |
| 5,429,819 A | 7/1995 | Oka et al. |
| 5,434,182 A | 7/1995 | Isaacs et al. |
| 5,460,802 A | 10/1995 | Asami et al. |
| 5,460,833 A | 10/1995 | Andrews et al. |
| 5,462,749 A | 10/1995 | Rencher |
| 5,466,685 A | 11/1995 | Brown-Skrobot et al. |
| 5,482,931 A | 1/1996 | Harris et al. |
| 5,490,992 A | 2/1996 | Andrews et al. |
| 5,516,510 A | 5/1996 | Beilfuss |
| 5,516,536 A | 5/1996 | Mikkelsen et al. |
| 5,547,677 A | 8/1996 | Wright |
| 5,549,901 A | 8/1996 | Wright |
| 5,550,145 A | 8/1996 | Olund et al. |
| 5,569,461 A | 10/1996 | Andrews |
| 5,629,019 A | 5/1997 | Lee et al. |
| 5,656,591 A | 8/1997 | Tomita |
| 5,660,842 A | 8/1997 | Petschow |
| 5,665,776 A | 9/1997 | Yu et al. |
| 5,705,182 A | 1/1998 | Brown-Skrobot |
| 5,708,023 A | 1/1998 | Modak |
| 5,728,756 A | 3/1998 | Gaffar et al. |
| 5,736,178 A | 4/1998 | Cook et al. |
| 5,736,574 A | 4/1998 | Burnier et al. |
| 5,747,069 A | 5/1998 | Asakura et al. |
| 5,753,252 A | 5/1998 | Brown-Skrobot |
| 5,759,584 A | 6/1998 | Traupe et al. |
| 5,762,948 A | 6/1998 | Blackburn |
| 5,804,549 A | 9/1998 | Blackburn et al. |
| 5,817,325 A | 10/1998 | Sawan et al. |
| 5,862,949 A | 1/1999 | Markey et al. |
| 5,906,814 A | 5/1999 | Epstein |
| 5,945,110 A | 8/1999 | Vianen et al. |
| 5,951,993 A | 9/1999 | Scholz et al. |
| 5,955,502 A | 9/1999 | Hansen et al. |
| 5,965,088 A | 10/1999 | Lever et al. |
| 5,965,610 A | 10/1999 | Modak |
| 5,968,539 A | 10/1999 | Beerse et al. |
| 6,008,261 A | 12/1999 | Genova et al. ............... 516/58 |
| 6,022,551 A | 2/2000 | Jampani |
| 6,033,705 A | 3/2000 | Isaacs |
| 6,045,254 A | 4/2000 | Inbar et al. |
| 6,054,139 A | 4/2000 | Lambert et al. |
| 6,054,143 A | 4/2000 | Jones |
| 6,057,274 A | 5/2000 | Bator |
| 6,071,866 A | 6/2000 | Fujiwara et al. |
| 6,089,389 A | 7/2000 | Sharon et al. |
| 6,090,075 A | 7/2000 | House |
| 6,093,417 A | 7/2000 | Petrus |
| 6,094,414 A | 7/2000 | Taira et al. |
| 6,106,851 A | 8/2000 | Beerse et al. |
| 6,110,516 A | 8/2000 | Hoover et al. |
| 6,110,908 A | 8/2000 | Guthery |
| 6,113,933 A | 9/2000 | Beerse et al. |
| 6,121,327 A | 9/2000 | Tsuzuki et al. |
| 6,121,329 A | 9/2000 | Fujii et al. |
| 6,123,933 A | 9/2000 | Hayama et al. |
| 6,165,494 A | 12/2000 | Picciano |
| 6,171,611 B1 | 1/2001 | Picciano |
| 6,177,071 B1 | 1/2001 | Lin et al. |
| 6,183,757 B1 | 2/2001 | Beerse et al. |
| 6,183,763 B1 | 2/2001 | Beerse et al. |
| 6,187,327 B1 | 2/2001 | Stack |
| 6,187,332 B1 | 2/2001 | Gern et al. |
| 6,190,674 B1 | 2/2001 | Beerse et al. |
| 6,190,675 B1 | 2/2001 | Beerse et al. |
| 6,197,315 B1 | 3/2001 | Beerse et al. |
| 6,210,695 B1 | 4/2001 | Beerse et al. |
| 6,211,243 B1 | 4/2001 | Johnson |
| 6,214,866 B1 | 4/2001 | Drogemoller et al. |
| 6,217,877 B1 | 4/2001 | Weidner |
| 6,224,898 B1 | 5/2001 | Balogh et al. |
| 6,228,383 B1 | 5/2001 | Hansen et al. |
| 6,238,682 B1 | 5/2001 | Klofta et al. |
| 6,258,368 B1 | 7/2001 | Beerse et al. |
| 6,278,008 B1 | 8/2001 | Endo et al. |
| 6,287,577 B1 | 9/2001 | Beerse et al. |
| 6,294,186 B1 | 9/2001 | Beerse et al. |
| 6,319,895 B1 | 11/2001 | Tomita et al. |
| 6,352,727 B1 | 3/2002 | Takahashi |
| 6,375,984 B1 | 4/2002 | Kim |
| 6,383,523 B1 | 5/2002 | Murad |
| 6,403,069 B1 | 6/2002 | Chopra |

(56) References Cited

U.S. PATENT DOCUMENTS

| | | | |
|---|---|---|---|
| 6,414,023 B1 | 7/2002 | Brandsborg |
| 6,436,430 B1 | 8/2002 | Mulye |
| 6,440,405 B1 | 8/2002 | Cooper et al. |
| 6,468,521 B1 | 10/2002 | Pedersen et al. |
| 6,494,856 B1 | 12/2002 | Zygmont |
| 6,500,861 B1 | 12/2002 | Wider |
| 6,506,873 B1 | 1/2003 | Ryan et al. |
| 6,534,075 B1 | 3/2003 | Hei et al. |
| 6,548,552 B1 | 4/2003 | Deresiewicz et al. |
| 6,555,566 B2 | 4/2003 | Ponikau |
| 6,559,189 B2 | 5/2003 | Baker, Jr. et al. |
| 6,579,906 B2 | 6/2003 | Cooper et al. |
| 6,590,051 B1 | 7/2003 | Carter et al. |
| 6,596,763 B1 | 7/2003 | Thormar et al. |
| 6,635,676 B2 | 10/2003 | Baker et al. |
| 6,746,635 B2 | 6/2004 | Mathoiwitz et al. |
| 6,846,846 B2 | 1/2005 | Modak et al. |
| 6,943,197 B2 | 9/2005 | Maibach et al. |
| 6,951,642 B2 | 10/2005 | Scholz et al. |
| 7,030,203 B2 | 4/2006 | Mosbey et al. |
| 7,569,530 B1 | 8/2009 | Pan |
| 7,678,389 B1 | 3/2010 | Cordray |
| 7,858,662 B2 | 12/2010 | Chang |
| 2002/0013305 A1 | 1/2002 | Hanna |
| 2002/0025344 A1 | 2/2002 | Newman et al. |
| 2002/0031556 A1 | 3/2002 | Lindahl |
| 2002/0037268 A1 | 3/2002 | Stack |
| 2002/0058010 A1 | 5/2002 | Picard-Lesboueyries |
| 2002/0086039 A1 | 7/2002 | Lee et al. |
| 2002/0193417 A1 | 12/2002 | Seidel et al. |
| 2003/0147925 A1 | 8/2003 | Sawan |
| 2003/0152644 A1* | 8/2003 | Modak et al. ............ 424/667 |
| 2003/0194447 A1 | 10/2003 | Scholz et al. |
| 2003/0228376 A1 | 12/2003 | Mody et al. |
| 2003/0235626 A1 | 12/2003 | Maibach et al. |
| 2004/0009130 A1 | 1/2004 | Detore et al. ............ 424/59 |
| 2004/0052834 A1 | 3/2004 | West |
| 2004/0091428 A1 | 5/2004 | Libin |
| 2004/0126414 A1 | 7/2004 | Michaelis |
| 2004/0186183 A1 | 9/2004 | Johnson |
| 2004/0247685 A1 | 12/2004 | Modak et al. |
| 2004/0253139 A1 | 12/2004 | Denton ............ 422/28 |
| 2004/0265345 A1 | 12/2004 | Perricone |
| 2005/0019355 A1 | 1/2005 | Denton ............ 425/401 |
| 2005/0020678 A1* | 1/2005 | Denton ............ 514/546 |
| 2005/0053593 A1 | 3/2005 | Wang |
| 2005/0058673 A1 | 3/2005 | Scholz et al. |
| 2005/0084471 A1 | 4/2005 | Andrews et al. |
| 2005/0089539 A1 | 4/2005 | Scholz et al. |
| 2005/0112188 A1 | 5/2005 | Eliaz et al. |
| 2005/0118124 A1* | 6/2005 | Reinhart et al. ............ 424/63 |
| 2006/0029569 A1 | 2/2006 | Scholz et al. |
| 2006/0034798 A1 | 2/2006 | Mosbey et al. |
| 2006/0051384 A1 | 3/2006 | Scholz et al. |
| 2006/0051385 A1 | 3/2006 | Scholz |
| 2006/0052452 A1 | 3/2006 | Scholz |
| 2006/0099237 A1 | 5/2006 | Modak et al. |
| 2006/0205838 A1 | 9/2006 | Velamakanni |
| 2006/0275349 A1 | 12/2006 | Andrews |
| 2006/0276541 A1 | 12/2006 | Tautvydas et al. |
| 2007/0020029 A1 | 1/2007 | Baumann et al. |
| 2008/0142023 A1 | 6/2008 | Schmid |
| 2009/0005339 A1 | 1/2009 | Scholz |
| 2009/0186943 A1 | 7/2009 | Ikeda et al. |
| 2009/0226541 A1 | 9/2009 | Scholz |
| 2010/0022654 A1 | 1/2010 | Asmus et al. |

FOREIGN PATENT DOCUMENTS

| | | |
|---|---|---|
| CH | 634 749 | 2/1983 |
| DE | 43 02 812 | 8/1994 |
| DE | 43 19 546 | 12/1994 |
| DE | 196 42 127 | 4/1998 |
| DE | 10156794 | 6/2003 |
| DE | 101 61 885 | 7/2003 |
| DE | 10 2004 034691 | 2/2005 |
| EP | 0 104 346 | 4/1984 |
| EP | 0 131 393 | 1/1985 |
| EP | 0 156 563 | 10/1985 |
| EP | 0 172 724 | 2/1986 |
| EP | 0 191 217 | 8/1986 |
| EP | 0 243 145 | 10/1987 |
| EP | 0 244 144 | 11/1987 |
| EP | 0 245 928 | 11/1987 |
| EP | 0 253 535 | 1/1988 |
| EP | 0 272 149 | 6/1988 |
| EP | 0 375 827 A2 | 3/1989 |
| EP | 0 312 519 | 4/1989 |
| EP | 0 455 370 | 11/1991 |
| EP | 0 465 423 | 1/1992 |
| EP | 0 483 835 | 5/1992 |
| EP | 0 489 967 | 6/1992 |
| EP | 0 497 607 | 8/1992 |
| EP | 0 530 861 | 3/1993 |
| EP | 0 547 727 | 6/1993 |
| EP | 0 567 704 | 11/1993 |
| EP | 0 608 433 | 8/1994 |
| EP | 0 629 347 | 12/1994 |
| EP | 0 876 768 | 11/1998 |
| EP | 0 937 812 | 8/1999 |
| EP | 1 157 685 | 11/2001 |
| EP | 1 449 909 | 8/2004 |
| ES | 2 095 183 | 1/1997 |
| FR | 2 729 050 | 7/1996 |
| GB | 2 053 195 | 2/1981 |
| GB | 2 193 892 | 2/1988 |
| GB | 2 323 784 | 10/1989 |
| GB | 2 338 649 | 12/1999 |
| JP | 72022252 | 9/1968 |
| JP | 51-15669 | 2/1976 |
| JP | 51-139645 | 2/1976 |
| JP | 76-84022 | 9/1976 |
| JP | 51106731 | 9/1976 |
| JP | 52-07428 | 1/1977 |
| JP | 52003859 | 1/1977 |
| JP | 77-22781 | 2/1977 |
| JP | 52-33181 | 8/1977 |
| JP | 77-73621 | 9/1977 |
| JP | 53 066415 | 6/1978 |
| JP | 53-091126 | 8/1978 |
| JP | 79032058 | 10/1979 |
| JP | 56-43211 | 4/1981 |
| JP | 83018050 | 11/1981 |
| JP | 57176903 | 10/1982 |
| JP | Sho 59-163477 | 9/1984 |
| JP | 60-44539 | 3/1985 |
| JP | 85043111 | 9/1985 |
| JP | 61-152269 | 10/1986 |
| JP | 62-48612 | 3/1987 |
| JP | 63-130541 | 6/1988 |
| JP | 63-166837 | 7/1988 |
| JP | 1-256343 | 10/1989 |
| JP | 2-46255 | 2/1990 |
| JP | 02-116302 | 5/1990 |
| JP | 3067573 | 3/1991 |
| JP | 4016173 | 1/1992 |
| JP | 4018003 | 1/1992 |
| JP | 05 229915 | 9/1993 |
| JP | 05-320067 | 12/1993 |
| JP | 6022730 | 1/1994 |
| JP | 07-039356 | 2/1995 |
| JP | 8-40861 | 2/1996 |
| JP | 08-056631 | 3/1996 |
| JP | 8099878 | 4/1996 |
| JP | 8099887 | 4/1996 |
| JP | 08-151326 | 6/1996 |
| JP | 08-175989 | 7/1996 |
| JP | 8-187070 | 7/1996 |
| JP | 8205771 | 8/1996 |
| JP | 9067593 | 3/1997 |
| JP | 10508337 | 8/1998 |
| JP | 11113780 | 4/1999 |
| JP | Hei 11-113779 | 4/1999 |
| JP | 11302462 | 11/1999 |

(56) References Cited

FOREIGN PATENT DOCUMENTS

| | | |
|---|---|---|
| JP | 11-349418 | 12/1999 |
| JP | 3040282 | 5/2000 |
| JP | 2000-295976 | 10/2000 |
| JP | 2001 226205 | 8/2001 |
| JP | 2001 323298 | 11/2001 |
| JP | 2002-145736 | 5/2002 |
| JP | 2002-255711 | 9/2002 |
| JP | Kokai 2001-53564 | 9/2002 |
| JP | 2002-322090 | 11/2002 |
| KR | 9105620 | 8/1991 |
| WO | WO 82/03173 | 9/1982 |
| WO | WO 89/02754 | 4/1989 |
| WO | WO 89/12399 | 12/1989 |
| WO | WO 92/21320 | 12/1992 |
| WO | WO 93/15018 | 8/1993 |
| WO | WO 93/20812 | 10/1993 |
| WO | WO 93/21906 | 11/1993 |
| WO | WO 94/18943 | 9/1994 |
| WO | WO 94/27440 | 12/1994 |
| WO | WO 95/07616 | 3/1995 |
| WO | WO 95/24179 | 9/1995 |
| WO | WO 95-26134 | 10/1995 |
| WO | WO 95/31956 | 11/1995 |
| WO | WO 96/02228 | 2/1996 |
| WO | WO 96/25469 | 8/1996 |
| WO | WO 96/29867 | 10/1996 |
| WO | WO 97/00076 | 1/1997 |
| WO | WO 97/00163 | 1/1997 |
| WO | WO 97/11912 | 4/1997 |
| WO | WO 97/16168 | 5/1997 |
| WO | WO 97/23577 | 7/1997 |
| WO | WO 97/25032 | 7/1997 |
| WO | WO 98/09520 | 3/1998 |
| WO | WO 98/14189 | 4/1998 |
| WO | WO 99/11237 | 3/1999 |
| WO | WO 99/22703 | 5/1999 |
| WO | WO 99/37172 | 7/1999 |
| WO | WO 99/44444 | 9/1999 |
| WO | WO 99/59538 | 11/1999 |
| WO | WO 99/60998 | 12/1999 |
| WO | WO 99/66793 | 12/1999 |
| WO | WO 00/01351 | 1/2000 | |
| WO | WO 00/03612 | 1/2000 | ............... A23L 3/00 |
| WO | WO 00/04118 | 1/2000 |
| WO | WO 00/69267 | 11/2000 |
| WO | WO 00/71183 | 11/2000 |
| WO | WO 00/71789 | 11/2000 |
| WO | WO 00/78141 | 12/2000 |
| WO | WO 01/12155 | 2/2001 |
| WO | WO 01/24839 | 4/2001 |
| WO | WO 01/28552 | 4/2001 | ............ A61K 31/195 |
| WO | WO 01/43549 | 6/2001 |
| WO | WO 02/26261 | 4/2002 |
| WO | WO 02/47637 | 6/2002 |
| WO | WO 02/089849 | 11/2002 |
| WO | WO 02/100244 | 12/2002 |
| WO | WO 02/102244 A1 | 12/2002 |
| WO | WO 03/022211 | 3/2003 |
| WO | WO 03/028767 | 4/2003 |
| WO | WO 03-032948 | 4/2003 |
| WO | WO 03/037293 | 5/2003 |
| WO | WO 03/047636 | 6/2003 |
| WO | WO 2004/032927 | 4/2004 |
| WO | WO 04-052308 | 6/2004 |
| WO | WO 2004/062643 | 7/2004 |
| WO | WO 2005-02482 | 1/2005 |
| WO | WO2005/009353 | 3/2005 |
| WO | WO 2005/022998 | 3/2005 |
| WO | WO 2005/023233 | 3/2005 |
| WO | WO 2005/102287 | 11/2005 |
| WO | WO2006/026876 | 3/2006 | ............ C07C 69/675 |
| WO | WO2006/029351 | 3/2006 | ............. A01N 59/00 |
| WO | WO 2007-094332 | 8/2007 |
| WO | WO 2008-057773 | 5/2008 |

OTHER PUBLICATIONS

Abda: Rezepturhinweise: Triclosan in Dermatika NRF—Neues Rezeptur Formularium pp. 1-4 XP002391034, (Apr. 16, 2004).

Ahvenainen, "New approaches in improving the shelf life of minimally processed fruit and vegetables," *Trends in Food Science & Technology*, vol. 7, pp. 179-187 (Jun. 1996).

Baker et al., "Antimicrobial Properties of Lauricidin in Mechanically Deboned Chicken, Minced Fish and Chicken Sausage" *J. of Food Safety*, vol. 4, pp. 177-184 (1982).

Bell et al., "The Efficacy of Nisin, Sorbic Acid and Monolaurin as Perservatives in Pasteurized Cured Meat Products" *Food Microbiology*, vol. 4, pp. 277-283 (1987).

Block, S., "Acid-Anionic Surfactant Sanitizers", Disinfection, Sterilization and Preservation, Chapter 16, Lea & Febiger, Philidelphia PA, pp. 319-323 (1977).

Boddie, R.L., "Evaluation of postmilking teat germicides containing Lauricidin, saturated fatty acids and lactic acid", *Stn Caplus*, vol. 6, No. 117, XP002030991 (1992).

Branen, J.K., et al., "Enhancement of nisin, lysozyme, and monolaurin antimicrobial activities by ethylenediaminetetraacetic acid and lactoferrin", *Intl Journal of Food & Microbiology*, vol. 90, No. 1, pp. 63-74 XP002316393 (Jan. 1, 2004).

Chavigny, K.H., "The Use of polymixin B as a urethral lubricant to reduce the post-instrumental incidence of bacteiuria in females", *Int. J. Nurs. Stud.*, vol. 12, pp. 33-42, (1975).

Federal Register, 21 CFR Parts 333 and 369, Tentative Final Monograph for Healthcare Antiseptic Drug Products; Proposed Rule (1994).

Flournoy, et al., "The Role of Lauricidin as an Antimicrobil Agent" *Drugs of Today*, vol. 21 No. 8, pp. 373-377 (1985).

Gillespie, W.A., et al., "Prevention of Catheter Infection of Urine in Female Patients", *British Medical Journal*, pp. 13-16 (1962).

Gloor, M., et al., "Triclosan, ein dermatologishes Lokaltherapeutikum" Hautarzt, vol. 53, pp. 724-729, XP002391035, (Nov. 2002).

Hall et al., "Spice Extracts, Lauricidin, and Propylene Glycol as Inhibitors of Clostridium Botulinum in Turkey Frankfurter Slurries", *Poultry Science*, vol. 65, No. 6, pp. 1167-1171 (1986).

Hill, R.L. and M.W. Casewell, "The in-vitro activity of povidone-iodine cream against *Staphylococus aureas* and its bioavailability in nasal secretions", *Journal of Hospital Infection*, vol. 45, pp. 198-205 (2000).

Izat et al., "The Use of Propylene Glycol and/or Lactic Acid in Chill Water for Reducing Salmoneallae on Broilers" *J. of Food Processing and Preservation*, vol. 14, pp. 369-374 (1990).

Kabara, J.J., et al. "Antimicrobial Lipids: Natural and Synthetic Fatty Acids and Monoglycerides", *Lipids*, Champaign, IL, vol. 12, No. 9, pp. 753-759 XP000563038 (Sep. 1, 1977).

Kabara, "GRAS Antimicrobial Agents for Cosmetic Products", *J. Soc. Cosmet. Chem.* vol. 31, pp. 1-10 (1980).

Kabara, "Food-Grade Chemicals for Use in Designing Food Preservative Systems", *J. of Food Protection*, vol. 44, pp. 633-647 (1981).

Kabara, A New Preservative System for Food, *J. of Food Safety*, vol. 4, pp. 13-25 (1982).

Kabara, "Medium-Chain Fatty Acids and Esters as Antimicrobial Agents" *Cosmetic and Drug Preservation*, vol. 16, pp. 275-304 (1984).

Kato et al., "Combined Effect on Different Drugs on the Antibacterial Activity of Fatty Acids and their Esters", vol. 4, pp. 355-363 (1975).

Kato, et al., "Combined Effect of Citric and Polyphosphoric Acid on the Antibacterial Activity of Monoglycerides", vol. 4, No. 6 pp. 254-261 (1976).

Kiser, K. et al., "Development and Characterization of *Staphylococcus aureus* Nasal Colonization Model in Mice," *Infect and Immunity*, vol. 67, No. 10, pp. 5001-5006 (1999).

Kostiala, A.A.I., et al., "Effect of nitrofurantoin and methenamine hippurate prophylaxis on bacteria and yeasts in the urine of patients with an indwelling catheter", *J. of Hospital Infection*, vol. 3, pp. 347-364 (1982).

(56) References Cited

OTHER PUBLICATIONS

MacFarlane, D.E., "Prevention and treatment of catheter-associated urinary tract invections", *J. of Infection*, vol. 10, pp. 96-106 (1985).
May, et al., "Time-kill studies of tea tree oils on clinical isolates", *J. of Antimicrobial Chemotherapy*, vol. 45, pp. 639-643 (2000).
Mead et al., "Food-Related Illness and Death in the United States", *Emerg. Infect. Dis.*, vol. 5, No. 5, pp. 607-625 (1999).
Merianos, "Chapter 13, Quaternary Ammonium Antimicrobial Compounds," in Disinfection, Sterilization, and Preservation, 4th Ed., Block, Ed., Philadelphia, PA, Title page, Publication page, and Chapter 13 (pp. 225-255), (1991).
Morgan, D. M., "Urinary tract infection in hospitalized patients", *Canadian Hospital*, pp. 27-30 (1973).
Nakagaki, et al., "Solubility & Hydrolysis Rate of I-Monolaurin in Aqueous Solutions", *Yakugaku Zasshi*, vol. 90, No. 10, pp. 1310-1315 (1970).
Nicoletti, G. et al., The Antimicrobial Activity in vitro of chlorhexidine, a mixture of isothiazolinones (Kathon CG) and cetyl trimethyl ammonium bromide (CTAB), *Journal of Hospital Infection*, vol. 23, pp. 87-111 (1993).
Oh, et al., "Enhanced Inhibition of Listeria monocytogenes by Glycerol Monolaurate with Organic Acids", *Journal of Food Science*, vol. 59, No. 6, pp. 1258-1261 (1994).
Perez-Roth, E. et al. "Mupirocin resistance in methicillin-resistant *Staphylococcus aureus* clinical isolates in a Spanish hospital. Co-application of multiplex PCR assay and conventional microbiology methods", *Diag. Micro. Infect. Dis.*, vol. 43, pp. 123-128 (2002).
Perl, T. et al., "New Approaches to Reduce *Staphylococcus aureua* Nosocomial Infection Rates: Treating *S. aureus* Nasal Carriage", *Ann. Pharmacother.*, vol. 32, pp. S7-S16 (1998).
Physician's Desk Reference, definition of the composition of Aquaphor, p. 685, Edition (1993).
Product Information Brochure, Sensive SC 50 a multifunctional additive, Schuelke & Mayer (16 pgs.) (Nov. 2006).
Projan, et al., "Glycerol Monolaurate Inhibits the Production of β-Lactamase, Toxic Shock Syndrom Toxin-1, and Other Staphylococal Exoproteins by Interfering with Signal Transduction" *Journal of Bacteriology*, vol. 176, No. 14, pp. 4204-4209 (Jul. 1994).
Remington's Pharmaceutical Services, definition of absorption base, 14th Ed., p. 1600 (1970).
Rice, J. "Organic acid sprays," *Food Processing*, pp. 45, 47-48, 50 (Apr. 1994).
Sawhney, A.S. et al., "Bioerodible Hydrogels Based on Photopolymerized Poly(ethylene glycol)-co-poly(a-hydroxy acid) Diacrylate Macromers", *Macromolecules*, vol. 26, pp. 581-587 (1993).
Schemmel et al., "Monolaurin as an Anticaries Agent", Chapter 4, *Symposium on the Pharmacological Effect of Lipds*, pp. 37-43 (1983).
Sciarra and Cutie, "Aersols," *Chapter 92 in Remington's Pharmaceutical Sciences*, 18th edition, pp. 1694-1712 (1990).
Silverman, Chapter 44 in *Disinfection, Sterilization, and Preservation*, First addition, C. A. Lawrence and S.S. Block (1968).
Stecker, Ph.D., "Chapter 14, The Salicylanilides and Carbanilides," in Disinfection, Sterilization, and Preservation, 2nd Ed., Block, Ed., Philadelphia, PA, Title page, Publication page, and Chapter 14 (pp. 282-300) (1977).
Vadehra et al., "Comparison of Antibacterial Properties of Lauricidin® and BHA against Antibotic Resistant and Sensitive Strains of *Staphylococcus aureus* and *Pseudomonos aeruginosa*" *AOCS Monograph* vol. 13, No. 2, pp. 77-87, XP000560207 (1985).
Venkitanarayanan et al., "Inactivation of *Escherichia coli* 0157:H7 by combinations of GRAS chemicals and temperature", *Food Microbiology*, vol. 16, pp. 75-82 (1999).
Vorum, H. et al., "Solubility of Long-Chain Fatty Acids in Phosphate Buffer at pH 7.4," *Biochimica et. Biophysica Acta*, vol. 1126, pp. 135-142 (1992).
Wakabayashi, et al., Increased *Staphylococcus*-killing Activity of an Antimicrobial Peptide, Lactoferricin B, with Minocycline and Monoacylglyserol, *Bioscience Biotechnology and Biochemistry* vol. 66, No. 10, pp. 2161-2167 (Oct. 2002).
Wang et al., "Inhibition of *Listeria monocytogenes* by Monoacylglycerols Synthesized from Coconut Oil and Milkfat by Lipase-Catalzed Glycerolysis" *J. of Agric. Food Chem.*, vol. 41, pp. 1000-1005 (1993).
Watanabe, H. et al., "Low Concentrations of Mupirocin in the Pharynx following Intranasal Application May Conrtibute to Mupirocin Resistance in Methicillin-Resistant *Staphylococcus aureus*," *J. Clin. Micro.*, vol. 39, No. 10 pp. 3775-3777 (2001).
Whitley, et al., "Herpes zoster: focus on treatment in older adults", *Antiviral Research* vol. 44, pp. 145-154 (1999).
Williams, J.D., et al., "Trials of Five Antibacterial Creams in the Control of Nasal Carriage of *Staphylococcus aureus*", *The Lancet*, vol. 290, Issue 7512, pp. 390-392 (Aug. 1967).
Williamson et al., "A New Method for the Quantitative Investigation of Cutaneous Bacteria," *J. Invest. Derm.*, vol. 45, pp. 498-503 (1965).
Wooley, "EDTA-tris Potentiation of Antimicrobial Agents", *Modern Veterinary Practice*, pp. 113-116 (1983).
Gokalp Iscan et al.; "Antimicrobial Screening of *Mentha piperita* Essential Oils"; Journal of Agricultural and Food Chemistry; vol. 50; No. 14; pp. 3943-3946; 2002.
Rutala, W. et al.; "Susceptibility of Antibiotic-Susceptible ad Antibiotic-Resistant Hospital Bacteria to Disinfectants"; Infection Control and Hospital Epidemiology; vol. 18, No. 6, pp. 417-421; Jun. 1997.
Database Medline—US National Library of Medicine (NLM) Jul. 1992, Kida N. etal. "Effect of pH on preferential antibacterial-activity of ethylenediaminetetraacetic acid (EDTA)" XP002400661 Database accession No. NLM1433911.
Mannose may be useful for treating uterine infections [retrieved from the internet on Nov. 18, 2008]; URL http://www.equinescienceupdate.co.uk/mannos.htm.
NutritionalTest.com, 10105 E via Linda #103-192, Scottsdale, AZ 85258. Take the guess work out of taking nutrients, D. Mannose [retrieved from the internet on Nov. 18, 2008], URL <http://www.nutritionaltest.com/dmannos.html>.
Mosges R., et al.; "The role of the respiratory mucosa in the infectious process" Respiratory mucosa: the core of infection and inflammation; Title page, Editorial page, pp. 1-32, Product Information page and Publication Page (36 pgs total) 1998 (Servier, Paris).
Merck Manual of Diagnosis and Therapy, Seventeenth Edition; Published 1999 by Marck Research Laboratories, pp. 673-677.
Merriam-Webster's Collegiate Dictionary, published 1998 by Merriam-Webster, Incorporated; p. 924.
Physician's Desk Reference to Pharmaceutical Specialties and Biologicals; 26th Edition, 1972; Publisher Charles E. Baker; p. 628.
Keresteci, A.G. et al.; "Indwelling catheter infection"; Canadian Medical Association Journal; vol. 109; Oct. 20, 1973; pp. 711-713.
"Disodium EDTA" datasheet [online]. Cosmeticsinfo 2013 © Retrieved from the Internet:<URL:http://cosmeticsinfo.org/ingredient/disodium-edta>; 2 pgs.
"Versene™ Chelating Agents for Personal Care Formulations" Dow® Chemical Company datasheet. Form 113-015041107AMS. Nov. 2007. 8 pgs.
Lanigan et al., "Final Report on the safety assessment of EDTA, calcium disodium EDTA, diammonium EDTA, dipotassium EDTA, disodium EDTA, TEA-EDTA, tetrasodium EDTA, tripotassium EDTA, trisodium EDTA, HEDTA, and trisodium HEDTA," *Int J. Toxicol*, Abstract Only, Oct. 2002; Suppl 2: pp. 95-142.
Elliott et al.; "Bladder Irrigation or Irritation?" British Journal of Urology, 1989; 64:391-394.
Schneeberger et al.; "A randomized study on the effect of bladder irrigation with povidone-iodine before removal of an indwelling catheter" J. of Hospital Infection, 1992; 21:223-229.
Van Den Broek et al.; "Bladder Irrigation with Povidone-Iodine in Prevention of Urinary-Tract Infections associated with Intermittent Urethral Catheterisation"; The Lancet; Mar. 9, 1985; 563-565.

(56) References Cited

OTHER PUBLICATIONS

Berkow, The Merck Manual of Diagnosis and Therapy, 16th Edition, May 1, 1995, vol. 3, pp. 2228-2231.
Morizono, Safety of Antimicrobials Applied in the Middle Ear Cavity, Aurinasal Clinic, Practica. Oto.rhino.laryngologica. Suppl., 2002, vol. 95, No. 7, pp. 663-669.
Osborne, "Skin Penetration Enhancers, cited in Technical literature", Pharmaceutical Technology, Nov. 1997, pp. 58-66.
Schlievert, "Effect of glycerol monolaurate on bacterial growth and toxin production", Antimicrobial Agents Chemotherapy, Mar. 1992, vol. 36, No. 3, pp. 626-631.
Tanaka, "Antibacterial Compounds From Nutmeg Against Upper Airway Respiratory Tract Bacteris", ITE Letters on Batteries, New Technologies and Medicine, 2000, vol. 1, No. 3, pp. 412-417.
Venkitanarayanan, "Inactivation of *Escherichia coli* 0157:H7 by combinations of GRAS chemicals and temperature", Food Microbiology, 1999, vol. 16, pp. 75-82.
Wright,, "Middle Ear Effects of Ototopical Agents", Ototoxicity, 107-113 (2004).

\* cited by examiner

ANTIMICROBIAL COMPOSITIONS COMPRISING ESTERS OF HYDROXYCARBOXYLIC ACIDS

CROSS REFERENCE TO RELATED APPLICATIONS

This application is a national stage filing under 35 U.S.C. 371 of PCT/US2006/009008 filed Mar. 10, 2006, which claims the benefit of U.S. Provisional Application No. 60/660,594, filed Mar. 10, 2005, the disclosure of which is incorporated by reference in its entirety herein.

BACKGROUND

The use of antimicrobial agents plays an important part in current medical therapy. This is particularly true in the fields of dermatology as well as skin and wound antisepsis, where the most effective course of treatment for skin or mucous membranes (e.g., as in the nasal cavities and in particular the anterior nares, vaginal tissue, oral tissue, urethra, etc.), which are afflicted with bacterial, fungal, or viral infections or lesions, frequently includes the use of a topical antimicrobial agent. For decades medicine has relied primarily upon antibiotics to fight systemic as well as topical infections. For example, bacitracin, neomycin sulfate, polymyxin B sulfate, gentamicin, framycetin-gramicidin, lysostaphin, methicillin, rifampin, tobramycin, nystatin, mupirocin, and combinations thereof, as well as many others, have been used with varying success.

Antibiotics are generally effective at very low levels and are often safe with very few, if any, side effects. Often antibiotics have little or no toxicity to mammalian cells. Thus, they may not retard, and can even enhance, wound healing. Antibiotics are generally of a narrow spectrum of antimicrobial activity. Furthermore, they often act on very specific sites in cell membranes or on very specific metabolic pathways. This can tend to make it relatively easy for bacteria to develop resistance to the antibiotic(s) (i.e., the genetically acquired ability to tolerate much higher concentrations of antibiotic) either through natural selection, transmission of plasmids encoding resistance, mutation, or by other means.

For example, there are multiple reports of resistance to mupirocin when used as a treatment for impetigo as well as a nasal decolonizing agent. Resistance rates have been reported as high as 25% and even as high as 50% (see, for example, E. Perez-Roth et al., *Diag. Micro. Infect. Dis.*, 43:123-128 (2002) and H. Watanabe et al., *J. Clin. Micro.*, 39(10): 3775-3777 (2001)). Even though presurgical decolonization of the anterior nares using mupirocin has been shown to decrease the risk of surgical site infection by as much as 2 to 10 times (T. Perl et al., *Ann. Pharmacother.*, 32:S7-S16 (1998)), the high resistance rates to this antibiotic make it unsuitable for routine use. Not only does resistance eliminate the ability of a medication to treat an affliction, but it can also put the patient at further risk, especially if the antibiotic is one that is routinely used systemically.

Antiseptics, on the other hand, tend to have broader spectrum of antimicrobial activity and often act by nonspecific means such as disruption of cell membranes, oxidation of cellular components, denaturation of proteins, etc. This nonspecific activity makes it difficult for resistance to develop to antiseptics. For example, there are very few reports of true resistance to antiseptics such as iodine, lower alcohols (ethanol, propanol, etc.), chlorhexidine, quaternary amine surfactants, chlorinated phenols, and the like. These compounds, however, need to be used at concentrations that often result in irritation or tissue damage, especially if applied repeatedly. Furthermore, unlike antibiotics, many antiseptics are not active in the presence of high levels of organic compounds. For example, formulations containing iodine or quaternary ammonium compounds have been reported to be inactivated by the presence of organic matter such as that in nasal, wound, or vaginal secretions, and perhaps even on skin.

Many antiseptic compounds are viewed as irritants. For example, compositions containing iodine and/or chlorhexidine have been reported to cause skin irritation. Mucosal tissues, such as the anterior nares, nasal, vaginal, oral, aural, and esophageal cavities, which can have a high level of microbial colonization in certain otherwise healthy individuals, as well as individuals with infectious diseases such as chronic sinusitis, may be particularly sensitive to irritation. Additionally, due to the irritating nature many of these compounds may be unsuitable for application to irritated or infected dermal tissue to treat skin conditions, such as lesions from impetigo and shingles.

Also, for certain applications, especially in the nose and mouth, it is particularly desirable for the compositions to have little or no color, little or no odor, and an acceptable taste. Lack of color is also important for many topical indications. This is not the case for many antiseptics such as iodine and iodophors, which have an orange to brown color and a definite odor.

Some conventional antimicrobial compositions have used various carboxylic acids or fatty acids for the suppression of fungi, bacteria, molds, and the like. These compositions vary widely in their efficacy, stability, and levels of persistence. Plus, they possess an even wider variety of side effects. For example, many of these materials are viewed as irritants, particularly the C8-C12 fatty acids. This is particularly true for sensitive mucosal tissues, such as the anterior nares and nasal cavities, which can have a generally high level of microbial colonization in certain otherwise healthy individuals, as well as individuals with infectious diseases such as chronic sinusitis. Additionally, due to the irritating nature many of these agents would be unsuitable for application to irritated or infected dermal tissue such as lesions from impetigo and shingles or sensitive tissues such as the nasal cavities and especially the anterior nares.

Also, many conventional antimicrobial compositions are too low in viscosity and/or too hydrophilic in nature to maintain sufficient substantivity and persistence to provide sufficient antimicrobial activity on moist tissue, such as the anterior nares or open, exuding, or infected lesions, and the like.

Thus, there is still a need for additional antimicrobial compositions.

SUMMARY OF THE INVENTION

The present invention provides antimicrobial compositions and methods of using and making the compositions.

Such compositions are typically useful when applied topically, particularly to skin and mucosal tissues (i.e., mucous membranes), although a wide variety of surfaces can be treated. These compositions may also be particularly useful for antimicrobial food treatments including treatments on meat (beef, poultry, pork, lamb, etc.) as well as fruits, vegetables, seeds, plants, plant parts and/or any other food. They may also be suitable as preservatives for cosmetics, pharmaceuticals and foods. The compositions may also find utility in producing antimicrobial surfaces including making antimicrobial articles as well as antimicrobial treatments for hard surfaces in commercial and residential buildings. Surfaces that can be treated with the compositions include textiles, glass, polymeric surfaces, metal, wood, and rubber. These compositions may also find utility in dental applications including antimicrobial treatments of the oral cavity (e.g., antimicrobial toothpaste, floss, etc.) as well as in curable compositions such as tooth restoratives and impression materials. They can provide effective reduction, prevention, or elimination of microbes, particularly bacteria, fungi, and viruses. Preferably, the microbes are of a relatively wide variety such that the compositions of the present invention have a broad spectrum of activity.

Compositions of the present invention provide effective topical antimicrobial activity and are accordingly useful in the local treatment and/or prevention of conditions that are caused, or aggravated by, microorganisms (including viruses, bacteria, fungi, mycoplasma, and protozoa) on various hard and soft mammalian tissues, particularly teeth, skin, wounds, and/or mucous membranes.

Significantly, certain embodiments of the present invention have a very low potential for generating microbial resistance. Thus, such compositions can be applied multiple times over one or more days to treat topical infections or to eradicate unwanted bacteria (such as nasal colonization of *Staphylococcus aureus*). Furthermore, compositions of the present invention can be used for multiple treatment regimens on the same patient without the fear of generating antimicrobial resistance. This can be particularly important for chronically ill patients who are in need of decolonization of the anterior nares before hemodialysis, for example, or for antiseptic treatment of chronic wounds such as diabetic foot ulcers.

Also, preferred compositions of the present invention have a generally low irritation level for skin, skin lesions, and mucosal membranes (including the anterior nares, nasal cavities, and nasopharangyl cavity). Also, certain preferred compositions of the present invention are substantive for relatively long periods of time to ensure adequate efficacy.

Compositions of the present invention include an antimicrobial component that includes a fatty alcohol ester of a hydroxyacid, alkoxylated derivatives thereof, or combinations thereof. Preferred compositions include an effective amount of an antimicrobial component (typically, an antimicrobial lipid component) comprising a (C7-C14) saturated fatty alcohol ester (preferably a monoester) of a (C2-C8)hydroxycarboxylic acid, a (C8-C22)mono- or poly-unsaturated fatty alcohol ester (preferably a monoester) of a (C2-C8)hydroxycarboxylic acid, an alkoxylated derivative of either of the foregoing, or combinations thereof, wherein the alkoxylated derivative has less than 5 moles of alkoxide per mole of hydroxycarboxylic acid.

Optionally, certain compositions further include an enhancer component. Preferably, the composition comprises an effective amount of an enhancer component that includes an alpha-hydroxy acid, a beta-hydroxy acid, a chelating agent, a (C1-C4)alkyl carboxylic acid, a (C6-C12)aryl carboxylic acid, a (C6-C12)aralkyl carboxylic acid, a (C6-C12) alkaryl carboxylic acid, a phenolic compound, a (C1-C10) alkyl alcohol, an ether glycol, or combinations thereof. In certain embodiments, the compositions do not include parabens or phenoxyethanol.

Other components that can optionally be included as well are surfactants, hydrophilic components, and hydrophobic components. Compositions with hydrophobic components are typically used on mammalian tissues (particularly, skin, mucosal tissue, wounds) and medical devices that come in contact with such surfaces, whereas compositions with hydrophilic components are typically used on these surfaces as well as other hard surfaces (e.g., floor tiles).

Preferably, in certain compositions, water is present in less than 10 percent by weight (wt-%). Preferably, certain compositions are anhydrous.

Importantly, the compositions of the present invention are capable of destroying microorganisms on or in mammalian tissue. Therefore, the concentrations employed when used in most antimicrobial applications are generally greater than those that have been used to simply preserve certain topically applied compositions, i.e., prevent the growth of microorganism in topical compositions for purposes other than antisepsis. Depending on the application, many of these compounds at these concentrations can be irritating if delivered in simple aqueous or certain hydrophilic vehicle formulations. Many of the compositions of the present invention incorporate a substantial amount of a lipophilic or hydrophobic phase. The lipophilic phase is comprised of one or more water insoluble components. If delivered in a lipophilic phase, the irritation can be significantly reduced. The incorporation of the lipophilic phase may significantly reduce the irritation potential of the present compositions. Preferred lipophilic phase components have a solubility in water of less than 0.5% by weight and often less than 0.1% by weight. In addition, for situations where rapid kill is desired the antiseptic is preferably present at a concentration approaching or preferably exceeding the solubility limit of the lipophilic phase.

Importantly, the compositions also have sufficient viscosity to prevent inhalation into the lungs if used in the nose for applications such as nasal decolonization or treatment of other microbially caused or aggravated conditions such as sinusitis. The relatively high viscosity of the preferred compositions of the present invention also reduces migration that can be associated with other compositions, thus reducing irritation and mess. Despite the presence of the hydrophobic phase, compositions of the present invention exhibit very effective and rapid antimicrobial activity.

In addition, antimicrobial compositions that include hydrophilic components such as polyols (e.g., glycerin and polyethylene glycols) that themselves have little or no antimicrobial activity can considerably enhance the antimicrobial activity of the compositions.

Preferably, the antimicrobial component is present in an amount of at least 0.1 wt-%. Unless otherwise specified, all weight percents are based on the total weight of a "ready to use" or "as used" composition.

Preferably, the antimicrobial component includes lauryl lactate, lauryl lactyl lactate, 2 ethylhexyl lactate, 2 ethylhexyl lactyl lactate, capryl lactate, capryl glycolate, caprylyl lactate, caprylyl glycolate, capryl alcohol ester of 2 hydroxybenzoate, lauryl salicylate, capryl salicylate, and or combinations thereof.

Preferably, the surfactant includes a sulfonate surfactant, a sulfate surfactant, a phosphonate surfactant, a phosphate surfactant, a poloxamer surfactant, a cationic surfactant, or mixtures thereof.

Preferably, the hydrophilic component includes a glycol, a lower alcohol ether, a short chain ester, and combinations thereof, wherein the hydrophilic component is soluble in water in an amount of at least 20 wt-% at 23° C.

The present invention provides various methods of use. For example, the present invention provides a method of preventing and/or treating an affliction caused, or aggravated by, a microbial organism on mammalian tissue. Another example includes a method of decolonizing at least a portion of the nasal cavities, anterior nares, and/or nasopharynx of a subject of microorganisms. Another example includes a method of treating a wound or lesion.

In other embodiments, the present invention provides methods for killing or inactivating microorganisms. Herein, to "kill or inactivate" means to render the microorganism ineffective by killing them (e.g., bacteria and fungi) or otherwise rendering them inactive (e.g., bacteria and viruses). The present invention provides methods for killing bacteria such as *Staphylococcus* spp., *Streptococcus* spp., *Escherichia* spp., *Enterococcus* spp., *Pseudamonas* spp., *Gardnerella* sp., *Haemophilus* sp., *Corynebacterium* sp. bacteria, *Candida* sp. fungi, and combinations thereof, and more particularly *Staphylococcus aureus* (including antibiotic resistant strains such as methicillin resistant *Staphylococcus aureus*), *Staphylococcus epidermidis*, *Escherichia coli* (*E. coli*), *Pseudomonas aeruginosa* (*Pseudomonas ae.*), *Streptococcus pyogenes*, *Candida albicans*, and combinations thereof which often are on or in the skin or mucosal tissue of a subject. The method includes contacting the microorganism with an antimicrobial composition of the present invention in an amount effective to kill one or more microorganisms (e.g., bacteria and fungi) or inactivate one or more microorganisms (e.g., viruses, particularly herpes virus).

Definitions

The following terms are used herein according to the following definitions.

"Effective amount" means the amount of the antimicrobial component and/or the enhancer component when in a composition, as a whole, provides an antimicrobial (including, for example, antiviral, antibacterial, or antifungal) activity that reduces, prevents, or eliminates one or more species of microbes such that an acceptable level of the microbe results. Typically, this is a microbe level that is low enough not to cause clinical symptoms, and is desirably a non-detectable level (with respect to the microbes). It should be understood that in the compositions of the present invention, the concentrations or amounts of the components, when considered separately, may not kill to an acceptable level, or may not kill as broad a spectrum of undesired microorganisms, or may not kill as fast; however, when used together such components provide an enhanced (preferably synergistic) antimicrobial activity (as compared to the same components used alone under the same conditions).

It should be understood that (unless otherwise specified) the listed concentrations of all components are for "ready to use" or "as used" compositions. The compositions can be in a concentrated form. That is, certain embodiments of the compositions can be in the form of concentrates that would be diluted by the user with an appropriate vehicle.

"Hydrophilic" refers to a material that will dissolve or disperse in water (or other aqueous solution as specified) at a temperature of 23° C. in an amount of at least 7% by weight, preferably at least 10% by weight, more preferably at least 20% by weight, even more preferably at least 25% by weight, even more preferably at least 30% by weight, and most preferably at least 40% by weight, based on the total weight of the hydrophilic material and the water. The component is considered soluble (i.e., dissolved) if after thoroughly mixing the compound with water at 60° C. for at least 4 hours and allowing this to cool to 23-25° C. for 24 hours, and then again mixing the composition thoroughly it appears as a uniform clear solution without visible cloudiness, phase separation, or precipitate in a jar having a path length of 4 cm. Typically, when placed in 1×1 cm cell, the sample containing a hydrophilic material exhibits greater than, or equal to, 70% transmission measured in a suitable spectrophotometer at a wavelength of 655 nm. This dissolution test is done at the concentration of interest, e.g., at 7-40% by weight. Water dispersible hydrophilic materials disperse in water to form uniform cloudy dispersions after vigorous shaking of a 5% by weight mixture of the hydrophilic component in water above the melting point of the component followed by cooling to room temperature for 4 hours, or preferably placing in a Warning Blender half full for 3 minutes and allowing any foam to settle to form a uniform dispersion without visible phase separation (creaming or settling) after standing for 60 minutes. Preferred hydrophilic components are water-soluble. The hydrophilic component can be water.

"Hydrophobic" or "water-insoluble" refers to a material that will not significantly dissolve in water at 23° C. This means that less than 5% by weight, preferably less than 1% by weight, more preferably less than 0.5% by weight, and even more preferably less than 0.1% by weight, based on the total weight of the hydrophobic material and the water, will dissolve. Solubility can be determined by thoroughly mixing the compound with water at the appropriate concentration at 23° C. for at least 24 hours (or at elevated temperature if that is necessary to dissolve the compound), allowing this to sit at 23-25° C. for 24 hours, and observing the sample. In a glass jar with a 4-cm path length the sample should have evidence of a second phase, which can be liquid or solid and may be separated on the top, bottom, or distributed throughout the sample. For crystalline compounds care should be taken to avoid producing a supersaturated solution. The components should be mixed and observed. Cloudiness or presence of a visible precipitate or separate phase indicates that the solubility limit has been exceeded. Typically, when placed in 1×1 cm cell the composition containing the hydrophobic compound in water has less than 70% transmission measured in a suitable spectrophotometer at a wavelength of 655 nm. For solubility determinations less than that which can be observed with the naked eye the solubility is determined using radiolabeled compounds as described under "Conventional Solubility Estimations in Solubility of Long-Chain Fatty Acids in Phosphate Buffer at pH 7.4," Henrik Vorum, et al. in *Biochimica et. Biophysica Acta*, 1126, 135-142 (1992).

"Stable" means physically stable or chemically stable, which are both defined in greater detail below.

"Enhancer" means a component that enhances the effectiveness of the antimicrobial component such that when the composition less the antimicrobial component and the composition less the enhancer component are used separately, they do not provide the same level of antimicrobial activity as the composition as a whole. For example, an enhancer component in the absence of the antimicrobial component may not provide any appreciable antimicrobial activity. The enhancing effect can be with respect to the level of kill, the speed of kill, and/or the spectrum of microorganisms killed, and may not be seen for all microorganisms. In fact, an enhanced level of kill is most often seen in Gram negative bacteria such as *Escherichia coli*. An enhancer may be a synergist such that when combined with the remainder of the composition, the composition as a whole displays an activity that is greater than the sum of the activity of the composition less the enhancer component and the composition less the antimicrobial component.

"Microorganism" or "microbe" or "microorganism" refers to bacteria, yeast, mold, fungi, protozoa, mycoplasma, as well as viruses (including lipid enveloped RNA and DNA viruses).

"Antibiotic" means an organic chemical produced by microorganisms that has the ability in dilute concentrations to destroy or inhibit microorganisms and is used to treat infectious disease. This may also encompass semi-synthetic compounds that are chemical derivatives of the compound produced by microorganisms or synthetic compounds that act on very specific biochemical pathways necessary for the cell's survival.

"Antiseptic" means a chemical agent that kills pathogenic and non-pathogenic microorganisms. Preferred antiseptics exhibit at least a 2 log reduction of both *P. aeruginosa* and *S. aureus* in 60 minutes from an initial inoculum of $1-3\times10^7$ cfu/ml when tested in Mueller Hinton broth at 35° C. at a concentration of 0.25 wt-% in a Rate of Kill assay using an appropriate neutralizer as described in "The Antimicrobial Activity in vitro of chlorhexidine, a mixture of isothiazolinones (Kathon CG) and cetyl trimethyl ammonium bromide (CTAB)," G. Nicoletti et al., *Journal of Hospital Infection*, 23, 87-111 (1993). Antiseptics generally interfere more broadly with the cellular metabolism and/or the cell envelope. Antiseptics are sometimes referred to as disinfectants, especially when used to treat hard surfaces.

"Mucous membranes," "mucosal membranes," and "mucosal tissue" are used interchangeably and refer to the surfaces of the nasal (including anterior nares, nasoparangyl cavity, etc.), oral (e.g., mouth), outer ear, middle ear, vaginal cavities, and other similar tissues. Examples include mucosal membranes such as buccal, gingival, nasal, ocular, tracheal, bronchial, gastrointestinal, rectal, urethral, ureteral, vaginal (including the meatus and urethra), cervical, and uterine mucosal membranes "Antimicrobial lipid" means an antimicrobial compound having at least one alkyl or alkylene group having at least 6 carbon atoms, more preferably at least 7 carbon atoms, and even more preferably at least 8 carbon atoms, and preferably having a solubility in water of no greater than 1.0 gram per 100 grams (1.0 g/100 g) deionized water. Preferred antimicrobial lipids have a solubility in water of no greater than 0.5 g/100 g deionized water, more preferably, no greater than 0.25 g/100 g deionized water, and even more preferably, no greater than 0.10 g/100 g deionized water. Solubilities are determined using radio-labeled compounds as described under "Conventional Solubility Estimations" in Solubility of Long-Chain Fatty Acids in Phosphate Buffer at pH 7.4, Henrik Vorum et al., in *Biochimica et. Biophysica Acta.*, 1126, 135-142 (1992). Preferred antimicrobial lipids have a solubility in deionized water of at least 100 micrograms (µg) per 100 grams deionized water, more preferably, at least 500 µg/100 g deionized water, and even more preferably, at least 1000 µg/100 g deionized water. The antimicrobial lipids preferably have a hydrophile/lipophile balance (HLB) of at most 6.2, more preferably at most 5.8, and even more preferably at most 5.5. The antimicrobial lipids preferably have an HLB of at least 3, preferably at least 3.2, and even more preferably at least 3.4.

"Fatty" as used herein refers to a straight or branched chain alkyl or alkylene moiety having at least 6 (odd or even number) carbon atoms, unless otherwise specified.

"Affliction" means a condition to a body resulting from sickness, disease, injury, bacterial colonization, etc.

"Treat" or "treatment" means to improve the condition of a subject relative to the affliction, typically in terms of clinical symptoms of the condition.

"Decolonization" refers to a reduction in the number of microorganisms (e.g., bacteria and fungi) present in or on tissue that do not necessarily cause immediate clinical symptoms. Examples of decolonization include, but are not limited to, decolonization of the nasal cavity and wounds. Ordinarily, fewer microorganisms are present in colonized tissue than in infected tissue. When the tissue is completely decolonized the microorganisms have been "eradicated."

"Subject" and "patient" includes humans, sheep, horses, cattle, pigs, dogs, cats, rats, mice, or other mammal.

"Wound" refers to an injury to a subject which involves a break in the normal skin barrier exposing tissue below, which is caused by, for example, lacerations, surgery, burns, damage to underlying tissue such as pressure sores, poor circulation, and the like. Wounds are understood to include both acute and chronic wounds.

The terms "comprises" and variations thereof do not have a limiting meaning where these terms appear in the description and claims.

As used herein, "a," "an," "the," "at least one," and "one or more" are used interchangeably. The term "and/or" means one or all of the listed elements (e.g., preventing and/or treating an affliction means preventing, treating, or both treating and preventing further afflictions).

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

FIG. 1 (*a*) is a GC chromatogram for CERAPHYL 31.

FIG. 1(*b*) is a GC chromatogram for DERMOL ML.

FIG. 1(*c*) is a GC chromatogram for DERMOL OL

DETAILED DESCRIPTION OF ILLUSTRATIVE EMBODIMENTS

Figure 1A:
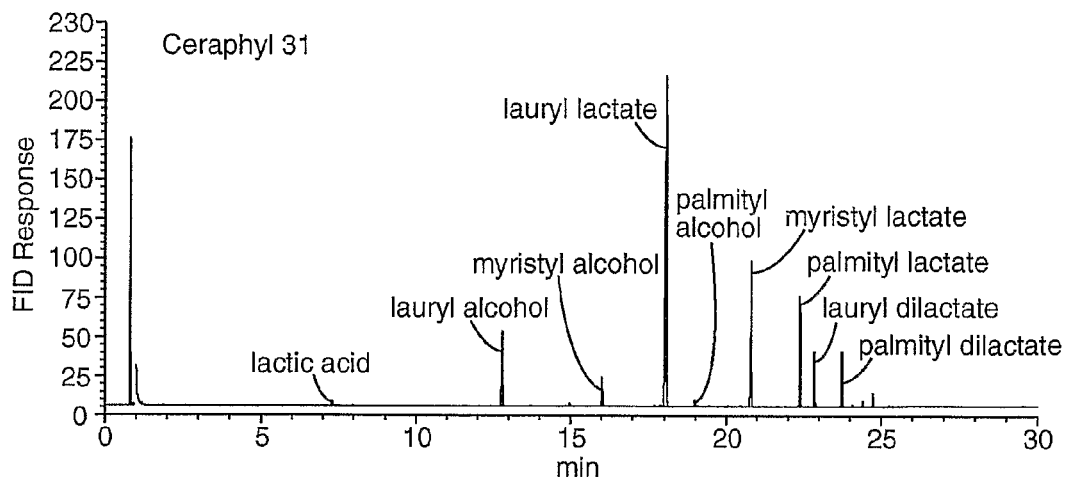
FIGS. 1*a*-*c* present GC purity chromatograms for antimicrobial lipids.

The present invention provides antimicrobial (including, e.g., antiviral, antibacterial, and antifungal) compositions. These compositions include one or more antimicrobial compounds selected from the group fatty alcohol esters of a hydroxyacid, alkoxylated derivatives thereof, or combinations thereof. In certain embodiments the compositions also include one or more enhancers. Certain compositions also include one or more surfactants, one or more hydrophilic compounds, and/or one or more hydrophobic compounds. In certain embodiments, compositions do not include any surfactants in addition to the antimicrobial components, which can function as surfactants.

Such compositions adhere well to bodily tissues (i.e., mammalian tissues such as skin, mucosal tissue, and wounds) and thus are very effective topically. Thus, the present invention provides a wide variety of uses of the compositions. Particularly preferred methods involve topical application, particularly to mucosal tissues (i.e., mucous membranes including the anterior nares and other tissues of the upper respiratory tract), aural, as well as skin (e.g., skin lesions) and wounds. Herein, such tissues are preferred examples of mammalian tissues. These compositions may be useful to treat a variety of veterinary conditions in a variety of mammalian animal species.

For certain applications in which limited antimicrobial activity is desired, compositions containing an antimicrobial component can be used, whereas in other applications in which more broad antimicrobial activity is desired, compositions containing both an antimicrobial component and an enhancer component are used. For example, in certain situations it may be desirable to kill or inactivate only one type or class of microorganism (e.g., Gram positive) as opposed to all the microorganisms present. In such situations, compositions of the present invention that contain an antimicrobial component without an enhancer component may be suitable.

Compositions of the present invention can be used to provide effective topical antimicrobial activity. For example, they can be used for hand disinfection, particularly in presurgical scrubs. They can be used to disinfect various body parts, particularly in patient presurgical skin antiseptics.

Compositions of the present invention can be used to provide effective topical antimicrobial activity and thereby treat and/or prevent a wide variety of afflictions. For example, they can be used in the treatment and/or prevention of afflictions that are caused, or aggravated by, microorganisms (e.g., Gram positive bacteria, Gram negative bacteria, fungi, protozoa, mycoplasma, yeast, viruses, and even lipid-enveloped viruses) on skin and/or mucous membranes, such as those in the nose (anterial nares, nasopharangyl cavity, nasal cavities, etc.), outer ear, and middle ear, mouth, rectum, vagina, or other similar tissues. Particularly relevant organisms that cause or aggravate such afflictions include *Staphylococcus* spp., *Streptococcus* spp., *Pseudomonas* spp., *Enterococcus* spp., and *Esherichia* spp., bacteria, as well as herpes virus, *Aspergillus* spp., *Fusarium* spp., and *Candida* spp. Particularly virulent organisms include *Staphylococcus aureus* (including resistant strains such as Methicillin Resistant *Staphylococcus Aureus* (MRSA)), *Staphylococcus epidermidis, Streptococcus pneumoniae, Enterococcus faecalis,* Vancomycin Resistant *Enterococcus* (VRE), *Pseudomonas auerginosa, Escherichia coli, Aspergillus niger, Aspergillus fumigatus, Aspergillus clavatus, Fusarium solani, Fusarium oxysporum, Fusarium chlamydosporum, Candida albicans, Streptococcus pneumoniae, Haemophilis influenza, Moraxella catarhalis, Candida glabrata,* and *Candida krusei.*

Compositions of the present invention can be used for the prevention and/or treatment of one or more microorganism-caused infections or other afflictions. In particular, compositions of the present invention can be used for preventing and/or treating one or more of the following: skin lesions, conditions of the skin such as impetigo, eczema, diaper rash in infants as well as incontinent adults, inflammation around ostomy devices, shingles, and bacterial infections in open wounds (e.g., cuts, scrapes, burns, lacerations, chronic wounds); necrotizing faciitis; infections of the outer ear; acute or chronic otitis media (middle ear infection) caused by bacterial, viral, or fungal contamination; fungal and bacterial infections of the vagina or rectum; vaginal yeast infections; bacterial rhinitis; ocular infections; cold sores; genital herpes; colonization by *Staphylococcus aureus* in the anterior nares (e.g., prior to surgery or hemodialysis); mucositis (i.e., inflammation as opposed to infection of a mucous membrane typically induced by non-invasive fungus); chronic sinusitis (e.g., that caused by bacterial or viral contamination); non-invasive fungus-induced rhinosinusitis; chronic colitis; Crohn's disease; burns; other acute and chronic wound infection and/or colonization; napkin rash; tinea pedis (i.e., athlete's foot); tinea curis (i.e., jock itch); tinea corporis (i.e., ringworm); candidiasis; strep throat, strep pharyngitis, and other Group A Streptococci infections; rosacea (often called adult acne); common cold; and respiratory afflictions (e.g., asthma). In sum, compositions of the present invention can be used for preventing and/or treating a wide variety of topical afflictions caused by microbial infection (e.g., yeast, viral, bacterial infections).

Compositions of the present invention can be used on a wide variety of surfaces. For example, they can be used on mammalian tissues (particularly, skin, mucosal tissue, chronic wounds, acute wounds, burns, and the like) and hard surfaces such as medical (e.g., surgical) devices, floor tiles, countertops, tubs, dishes, as well as on gloves (e.g., surgical gloves). They can also be impregnated into swabs, cloth, sponges, foams, nonwovens, and paper products (e.g., paper towels and wipes), for example. Typically, compositions with hydrophobic components are used on mammalian tissues (particularly, skin, mucosal tissue, wounds) and medical devices that come in contact with such surfaces, whereas compositions with hydrophilic components are used on these surfaces as well as other hard surfaces (e.g., floor tiles).

The compositions (or only the antimicrobial component) may also be incorporated into or onto various substrates. For example, the compositions can be incorporated into thermoplastic polymers and pressure sensitive adhesives. Suitable pressure sensitive adhesives include natural rubbers, synthetic rubbers, styrene block copolymers including but not limited to Styrene-Isoprene-Styrene (SIS), styrene-butadiene, styrene-isoprene and derivatives thereof such as those available from KRATON Polymers under the KRATON tradename, polyvinyl ethers, poly(meth)acrylates (including both acrylates and methacrylates), polyolefins such as poly-alpha olefins, silicones, and blends or mixtures thereof. Particularly preferred adhesive compositions are based on poly(meth)acrylates (including both acrylates and methacrylates). The polyacrylates may also comprise other vinylic non-acrylate monomers such as but not limited to N-vinyl lactams, (meth)acrylamides, styrene, methylvinyl ether, polystyrene macromers, vinyl acetate, and the like. Additionally, in certain embodiments of the present invention, fully hydrogenated adhesives may be preferred to prevent addition of iodine to any unsaturated functionalities present in the composition. These pressure sensitive adhesives may be hot-melt, solvent or water based coatings. Suitable thermoplastic polymers include polyolefins including polypropylene and polyethylene, polyurethanes, polyesters, polyacrylates, polycarbonate, and the like. For example, these may be used in a manner similar to the fatty acid esters disclosed in International Publication No. WO 00/71789. These compositions also may be coated onto various articles to provide antimicrobial surfaces. Suitable surfaces and coating methods are disclosed in International Publication No. WO 00/71183.

Thus, the present invention also provides various methods of use of compositions of the present invention. Various embodiments of the present invention include: a method of preventing an affliction caused, or aggravated by, a microorganism on mammalian tissue (particularly, skin and/or a mucous membrane); a method of decolonizing at least a portion of the nasal cavities, anterior nares, and/or nasopharynx of a subject of microorganisms; a method of treating a middle ear infection in a subject (through delivery directly to the middle ear, or indirectly via the Eustachian tube and/or the tympanic membrane); a method of treating chronic sinusitis in a subject (by treating at least a portion of the respiratory system, particularly the upper respiratory system, including the nasal cavities, anterior nares, and/or nasopharynx); a method of treating impetigo on the skin of a subject; a method of treating and/or preventing an infection on mammalian tissue (particularly, the skin, mucosal tissue, and/or wound) of a subject; a method of decontaminating skin around a transepidermal device such as a catheter, orthopedic pin, feeding tube, dialysis tube, and the like; a method of treating a burn; a method of killing or inactivating microorganisms (e.g., killing bacteria and/or fungi, or inactivating viruses); a method for providing residual antimicrobial efficacy (e.g., antibacterial, antifungal, and/or antiviral efficacy) that results from leaving a residue or imparting a condition on a surface (such as skin, mucosal tissue, wound, and/or medical device that contacts such surfaces) that remains effective and provides significant antimicrobial activity; a method of preventing and/or treating a subject for a common cold and/or respiratory affliction caused by a microbial infection; a method of decolonizing at least a portion of the throat/esophagus of a subject of microorganisms; and a method of decolonizing at least a portion of the oral cavity of a subject of microorganisms.

Various embodiments of the present invention also include: methods of decontaminating meat; methods of decontaminating fruit and/or seeds; methods of reducing spoilage in food products; methods of preserving cosmetics and pharmaceutical products; methods of decontaminating inanimate objects and surfaces; as well as methods of preventing microbial survival and/or growth on inanimate objects.

It should be understood that compositions of the present invention can be used in situations in which there are no clinical indications of an affliction. For example, compositions of the present invention can be used in methods of decolonizing at least a portion of the nasal cavities (i.e., space behind the vestibule of the nose), anterior nares (i.e., the opening in the nose to the nasal cavities, also referred to as the external nares), and/or nasopharynx (i.e., the portion of the pharynx, i.e., throat, that lies above the point of food entry into the pharynx) of a subject of microorganisms. A suitable model to test for the effectiveness of compositions to decolonize the anterior nares has been established and is described by K. Kiser et al., *Infect and Immunity,* 67(10), 5001-5006 (1999). Compositions of the present invention can also be used to decolonize microorganisms from wounds.

Decolonization methods using compositions of the present invention are particularly useful in immunocompromised patients (including oncology patients, diabetics, HIV patients, transplant patients an the like), particularly for fungi such as *Aspergillus* spp. and *Fusarium* spp.

In particular, compositions of the present invention can be used in chronic wounds to eliminate methicillin-resistant *Staphylococcus aureus*, which may or may not show clinical signs of infection such as inflammation, pus, exudate, etc. Also, it is of significance to note that certain compositions of the present invention can kill lipid-enveloped viruses, which can be very difficult to kill and can cause shingles (Herpes), chronic sinusitis, otitis media, and other local diseases.

Those of ordinary skill in the art will readily determine when a composition of the present invention provides antimicrobial activity using assay and bacterial screening methods well known in the art. One readily performed assay involves exposing selected known or readily available viable microorganism strains, such as *Enterococcus* spp., *Aspergillus* spp., *Escherichia* spp., *Staphylococcus* spp., *Streptococcus* spp., *Pseudomonas* spp., or *Salmonella* spp., to a test composition at a predetermined bacterial burden level in a culture media at an appropriate temperature. For the preferred compositions of the present invention this is most conveniently done by the Antimicrobial Kill Rate Test described in the Examples Section. Briefly, as described in the Antimicrobial Kill Rate Test, after a sufficient contact time, an aliquot of a sample containing the exposed bacteria is collected, diluted, and plated out on agar. The plated sample of bacteria is incubated for twenty-four to forty-eight hours and the number of viable bacterial colonies growing on the plate is counted. Once colonies have been counted the reduction in the number of bacteria caused by the test composition is readily determined. Bacterial reduction is generally reported as $\log_{10}$ reduction determined by the difference between the $\log_{10}$ of the initial inoculum count and the $\log_{10}$ of the inoculum count after exposure. Preferred compositions of the present invention have an average of at least a 2 log reduction and preferably at least 3 log reduction, and most preferably at least 4 log reduction in test bacteria (e.g., *S. aureus* (ATCC 33593)) in 10 minutes.

Some of the preferred compositions were tested as described in the Examples Section for antimicrobial activity against *S. aureus* (Gram positive, ATCC Number 33593) and *E. coli* (Gram negative, ATCC Number 11229). In general, the *E. coli* is more difficult to kill than MRSA. Preferred compositions of the present invention also exhibit very rapid antimicrobial activity. As shown in the Examples Section, preferred formulations are able to achieve an average log reduction of at least 1 log against these two organisms after a 10 minute exposure and preferably after a 5 minute exposure. More preferred compositions are able to achieve an average log reduction of at least 2 log and even more preferred at least 3 log against these three organisms after a 10 minute exposure and preferably after a 5 minute exposure.

For residual antimicrobial efficacy, compositions of the present invention preferably maintain an average log reduction of at least 1 log, more preferably at least 1.5 log, and even more preferably at least 2 log, for at least 0.5 hour, more preferably at least 1 hour, and even more preferably at least 3 hours after application to an affected site or after testing the composition on the forearm of a subject. To test this, a composition was applied to the forearm of a subject as a uniform wet coating in an amount of approximately 4 milligrams per square centimeter (mg/cm$^2$) to the forearm of a healthy subject and allowed to thoroughly dry (typically a minimum of 10 minutes) over an area of approximately 5×5 cm. The dried composition was gently washed with 23° C. normal saline (0.9% by weight sodium chloride). The saline washed site was exposed to a known quantity of bacteria in an inoculum of about 10$^6$ bacteria/ml (typically *Staphylococcus epidermidis* or *E. coli*) for 30 minutes. The bacteria were recovered and treated with an effective neutralizer and incubated to quantify the bacteria remaining. Particularly preferred compositions retain at least 1 log reduction and preferably at least 2 log reduction of bacteria after a gentle rinse with 500 mL saline poured over the site by placing the saline container as close to the site as possible so as to not have the saline fall onto the site.

Significantly, certain embodiments of the present invention have a very low potential for generating microbial resistance. For example, preferred compositions of the present invention have an increase in the ratio of final to initial MIC levels (i.e., minimum inhibitory concentration) of less than 16, more preferably less than 8, and even more preferably less than 4. Such an emergence of resistance assay should be carried out such that the microorganisms are subjected initially to sub MIC levels (e.g., ½ the MIC) of antiseptic and after 24 hours the microorganisms passed into broth containing twice the concentration of antiseptic. This is repeated for 8 days and each day microorganisms are removed to determine the new MIC. Thus, such compositions can be applied multiple times over one or more days to treat topical infections or to eradicate unwanted bacteria (such as nasal colonization of *Staphylococcus aureus*).

Preferred compositions of the present invention contain an effective amount of antimicrobial component to rapidly kill or inactivate microorganisms on skin, skin lesions, and mucosal membranes. In certain embodiments, essentially all the microorganisms are eradicated or inactivated within five days, preferably within three days, more preferably two days, and most preferably within 24 hours using one or more doses.

Preferred compositions of the present invention have a generally low irritation level for skin, skin lesions, and mucosal membranes (including the anterior nares, nasal cavities, nasopharangyl cavity and other portions of the upper respiratory tract). Many of the compositions of the present invention may be beneficial to these tissues by providing emolliency. In fact, the antimicrobial lipids of this invention have excellent emolliency on skin. For example, certain preferred compositions of the present invention are no more irritating than BACTROBAN ointment (on skin) or BACTROBAN NASAL (in the anterior nares) products available from Glaxo Smith Kline.

Preferred compositions of the present invention are substantive for relatively long periods of time to ensure adequate efficacy. For example, certain compositions of the present invention remain at the site of application with antimicrobial activity for at least 4 hours and more preferably at least 8 hours.

Preferred compositions of the present invention are physically stable. As defined herein "physically stable" compositions are those that do not significantly change due to substantial precipitation, crystallization, phase separation, and the like, from their original condition during storage at 23° C. for at least 3 months, and preferably for at least 6 months. Particularly preferred compositions are physically stable if a 10-milliliter (10-mL) sample of the composition when placed in a 15-mL conical-shaped graduated plastic centrifuge tube (Corning) and centrifuged at 3,000 revolutions per minute (rpm) for 10 minutes using a Labofuge B, model 2650 manufactured by Heraeus Sepatech GmbH, Osterode, West Germany (or similar centrifuge at 2275×g) has no visible phase separation in the bottom or top of the tube.

Preferred compositions of the present invention exhibit good chemical stability. This can be especially a concern with the antimicrobial fatty acid esters, which can often undergo transesterification, for example. Preferred compositions retain at least 85%, more preferably at least 90%, even more preferably at least 92%, and even more preferably at least 95%, of the antimicrobial component after aging for 4 weeks at 40° C. (an average of three samples) beyond the initial 5-day equilibration period at 23° C. The most preferred compositions retain an average of at least 97% of the antimicrobial component after aging for 4 weeks at 40° C. in a sealed container beyond the initial 5-day equilibration period at 23° C. The percent retention is understood to mean the weight percent of antimicrobial component retained. This is determined by comparing the amount remaining in a sample aged (i.e., aged beyond the initial 5-day equilibration period) in a sealed container that does not cause degradation, to the actual measured level in an identically prepared sample (preferably from the same batch) and allowed to sit at 23° C. for five days. The level of antimicrobial component is preferably determined using gas chromatography as described in the Aging Study Using Gas Chromatography test method included in the Examples Section.

Generally, the compositions of this invention may be in one of the following forms:

A hydrophobic ointment: The compositions are formulated with a hydrophobic base (e.g., petrolatum, thickened or gelled water insoluble oils, and the like) and optionally having a minor amount of a water soluble phase.

An oil-in-water emulsion: The compositions may be formulations in which the antimicrobial component is emulsified into an emulsion comprising a discrete phase of a hydrophobic component and a continuous aqueous phase that includes water and optionally one or more polar hydrophilic carrier(s) as well as salts, surfactants, emulsifiers, and other components. These emulsions may include water-soluble or water-swellable polymers as well as one or more emulsifier(s) that help to stabilize the emulsion. These emulsions generally have higher conductivity values, as described in International Publication No. WO 2003/028767.

A water-in-oil emulsion: The compositions may be formulations in which the antimicrobial component is incorporated into an emulsion that includes a continuous phase of a hydrophobic component and an aqueous phase that includes water and optionally one or more polar hydrophilic carrier(s) as well as salts or other components. These emulsions may include oil-soluble or oil-swellable polymers as well as one or more emulsifier(s) that help to stabilize the emulsion.

Thickened Aqueous gels: These systems include an aqueous phase which may or may not be thickened. For most topical applications the composition preferably has been thickened to achieve a viscosity of at least 500 centipoise (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). The viscosity is determined using the Viscosity Test described herein. These systems can be thickened by suitable natural, modified natural, or synthetic polymers as described below. Alternatively, the thickened aqueous gels can be thickened using suitable polyethoxylated alkyl chain surfactants that effectively thicken the composition as well as other nonionic, cationic, or anionic emulsifier systems. Preferably, cationic or anionic emulsifier systems are chosen since some polyethoxylated emulsifiers can inactivate the antimicrobial lipids especially at higher concentrations. For certain embodiments, anionic emulsifier systems are used. Examples include the nonioinic systems such as POLAWAX, COSMOWAX, and CROTHIX systems as well as cationic (BEHENYL TMS) and anionic (CRODAPHOS CES) systems from Croda Inc.

Hydrophilic gels: These are systems in which the continuous phase includes at least one water soluble hydrophilic component other than water. The formulations may optionally also contain water up to 20% by weight. Higher levels may be suitable in some compositions. Suitable hydrophilic components include one or more glycols such as glycerin, propylene glycol, butylene glycols, etc., polyethylene glycols (PEG), random or block copolymers of ethylene oxide, propylene oxide, and/or butylene oxide, polyalkoxylated surfactants having one or more hydrophobic moieties per molecule, silicone copolyols, as well as combinations thereof, and the like. One skilled in the art will recognize that the level of ethoxylation should be sufficient to render the hydrophilic component water soluble or water dispersible at 23° C. In most embodiments, the water content is less than 20%, preferably less than 10%, and more preferably less than 5% by weight of the composition.

Antimicrobial Component

The antimicrobial component is that component of the composition that provides at least part of the antimicrobial activity. That is, the antimicrobial component has at least some antimicrobial activity for at least one microorganism. It is generally considered the main active component of the compositions of the present invention. The antimicrobial component includes one or more fatty alcohol esters of hydroxycarboxylic acids, alkoxylated derivatives thereof, or combinations thereof.

More specifically and preferably, the antimicrobial component includes a (C7-C14) saturated fatty alcohol ester (preferably a monoester) of a (C2-C8)hydroxycarboxylic acid (preferably, a (C7-C12) saturated fatty alcohol ester (preferably a monoester) of a (C2-C8)hydroxycarboxylic acid, and more preferably, a (C8-C12) saturated fatty alcohol ester (preferably a monoester) of a (C2-C8)hydroxycarboxylic acid), a (C8-C22)mono- or poly-unsaturated fatty alcohol ester (preferably a monoester) of a (C2-C8)hydroxycarboxylic acid, an alkoxylated derivative of either of the foregoing, or combinations thereof. Herein, a "monoester" is that there is only 1 alkyl or aralkyl group and thus a free hydroxyl group. The hydroxycarboxylic acid moiety can include aliphatic and/or aromatic groups. For example, fatty alcohol esters of salicylic acid are possible.

A fatty alcohol ester of a hydroxyl functional carboxylic acid preferably has the formula:

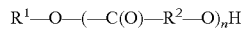

$$R^1-O-(-C(O)-R^2-O)_nH$$

wherein $R^1$ is the residue of a (C7-C14) saturated alkyl alcohol (preferably, a (C7-C12) saturated alkyl alcohol, more preferably, a (C8-C12) saturated alkyl alcohol), or a (C8-C22) unsaturated alcohol (including polyunsaturated alcohol), $R^2$ is the residue of a hydroxycarboxylic acid wherein the hydroxycarboxylic acid has the following formula:

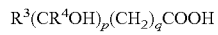

$$R^3(CR^4OH)_p(CH_2)_qCOOH$$

wherein: $R^3$ and $R^4$ are each independently H or a (C1-C8) saturated straight, branched, or cyclic alkyl group, a (C6-C12)aryl group, or a (C6-C12)aralkyl or (C6-C12)alkaryl group (wherein the alkyl groups of the aralkyl and alkaryl groups are saturated straight, branched, or cyclic), wherein $R^3$ and $R^4$ may be optionally substituted with one or more carboxylic acid groups; p=1 or 2; and q=0-3; and n=1, 2, or 3. The $R^1$ group may include one or more free hydroxyl groups, but preferably is free of hydroxyl groups. Preferred fatty alcohol esters of hydroxycarboxylic acids are esters derived from branched or straight chain C8, C9, C10, C11, and C12 alkyl alcohols. The hydroxyacids typically have one hydroxyl group and one carboxylic acid group.

Exemplary fatty alcohol esters of hydroxycarboxylic acids include, but are not limited to, (C7-C14), and preferably (C8-C12), fatty alcohol esters of lactic acid such as octyl lactate, 2-ethylhexyl lactate (PURASOLV EHL from Purac, Lincolnshire, Ill.), lauryl lactate (CHRYSTAPHYL 98 from Chemic Laboratories, Canton, Mass.), lauryl lactyl lacate, 2-ethylhexyl lactyl lactate; (C7-C14), and preferably (C8-C12), fatty alcohol esters of glycolic acid, lactic acid, 3-hydroxybutanoic acid, mandelic acid, gluconic acid, tartaric acid, and salicylic acid.

The alkoxylated derivatives of the aforementioned compounds (e.g., one which is ethoxylated and/or propoxylated on the remaining alcohol group(s)) also have antimicrobial activity as long as the total alkoxylate is kept relatively low. The preferred alkoxylation level is less than 5, and more preferably less than 2, per mole of hydroxycarboxylic acid.

They can be alkoxylated, preferably ethoxylated and/or propoxylated, by conventional techniques. Alkoxylating compounds are preferably selected from the group consisting of ethylene oxide, propylene oxide, and mixtures thereof, and similar oxirane compounds.

The compositions of the present invention include one or more fatty alcohol esters of hydroxyacids, or alkoxylated derivatives thereof at a suitable level to produce the desired result. Such compositions preferably include a total amount of such material of at least 0.01 percent by weight (wt-%), more preferably at least 0.1 wt-%, even more preferably at least 0.25 wt-%, even more preferably at least 0.5 wt-%, even more preferably at least 0.6 wt-%, even more preferably at least 0.7 wt-%, even more preferably at least 0.8 wt-%, even more preferably at least 0.9 wt-%, and even more preferably at least 1 wt-%, based on the total weight of the "ready to use" or "as used" composition. In a preferred embodiment, they are present in a total amount of up to 99% or more. In high concentration the antimicrobial component may be the vehicle. This is possible because these compounds have very good skin compatibility and are good solvents for many of the surfactants, enhancers, and other components that may be incorporated. Generally, the compositions contain no greater than 50 wt-%, more preferably no greater than 25 wt-%, even more preferably no greater than 15 wt-%, and even more preferably no greater than 10 wt-%, based on the "ready to use" or "as used" composition. Certain compositions include higher concentrations may be used as concentrates that are intended to be diluted prior to use.

The antimicrobial esters of the present invention are preferably used in a relatively pure form. For example, fatty alcohol ester in the antimicrobial components that are greater than 60%, greater than 70%, greater than 80%, or greater than 90% pure fatty alcohol monoester of a hydroxy acid have significantly greater activity than those relatively impure preparations of these esters. The relatively impure compositions, such as CERAPHYL 31 (ISP Corp.) having approximately 50% lauryl lactate by weight as determined by GC has little, no, or slower activity. These relatively impure esters have a significant concentration of residual fatty alcohol remaining. While not being bound by theory, it is believed that impurities such as the fatty alcohol can reduce the availability of the active antimicrobial ester to kill or inactivate the microorganisms.

To achieve rapid antimicrobial activity, formulations may incorporate one or more antimicrobial components in the composition approaching, or preferably exceeding, the solubility limit in the hydrophobic phase. White not intended to be bound by theory, it appears that antimicrobial lipids that preferably partition into the hydrophobic component are not readily available to kill microorganisms which are in or associated with an aqueous phase in or on the tissue. In most compositions the antiseptic is preferably incorporated in at least 60%, preferably, at least 75%, more preferably, at least 100%, and most preferably, at least 120%, of the solubility limit of the hydrophobic component at 23° C. This in conveniently determined by making the formulation without the antimicrobial, separating the phases (e.g., by centrifugation or other suitable separation technique) and determining the solubility limit by addition of progressively greater levels of the antimicrobial lipid until precipitation occurs. One skilled in the art will realize that creation of supersaturated solutions must be avoided for an accurate determination.

Enhancer Component

Compositions of the present invention include an enhancer component (preferably a synergist) to enhance the antimicrobial activity especially against Gram negative bacteria, such as *E. coli* and *Pseudomonas* sp. The enhancer chosen preferably effects the cell envelope of the bacteria. While not bound by theory, it is presently believed that the enhancer functions by allowing the antiseptic to more easily enter the cell cytoplasm and/or by facilitating disruption of the cell envelope. The enhancer component may include an alpha-hydroxy acid, a beta-hydroxy acid, other carboxylic acids, a phenolic compound (such as certain antioxidants and parabens), a monohydroxy alcohol, a chelating agent, a glycol ether (i.e., ether glycol), or a sugar and/or sugar alcohol. Various combinations of enhancers can be used if desired.

The alpha-hydroxy acid, beta-hydroxy acid, and other carboxylic acid enhancers are preferably present in their protonated, free acid form. It is not necessary for all of the acidic enhancers to be present in the free acid form, however, the preferred concentrations listed below refer to the amount present in the free acid form. Furthermore, the chelator enhancers that include carboxylic acid groups are preferably present with at least one, and more preferably at least two, carboxylic acid groups in their free acid form. The concentrations given below assume this to be the case.

One or more enhancers may be used in the compositions of the present invention at a suitable level to produce the desired result. In a preferred embodiment, they are present in a total amount of at least 0.01 wt-%, based on the total weight of the ready to use composition. In a preferred embodiment, they are present in a total amount of no greater than 20 wt-%, based on the total weight of the ready to use composition. Such concentrations typically apply to alpha-hydroxy acids, beta-hydroxy acids, other carboxylic acids, chelating agents, phenolics, ether glycols, and (C5-C10) monohydroxy alcohols. Generally, higher concentrations are needed for (C1-C4)monohydroxy alcohols, as described in greater detail below.

The total concentration of the enhancer component relative to the total concentration of the antimicrobial component is preferably within a range of 10:1 to 1:300, and more preferably 5:1 to 1:10, on a weight basis.

An additional consideration when using an enhancer is the solubility and physical stability in the compositions. Many of the enhancers discussed herein are insoluble in preferred hydrophobic components such as petrolatum. It has been found that the addition of a minor amount (typically less than 30 wt-%, preferably less than 20 wt-%, and more preferably less than 12 wt-%) of a hydrophilic component not only helps dissolve and physically stabilize the composition but improves the antimicrobial activity as well. These hydrophilic components are described below.

Alternatively, the enhancer component may be present in excess of the solubility limit provided that the composition is physically stable. This may be achieved by utilizing a sufficiently viscous composition that stratification (e.g., settling or creaming) of the antiseptic does not appreciably occur.

Alpha-Hydroxy Acids

An alpha-hydroxy acid is typically a compound represented by the formula:

$$R^5(CR^6OH)_nCOOH$$

wherein: $R^5$ and $R^6$ are each independently H, a (C1-C8) alkyl group (straight, branched, or cyclic group), a (C6-C12) aryl group, a (C6-C12)aralkyl group, or a (C6-C12)alkaryl group (wherein the alkyl group of the aralkyl or alkaryl is straight, branched, or cyclic), wherein $R^5$ and $R^6$ may be optionally substituted with one or more carboxylic acid groups; and n=1-3, preferably, n=1-2.

Exemplary alpha-hydroxy acids include, but are not limited to, lactic acid, malic acid, citric acid, 2-hydroxybutanoic acid, mandelic acid, gluconic acid, glycolic acid (i.e., alpha-hydroxyethanoic acid), tartaric acid, alpha-hydroxyoctanoic acid, and alpha-hydroxycaprylic acid, as well as derivatives thereof (e.g., compounds substituted with hydroxyls, phenyl groups, hydroxyphenyl groups, alkyl groups, halogens, as well as combinations thereof). Preferred alpha-hydroxy acids include lactic acid, malic acid, and mandelic acid. These acids may be in D, L, or DL form and may be present as free acid, lactone, or partial salts thereof. All such forms are encompassed by the term "acid." Preferably, the acids are present in the free acid form. In certain preferred embodiments, the alpha-hydroxy acids useful in the compositions of the present invention are selected from the group consisting of lactic acid, mandelic acid, and malic acid, and mixtures thereof. Other suitable alpha-hydroxy acids are described in U.S. Pat. No. 5,665,776 (Yu).

One or more alpha-hydroxy acids may be used in the compositions of the present invention at a suitable level to produce the desired result. In a preferred embodiment, they are present in a total amount of at least 0.25 wt-%, more preferably, at least 0.5 wt-%, and even more preferably, at least 1 wt-%, based on the total weight of the ready to use composition. In a preferred embodiment, they are present in a total amount of no greater than 10 wt-%, more preferably, no greater than 5 wt-%, and even more preferably, no greater than 3 wt-%, based on the total weight of the ready to use composition. Higher concentrations may become irritating.

The ratio of alpha-hydroxy acid enhancer to total antimicrobial component is preferably at most 10:1, more preferably at most 5:1, and even more preferably at most 1:1. The ratio of alpha-hydroxy acid enhancer to total antimicrobial component is preferably at least 1:20, more preferably at least 1:12, and even more preferably at least 1:5. Preferably the ratio of alpha-hydroxy acid enhancer to total antimicrobial component is within a range of 1:12 to 1:1.

Beta-Hydroxy Acids

A beta-hydroxy acid is typically a compound represented by the formula:

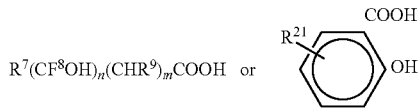

wherein: $R^7$, $R^8$, and $R^9$ are each independently H, a (C1-C8)alkyl group (saturated straight, branched, or cyclic group), a (C6-C12)aryl group, a (C6-C12)aralkyl group, or a (C6-C12)alkaryl group (wherein the alkyl group of the alkaryl or aralkyl is straight, branched, or cyclic), wherein R⁷ and R⁸ may be optionally substituted with one or more carboxylic acid groups; m=0 or 1; n=1-3 (preferably, n=1-2); and $R^{21}$ is H, (C1-C4)alkyl or a halogen.

Exemplary beta-hydroxy acids include, but are not limited to, salicylic acid, beta-hydroxybutanoic acid, tropic acid, 4-aminosalicyclic acid, and trethocanic acid. In certain preferred embodiments, the beta-hydroxy acids useful in the compositions of the present invention are selected from the group consisting of salicylic acid, beta-hydroxybutanoic acid, and mixtures thereof. Other suitable beta-hydroxy acids are described in U.S. Pat. No. 5,665,776 (Yu).

One or more beta-hydroxy acids may be used in the compositions of the present invention at a suitable level to produce the desired result. In a preferred embodiment, they are present in a total amount of at least 0.1 wt-%, more preferably at least 0.25 wt-%, and even more preferably at least 0.5 wt-%, based on the total weight of the ready to use composition. In a preferred embodiment, they are present in a total amount of no greater than 10 wt-%, more preferably no greater than 5 wt-%, and even more preferably no greater than 3 wt-%, based on the total weight of the ready to use composition. Higher concentrations may become irritating.

The ratio of beta-hydroxy acid enhancer to total antimicrobial component is preferably at most 10:1, more preferably at most 5:1, and even more preferably at most 1:1. The ratio of beta-hydroxy acid enhancer to total antimicrobial component is preferably at least 1:20, more preferably at least 1:15, and even more preferably at least 1:10. Preferably the ratio of beta-hydroxy acid enhancer to total antimicrobial component is within a range of 1:15 to 1:1.

In systems with low concentrations of water, or that are essentially free of water, transesterification may be the principle route of loss of the fatty acid monoester and alkoxylated derivatives of these active ingredients and loss of carboxylic acid containing enhancers may occur due to esterification. Thus, certain alpha-hydroxy acids (AHA) and beta-hydroxy acids (BHA) are particularly preferred since these are believed to be less likely to transesterify the ester antimicrobial or other esters by reaction of the hydroxyl group of the AHA or BHA. For example, salicylic acid may be particularly preferred in certain formulations since the phenolic hydroxyl group is much more acidic than an aliphatic hydroxyl group and thus much less likely to react. Other particularly preferred compounds in anhydrous or low-water content formulations include lactic, mandelic, malic, citric, tartaric, and glycolic acid. Benzoic acid and substituted benzoic acids that do not include a hydroxyl group, while not hydroxy acids, are also preferred due to a reduced tendency to form ester groups.

Other Carboxylic Acids

Carboxylic acids other than alpha- and beta-carboxylic acids are suitable for use in the enhancer component. These include alkyl, aryl, aralkyl, or alkaryl carboxylic acids typically having equal to or less than 16, and often equal to or less than 12, carbon atoms. A preferred class of these can be represented by the following formula:

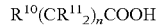

wherein: $R^{10}$ and $R^{11}$ are each independently H or a (C1-C4)alkyl group (which can be a straight, branched, or cyclic group), a (C6-C12)aryl group, a (C6-C16) group containing both aryl groups and alkyl groups (which can be a straight, branched, or cyclic group), wherein $R^{10}$ and $R^{11}$ may be optionally substituted with one or more carboxylic acid groups; and n=0-3, preferably, n=0-2. Preferably, the carboxylic acid is a (C1-C4)alkyl carboxylic acid, a (C6-C12) aralkyl carboxylic acid, or a (C6-C16)alkaryl carboxylic acid.

Exemplary acids include, but are not limited to, acetic acid, propionic acid, benzoic acid, benzylic acid, nonylbenzoic acid, p-hydroxybenzoic acid, retinoic acid, and the like. Particularly preferred is benzoic acid.

One or more carboxylic acids (other than alpha- or beta-hydroxy acids) may be used in the compositions of the present invention at a suitable level to produce the desired result. In a preferred embodiment, they are present in a total amount of at least 0.1 wt-%, more preferably at least 0.25 wt-%, even more preferably at least 0.5 wt-%, and most preferably at least 1 wt-%, based on the ready to use concentration composition. In a preferred embodiment, they are present in a total amount of no greater than 10 wt-%, more preferably no greater than 5 wt-%, and even more preferably no greater than 3 wt-%, based on the ready to use composition.

The ratio of the total concentration of carboxylic acids (other than alpha- or beta-hydroxy acids) to the total concentration of the antimicrobial component is preferably within a range of 10:1 to 1:100, and more preferably 2:1 to 1:10, on a weight basis.

Chelators

A chelating agent (i.e., chelator) is typically an organic compound capable of multiple coordination sites with a metal ion in solution. Typically these chelating agents are polyanionic compounds and coordinate best with polyvalent metal ions. Exemplary chelating agents include, but are not limited to, ethylene diamine tetraacetic acid (EDTA) and salts thereof (e.g., $EDTA(Na)_2$, $EDTA(Na)_4$, EDTA(Ca), $EDTA(K)_2$), sodium acid pyrophosphate, acidic sodium hexametaphosphate, adipic acid, succinic acid, polyphosphoric acid, sodium acid pyrophosphate, sodium hexametaphosphate, acidified sodium hexametaphosphate, nitrilotris (methylenephosphonic acid), diethylenetriaminepentaacetic acid, ethylenebis(oxyethylenenitrilo)tetraacetic acid, glycolether diaminetetraacetic acid, ethyleneglycol-O,O'bis(2-aminoethyl)-N,N,N',N'-tetraacetic acid (EGTA), N-(2-hydroxyethyl)ethylenediamine-N,N',N'-triacetic acid trisodium salt (HETA), polyethylene glycol diaminetetraacetic acid, 1-hydroxyethylene, 1,1-diphosphonic acid (HEDP), and diethylenetriaminepenta-(methylenephosphonic acid). Any of these chelating agents may also be used in their partial or complete salt form. Certain carboxylic acids, particularly the alpha-hydroxy acids and beta-hydroxy acids, can also function as chelators, e.g., malic acid, citric, and tartaric acid.

Also included as chelators are compounds highly specific for binding ferrous and/or ferric ion such as siderophores, and iron binding proteins. Iron binding proteins include, for example, lactoferrin, and transferrin. Siderophores include, for example, enterochelin, enterobactin, vibriobactin, anguibactin, pyochelin, pyoverdin, and aerobactin.

In certain preferred embodiments, the chelating agents useful in the compositions of the present invention include those selected from the group consisting of ethylenediaminetetraacetic acid and salts thereof, succinic acid, and mixtures thereof. Preferably, either the free acid or the mono- or di-salt form of EDTA is used.

One or more chelating agents may be used in the compositions of the present invention at a suitable level to produce the desired result. In a preferred embodiment, they are present in a total amount of at least 0.01 wt-%, more preferably at least 0.05 wt-%, even more preferably at least 0.1 wt-%, and even more preferably at least 1 wt-%, based on the weight of the ready to use composition. In a preferred embodiment, they are present in a total amount of no greater than 10 wt-%, more preferably no greater than 5 wt-%, and even more preferably no greater than 1 wt-%, based on the weight of the ready to use composition.

The ratio of the total concentration of chelating agents (other than alpha- or beta-hydroxy acids) to the total concentration of the antimicrobial component is preferably within a range of 10:1 to 1:100, and more preferably 1:1 to 1:10, on a weight basis.

Phenolic Enhancer Compounds

A phenolic compound enhancer is typically a compound having the following general structure:

wherein: m is 0 to 3 (especially 1 to 3), n is 1 to 3 (especially 1 to 2), each $R^{12}$ independently is alkyl or alkenyl of up to 12 carbon atoms (especially up to 8 carbon atoms) optionally substituted with O in or on the chain (e.g., as a carbonyl group) or OH on the chain, and each $R^{13}$ independently is H or alkyl or alkenyl of up to 8 carbon atoms (especially up to 6 carbon atoms) optionally substituted with O in or on the chain (e.g., as a carbonyl group) or OH on the chain, but where $R^{13}$ is H, n preferably is 1 or 2.

Examples of phenolic enhancers include, but are not limited to, butylated hydroxy anisole, e.g., 3(2)-tert-butyl-4-methoxyphenol (BHA), 2,6-di-tert-butyl-4-methylphenol (BHT), 3,5-di-tert-butyl-4-hydroxybenzylphenol, 2,6-di-tert-4-hexylphenol, 2,6-di-tert-4-octylphenol, 2,6-di-tert-4-decylphenol, 2,6-di-tert-butyl-4-ethylphenol, 2,6-di-tert-4-butylphenol, 2,5-di-tert-butylphenol, 3,5-di-tert-butylphenol, 4,6-di-tert-butyl-resorcinol, methyl paraben (4-hydroxybenzoic acid methyl ester), ethyl paraben, propyl paraben, butyl paraben, as well as combinations thereof. A preferred group of the phenolic compounds is the phenol species having the general structure shown above where $R^{13}$=H and where $R^{12}$ is alkyl or alkenyl of up to 8 carbon atoms, and n is 1, 2, or 3, especially where at least one $R^{12}$ is butyl and particularly tert-butyl, and especially the non-toxic members thereof. Some of the preferred phenolic synergists are BHA, BHT, methyl paraben, ethyl paraben, propyl paraben, and butyl paraben as well as combinations of these.

One or more phenolic compounds may be used in the compositions of the present invention at a suitable level to produce the desired result. The concentrations of the phenolic compounds in medical-grade compositions may vary widely, but as little as 0.001 wt-%, based on the total weight of the composition, can be effective when the above-described esters are present within the above-noted ranges. In a preferred embodiment, they are present in a total amount of at least 0.01 wt-%, more preferably at least 0.10 wt-%, and even more preferably at least 0.25 wt-%, based on the ready to use composition. In a preferred embodiment, they are present in a total amount of no greater than 8 wt-%, more preferably no greater than 4 wt-%, and even more preferably no greater than 2 wt-%, based on the ready to use composition.

It is preferred that the ratio of the total phenolic concentration to the total concentration of the antimicrobial component be within a range of 10:1 to 1:300, and more preferably within a range of 1:1 to 1:10, on a weight basis.

The above-noted concentrations of the phenolics are normally observed unless concentrated formulations for subsequent dilution are intended. On the other hand, the minimum concentration of the phenolics and the antimicrobial components to provide an antimicrobial effect will vary with the particular application.

Monohydroxy Alcohols

An additional enhancer class includes monohydroxy alcohols having 1-10 carbon atoms. This includes the lower (i.e., C1-C4) monohydroxy alcohols (e.g., methanol, ethanol, isopropanol, and butanol) as well as longer chain (i.e., C5-C10) monohydroxy alcohols (e.g., isobutanol, t-butanol, octanol, and decanol). Other useful alcohols include benzyl alcohol and menthol. In certain preferred embodiments, the alcohols useful in the compositions of the present invention are selected from the group consisting of methanol, ethanol, isopropyl alcohol, and mixtures thereof.

One or more alcohols may be used in the compositions of the present invention at a suitable level to produce the desired result. In a preferred embodiment, the short chain (i.e., C1-C4)alcohols are present in a total amount of at least 10 wt-%, even more preferably at least 15 wt-%, even more preferably at least 20 wt-%, and even more preferably at least 25 wt-%, based on the total weight of the ready to use composition.

In a preferred embodiment, the (C1-C4)alcohols are present in a total amount of no greater than 90 wt-%, more preferably no greater than 70 wt-%, even more preferably no greater than 60 wt-%, and even more preferably no greater than 50 wt-%, based on the total weight of the ready to use composition.

For certain applications, lower alcohols may not be preferred due to the strong odor and potential for stinging and irritation. This can occur especially at higher levels. In applications where stinging or burning is a concern, the concentration of (C1-C4)alcohols is preferably less than 20 wt-%, more preferably less than 15 wt-%.

In another preferred embodiment longer chain (i.e., C5-C10)alcohols are present in a total amount of at least 0.1 wt-%, more preferably at least 0.25 wt-%, and even more preferably at least 0.5 wt-%, and most preferably at least 1.0%, based on the ready to use composition. In a preferred embodiment, the (C5-C10)alcohols are present in a total amount of no greater than 10 wt-%, more preferably no greater than 5 wt-%, and even more preferably no greater than 2 wt-%, based on the total weight of the ready to use composition.

Ether Glycols

An additional enhancer class includes ether glycols (also referred to as glycol ethers). Exemplary ether glycols include those of the formula:

wherein R'=H, a (C1-C8)alkyl, a (C6)aryl group, a (C6-C12)aralkyl group, or a (C6-C12)alkaryl group; and each R" is independently =H, methyl, or ethyl; and n=0-5, preferably 1-3. Examples include 2-phenoxyethanol, dipropylene glycol, triethylene glycol, the line of products available under the trade designation DOWANOL DB (di(ethylene glycol) butyl ether), DOWANOL DPM (di(propylene glycol)monomethyl ether), and DOWANOL TPnB (tri(propylene glycol) monobutyl ether), as well as many others available from Dow Chemical, Midland, Mich.

One or more ether glycols may be used in the compositions of the present invention at a suitable level to produce the desired result. In a preferred embodiment, they are present in a total amount of at least 0.01 wt-%, based on the total weight of the ready to use composition. In a preferred embodiment, they are present in a total amount of no greater than 20 wt-%, based on the total weight of the ready to use composition.

Sugars and Sugar Alcohols

Suitable sugars can include both monosaccharides and disaccharides. Suitable monosaccharides include, but are not limited to, mannose, xylose, maltose, sorbose, and their corresponding sugar alcohols mannitol, xylitol, maltitol, and sorbitol. In certain preferred embodiments, the sugar is selected from the group consisting of mannose, xylose, mannitol, xylitol, and combinations thereof. In certain embodiments, the sugar is a disaccharide of xylitol and glucose. For disaccharides, at least one of the sugars is preferably one of the suitable monosaccharides listed herein. The second sugar unit may be selected from any suitable sugar commonly used in food products, such as but not limited to, glucose, fructose, mannose, xylose, galacose, sorbose, and sorbitol.

One or more sugars or sugar alcohols may be used in the compositions described herein at a suitable level to produce the desired result. In a preferred embodiment, they are present in a total amount of at least 0.5 wt-% and preferably at least 1.0% based on the total weight of the ready to use composition. In a preferred embodiment, they are present in a total amount of no greater than 20 wt-%, based on the total weight of the ready to use composition.

Surfactant Component

Compositions of the present invention can include one or more surfactants to emulsify the composition and to help wet the surface and/or to aid in contacting the microorganisms. As used herein the term "surfactant" means an amphiphile (a molecule possessing both polar and nonpolar regions which are covalently bound) capable of reducing the surface tension of water and/or the interfacial tension between water and an immiscible liquid. The term is meant to include soaps, detergents, emulsifiers, surface active agents, and the like. The surfactant can be cationic, anionic, nonionic, or amphoteric. This includes a wide variety of conventional surfactants. Combinations of various surfactants can be used if desired.

Certain ethoxylated surfactants may reduce or eliminate the antimicrobial efficacy of the antimicrobial component. The exact mechanism of this is not known and not all ethoxylated surfactants display this negative effect. For example, poloxamer (polyethylene oxide/polypropylene oxide) surfactants have been shown to be compatible with the antimicrobial component, but ethoxylated sorbitan fatty acid esters such as those sold under the trade name TWEEN by ICI have not been compatible. It should be noted that these are broad generalizations and the activity could be formulation dependent. One skilled in the art can easily determine compatibility of a surfactant by making the formulation and testing for antimicrobial activity as described in the Examples Section.

It should be noted that certain antimicrobial lipids are amphiphiles and may be surface active. For example, certain antimicrobial alkyl monoglycerides described herein are surface active. For the purposes of this invention, the antimicrobial component is considered distinct from a "surfactant" component.

Preferred surfactants are those that have an HLB (i.e., hydrophile to lipophile balance) of at least 4 and more preferably at least 8. Even more preferred surfactants have an HLB of at least 12. Most preferred surfactants have an HLB of at least 15; however, lower HLB surfactants are still useful in compositions described herein.

Preferred surfactants also have a critical micelle concentration greater than $1 \times 10^{-5}$ moles/liter, preferably greater than $1 \times 10^{-4}$ moles/liter and most preferably greater than $1 \times 10^{-3}$ moles/liter. Other preferred surfactants do not form micelles such as the Poloxamer surfactants.

Examples of the various classes of surfactants are described below. In certain preferred embodiments, the surfactants useful in the compositions of the present invention are selected from the group consisting of sulfonate surfactants, sulfate surfactants, phosphonate surfactants, phosphate surfactants, poloxamer surfactants (polyethylene oxide/polypropylene oxide block copolymers), cationic surfactants, and mixtures thereof. In certain more preferred embodiments, the surfactants useful in the compositions of the present invention are selected from the group consisting of sulfonate surfactants, sulfate surfactants, phosphate surfactants, and mixtures thereof.

One or more surfactants may be used in the compositions of the present invention at a suitable level to produce the desired result. In a preferred embodiment, they are present in a total amount of at least 0.1 wt-%, more preferably at least 0.5 wt-%, and even more preferably at least 1.0 wt-%, based on the total weight of the ready to use composition. Many of the compositions of the present invention are intended to be left on tissue for the desired indication, e.g., decolonizing nasal tissue or treating impetigo. Therefore, in order to avoid irritation in a preferred embodiment, they are present in a total amount of no greater than 10 wt-%, more preferably no greater than 5 wt-%, even more preferably no greater than 3 wt-%, and even more preferably no greater than 2 wt-%, based on the total weight of the ready to use composition. The ratio of the total concentration of surfactant to the total concentration of the antimicrobial component is preferably within a range of 5:1 to 1:100, more preferably 3:1 to 1:10, and most preferably 2:1 to 1:3, on a weight basis.

Cationic Surfactants

Exemplary cationic surfactants include, but are not limited to, salts of optionally polyoxyalkylenated primary, secondary, or tertiary fatty amines; quaternary ammonium salts such as tetraalkylammonium, alkylamidoalkyltrialkylammonium, trialkylbenzylammonium, trialkylhydroxyalkylammonium, or alkylpyridinium halides (preferably chlorides or bromides) as well as other anionic counterions, such as but not limited to, alkyl sulfates, such as but not limited to, methosulfate and ethosulfate; imidazoline derivatives; amine oxides of a cationic nature (e.g., at an acidic pH).

In certain preferred embodiments, the cationic surfactants useful in the compositions of the present invention are selected from the group consisting of tetraalkyl ammonium, trialkylbenzylammonium, and alkylpyridinium halides as well as other anionic counterions, such as but not limited to, alkyl sulfates, such as but not limited to, methosulfate and ethosulfate, and mixtures thereof.

Amine Oxides

Also particularly preferred are amine oxide surfactants, which can be cationic or nonionic depending on the pH (e.g., cationic at lower pH and nonionic at higher pH). Amine oxide surfactants including alkyl and alkylamidoalkyldialkylamine oxides of the following formula:

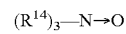

wherein $R^{14}$ is a (C1-C30)alkyl group (preferably a (C1-C14)alkyl group) or a (C6-C18)aralkyl or alkaryl group, wherein any of these groups can be optionally substituted in or on the chain by N-, O-, or S-containing groups such as amide, ester, hydroxyl, and the like. Each $R^{14}$ may be the same or different provided at least one $R^{14}$ group includes at least eight carbons. Optionally, the $R^{14}$ groups can be joined to form a heterocyclic ring with the nitrogen to form surfactants such as amine oxides of alkyl morpholine, alkyl piperazine, and the like. Preferably two $R^{14}$ groups are methyl and one $R^{14}$ group is a (C12-C16)alkyl or alkylamidopropyl group. Examples of amine oxide surfactants include those commercially available under the trade designations AMMONYX LO, LMDO, and CO, which are lauryldimethylamine oxide, laurylamidopropyldimethylamine oxide, and cetyl amine oxide, all from Stepan Company.

Anionic Surfactants

Exemplary anionic surfactants include, but are not limited to, sarcosinates, glutamates, alkyl sulfates, sodium or potassium alkyleth sulfates, ammonium alkyleth sulfates, ammonium laureth-n-sulfates, laureth-n-sulfates, isethionates, glycerylether sulfonates, sulfosuccinates, alkylglyceryl ether sulfonates, alkyl phosphates, aralkyl phosphates, alkylphosphonates, and aralkylphosphonates. These anionic surfactants may have a metal or organic ammonium counterion. In certain preferred embodiments, the anionic surfactants useful in the compositions of the present invention are selected from the group consisting of:

1. Sulfonates and Sulfates. Suitable anionic surfactants include sulfonates and sulfates such as alkyl sulfates, alkylether sulfates, alkyl sulfonates, alkylether sulfonates, alkylbenzene sulfonates, alkylbenzene ether sulfates, alkylsulfoacetates, secondary alkane sulfonates, secondary alkylsulfates, and the like. Many of these can be represented by the formulas:

$$R^{14}\text{—}(OCH_2CH_2)_n(OCH(CH_3)CH_2)_p\text{-}(Ph)_a\text{-}(OCH_2CH_2)_m\text{—}(O)_b\text{—}SO_3^-M^+$$

and

wherein: a and b=0 or 1; n, p, and m=0-100 (preferably 0-20, and more preferably 0-10); $R^{14}$ is defined as above provided at least one $R^{14}$ or $R^{15}$ is at least C8; $R^1$ is a (C1-C12)alkyl group (saturated straight, branched, or cyclic group) that may be optionally substituted by N, O, or S atoms or hydroxyl, carboxyl, amide, or amine groups; Ph=phenyl; and M is a cationic counterion such as H, Na, K, Li, ammonium, or a protonated tertiary amine such as triethanolamine or a quaternary ammonium group.

In the formula above, the ethylene oxide groups (i.e., the "n" and "m" groups) and propylene oxide groups (i.e., the "p" groups) can occur in reverse order as well as in a random, sequential, or block arrangement. Preferably for this class, $R^{14}$ includes an alkylamide group such as $R^{16}$—C(O)N(CH_3)CH_2CH_2— as well as ester groups such as —OC(O)—CH_2— wherein $R^{16}$ is a (C8-C22)alkyl group (branched, straight, or cyclic group). Examples include, but are not limited to: alkyl ether sulfonates such as lauryl ether sulfates such as POLYSTEP B12 (n=3-4, M=sodium) and B22 (n=12, M=ammonium) available from Stepan Company, Northfield, Ill. and sodium methyl taurate (available under the trade designation NIKKOL CMT30 from Nikko Chemicals Co., Tokyo, Japan); secondary alkane sulfonates such as Hostapur SAS which is a Sodium (C14-C17) secondary alkane sulfonates (alpha-olefin sulfonates) available from Clariant Corp., Charlotte, N.C.); methyl-2-sulfoalkyl esters such as sodium methyl-2-sulfo(C12-16)ester and disodium 2-sulfo(C12-C16) fatty acid available from Stepan Company under the trade designation ALPHASTEP PC-48; alkylsulfoacetates and alkylsulfosuccinates available as sodium laurylsulfoacetate (under the trade designation LANTHANOL LAL) and disodiumlaurethsulfosuccinate (STEPANMILD SL3), both from Stepan Company; alkylsulfates such as ammoniumlauryl sulfate commercially available under the trade designation STEPANOL AM from Stepan Company; dialkylsulfosuccinates such as dioctylsodiumsulfosuccinate available as Aerosol OT from Cytec Industries. Hydrotropes such as DOWFAX hydrotrope from Dow chemical or other diphenyl oxide surfactants may also be used.

2. Phosphates and Phosphonates. Suitable anionic surfactants also include phosphates such as alkyl phosphates, alkylether phosphates, aralkylphosphates, and aralkylether phosphates. Many may be represented by the formula:

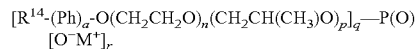

wherein: Ph, $R^4$, a, n, p, and M are defined above; r is 0-2; and q=1-3; with the proviso that when q=1, r=2, and when q=2, r=1, and when q=3, r=0. As above, the ethylene oxide groups (i.e., the "n" groups) and propylene oxide groups (i.e., the "p" groups) can occur in reverse order as well as in a random, sequential, or block arrangement. Examples include a mixture of mono-, di- and tri-(alkyltetraglycolether)-o-phosphoric acid esters generally referred to as trilaureth-4-phosphate commercially available under the trade designation HOSTAPHAT 340KL from Clariant Corp., as well as PPG-5 ceteth 10 phosphate available under the trade designation CRODAPHOS SG from Croda Inc., Parsipanny, N.J., and mixtures thereof.

Amphoteric Surfactants

Surfactants of the amphoteric type include surfactants having tertiary amine groups, which may be protonated, as well as quaternary amine containing zwitterionic surfactants. Those that have been particularly useful include:

1. Ammonium Carboxylate Amphoterics. This class of surfactants can be represented by the following formula:

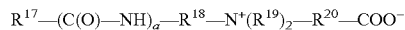

wherein: a=0 or 1; $R^{17}$ is a (C7-C21)alkyl group (saturated straight, branched, or cyclic group), a (C6-C22)aryl group, or a (C6-C22)aralkyl or alkaryl group (saturated straight, branched, or cyclic alkyl group), wherein $R^{17}$ may be optionally substituted with one or more N, O, or S atoms, or one or more hydroxyl, carboxyl, amide, or amine groups; $R^{19}$ is H or a (C1-C8)alkyl group (saturated straight, branched, or cyclic group), wherein $R^{19}$ may be optionally substituted with one or more N, O, or S atoms, or one or more hydroxyl, carboxyl, amine groups, a (C6-C9)aryl group, or a (C6-C9)aralkyl or alkaryl group; and $R^{18}$ and $R^{20}$ are each independently a (C1-C10)alkylene group that may be the same or different and may be optionally substituted with one or more N, O, or S atoms, or one or more hydroxyl or amine groups.

More preferably, in the formula above, $R^{17}$ is a (C1-C18) alkyl group, $R^{19}$ is a (C1-C2)alkyl group preferably substituted with a methyl or benzyl group and most preferably with a methyl group. When $R^{19}$ is H it is understood that the surfactant at higher pH values could exist as a tertiary amine with a cationic counterion such as Na, K, Li, or a quaternary amine group.

Examples of such amphoteric surfactants include, but are not limited to: certain betaines such as cocobetaine and cocamidopropyl betaine (commercially available under the trade designations MACKAM CB-35 and MACKAM L from McIntyre Group Ltd., University Park, Ill.); monoacetates such as sodium lauroamphoacetate; diacetates such as disodium lauroamphoacetate; amino- and alkylamino-propionates such as lauraminopropionic acid (commercially available under the trade designations MACKAM 1L, MACKAM 2L, and MACKAM 151L, respectively, from McIntyre Group Ltd.).

2. Ammonium Sulfonate Amphoterics. This class of amphoteric surfactants are often referred to as "sultaines" or "sulfobetaines" and can be represented by the following formula

wherein $R^{17}$-$R^{20}$ and "a" are defined above. Examples include cocamidopropylhydroxysultaine (commercially available as MACKAM 50-SB from McIntyre Group Ltd.). The sulfoamphoterics may be preferred over the carboxylate amphoterics since the sulfonate group will remain ionized at much lower pH values.

Nonionic Surfactants

Exemplary nonionic surfactants include, but are not limited to, alkyl glucosides, alkyl polyglucosides, polyhydroxy fatty acid amides, sucrose esters, esters of fatty acids and polyhydric alcohols, fatty acid alkanolamides, ethoxylated fatty acids, ethoxylated aliphatic acids, ethoxylated fatty alcohols (e.g., octyl phenoxy polyethoxyethanol available under the trade name TRITON X-100 and nonyl phenoxy poly(ethyleneoxy)ethanol available under the trade name NONIDET P-40, both from Sigma, St. Louis, Mo.), ethoxylated and/or propoxylated aliphatic alcohols (e.g., that available under the trade name PLURONIC F127 from Sigma), ethoxylated glycerides, ethoxylated block copolymers with ethylene diaminetetraacetic acid (EDTA), ethoxylated cyclic ether adducts, ethoxylated amide and imidazoline adducts, ethoxylated amine adducts, ethoxylated mercaptan adducts, ethoxylated condensates with alkyl phenols, ethoxylated nitrogen-based hydrophobes, ethoxylated polyoxypropylenes, polymeric silicones, fluorinated surfactants (e.g., those available under the trade names FLUORAD-FS 300 from 3M Co., St. Paul, Minn., and ZONYL from Dupont de Nemours Co., Wilmington, Del.), and polymerizable (reactive) surfactants (e.g., SAM 211 (alkylene polyalkoxy sulfate) surfactant available under the trade name MAZON from PPG Industries, Inc., Pittsburgh, Pa.). In certain preferred embodiments, the nonionic surfactants useful in the compositions of the present invention are selected from the group consisting of Poloxamers such as PLURONIC from BASF, sorbitan fatty acid esters, and mixtures thereof.

Hydrophilic Component

Compositions of the present invention can include a hydrophilic or water-soluble component to help solubilize and/or physically stabilize the enhancer component in the composition and/or to enhance the antimicrobial efficacy and/or the speed of antimicrobial efficacy. Incorporation of a sufficient amount of hydrophilic component in hydrophobic ointments can increase the antimicrobial activity both in terms of speed of kill and extent of kill. While not intended to be bound by theory, the incorporation of the hydrophilic component may allow more of the antimicrobial component to be available at the surface or to more rapidly diffuse to the surface of the ointment during use.

In general, the ratio of total hydrophilic component to total hydrophobic component (water insoluble ingredients) is at least 5:95 weight ratio (wt/wt), preferably at least 10:90 wt/wt, more preferably at least 15:85 wt/wt, and even more preferably at least 20:80 wt/wt. Levels as high as 30:70, 40:60, and 50:50 wt/wt of total hydrophilic component to total hydrophobic component (water insoluble ingredients) or higher may be appropriate for certain compositions.

Certain compositions may be solutions, emulsions (one liquid/gel/paste dispersed in another liquid/gel/paste), dispersions (solid in liquid/paste/gel), or combinations thereof.

A hydrophilic material is typically a compound that has a solubility in water of at least 7 wt-%, preferably at least 10 wt-%, more preferably at least 20 wt-%, even more preferably at least 25 wt-%, and even more preferably at least 40 wt-%, at 23° C. Most preferably, a hydrophilic component is infinitely miscible with water at 23° C.

Exemplary hydrophilic components include, but are not limited to, water, polyhydric alcohols, lower alkyl ethers (i.e., having a sufficiently small number of carbon atoms to meet the solubility limit above), N-methylpyrrolidone, alkyl esters (i.e., having a sufficiently small number of carbon atoms to meet the solubility limit above), and the lower monohydroxy alcohols discussed above as enhancers, as well as combinations thereof. Thus, a lower monohydroxy alcohol can function as both a hydrophilic compound and an enhancer. Preferably, the hydrophilic components include polyhydric alcohols, lower alkyl ethers, and water soluble or water dispersible esters. The water soluble or water dispersible esters are typically but not always short chain (i.e., C2-C6) alkyl esters of monofunctional and polyhydric alcohols. More preferably, the hydrophilic components include polyhydric alcohols.

Suitable polyhydric alcohols (i.e., organic compounds having more than one hydroxyl group) have a molecular weight of less than 500, preferably less than 400, and more preferably less than 200. Examples of polyhydric alcohols include, but are not limited to, glycerol, propylene glycol, dipropylene glycol, tripropylene glycol, polypropylene glycol, polyethylene glycol, diethylene glycol, pentaerythritol, trimethylolpropane, trimethylolethane, trimethylolbutane, sorbitol, mannitol, xylitol, pantothenol, ethylene glycol adducts of polyhydric alcohol, propylene oxide adducts of polyhydric alcohol, 1,3-butanediol, dipropylene glycol, diglycerine, polyglycerine, erythritol, sorbitan, sugars (e.g., sucrose, glucose, fructose, mannose, xylose, saccharose, trehalose), sugar alcohols, and the like. Certain preferred polyhydric alcohols include glycols (i.e., those containing two hydroxyl groups), glycerin, and propylene glycol. Certain other preferred polyhydric alcohols include sucrose, xylitol, mannitol, and sorbitol.

Ethers include materials such as dimethylisosorbide, polyethylene glycol and methoxypolyethylene glycols, block and random copolymers of ethylene oxide and propylene oxide, and laureth-4. Alkyl esters include triacetin, methyl acetate, methyl lactate, ethyl lactate esters, esters of polyethoxylated glycols, and combinations thereof.

In certain preferred embodiments, the hydrophilic components useful in the compositions of the present invention include those selected from the group consisting of polyhydric alcohols, and in particular glycerin and propylene glycol, and mixtures thereof. Most preferably, the hydrophilic component is selected to match the polyhydric alcohol portion of any fatty acid monoester of a polyhydric alcohol antimicrobial present. For example, if the antimicrobial agent was glycerolmonolaurate (monolaurin) the most preferred hydrophilic component is glycerin. In this manner, any transesterification reaction that may occur with the carrier solvent does not produce an undesirable by-product. If there are other components in the composition that may esterify with hydroxylfunctional hydrophilic components, conditions are selected to minimize this occurrence. For example, the components are not heated together for extended periods of time, and/or the pH is close to neutral if possible, etc.

One or more hydrophilic materials may be used in the compositions of the present invention at a suitable level to produce the desired result. In certain preferred embodiments that also include the hydrophobic component as the primary component (i.e., the component used in the greatest amount and referred to as a "vehicle"), the hydrophilic component is present in a total amount of at least 0.1%, preferably at least 1 wt-%, more preferably at least 4 wt-%, and even more preferably at least 8 wt-%, based on the weight of the ready to use composition. In certain embodiments, for example, when faster rate of kill is desired, higher levels of hydrophilic component may be employed. In these cases the hydrophilic component is present in a total amount of at least 10 wt-%, more preferably at least 20 wt-%, and even more preferably at least 25 wt-%.

In a preferred embodiment, the hydrophilic component is present in a total amount of no greater than 70 wt-%, preferably no greater than 60 wt-%, more preferably no greater than 40 wt-%, and even more preferably no greater than 30 wt-%, based on the ready to use composition. When the hydrophilic component is present in the greatest amount it is referred to as a "vehicle."

For certain applications, it may be desirable to formulate the antimicrobial in compositions including a hydrophilic component vehicle that is thickened with soluble, swellable, or insoluble organic polymeric thickeners or inorganic thickeners such as silica, fumed silica, precipitated silica, silica aerogel and carbon black, and the like; other particle fillers such as calcium carbonate, magnesium carbonate, kaolin, talc, titanium dioxide, aluminum silicate, diatomaceous earth, ferric oxide and zinc oxide, clays, and the like; ceramic microspheres or glass microbubbles; ceramic microspheres suc as those available under the tradenames ZEOSPHERES or Z-LIGHT from 3M Company, St. Paul, Minn. The above fillers can be used alone or in combination.

If water is used in certain embodiments, it is preferably present in an amount of less than 20%, preferably less than 10 wt-%, more preferably less than 5 wt-%, and even more preferably less than 2 wt-%, based on the ready to use composition. This helps the chemical stability of the compositions and may reduce irritation. For certain other embodiments, water can be used in a much greater amount, and can even be the primary component, as long as the composition is highly viscous. Preferably, such highly viscous compositions have a viscosity of at least 500 centipoise (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). The viscosity can be measured as described below in the Viscosity Test. Most preferred compositions meet these viscosity values even after heating to 32° C. or even 35° C. or as high as 37° C. to ensure when in contact with mammalian tissue the compositions remain substantive.

In some embodiments of the present invention, the compositions have a viscosity of at least 20 cps, preferably at least 100 cps, when measured by the Viscosity Test described herein. Higher viscosities are preferred to reduce migration as well as to provide substantivity (resistance to removal by fluids) to ensure long-term antimicrobial activity.

Hydrophobic Component

Certain preferred compositions of the present invention also include one or more hydrophobic materials. In certain embodiments, the hydrophobic component can be the same as the antimicrobial component, e.g., an antimicrobial lipid component. A hydrophobic material is typically an organic compound, which at 23° C. is a liquid, gelatinous, semisolid or solid and has a solubility in water of less than 5% by weight, preferably less than 1% by weight, more preferably less than 0.5% by weight, and even more preferably less than 0.1% by weight. These materials include compounds typically considered emollients in the cosmetic art.

Examples of general emollients include, but are not limited to, short chain (i.e., C1-C6)alkyl or (C6-C12)aryl esters of long (i.e., C8-C36) straight or branched chain alkyl or alkenyl alcohols or acids and polyethoxylated derivatives of the alcohols; short chain (i.e., C1-C6)alkyl or (C6-C12) aryl esters of (C4-C12)diacids or (C4-C12)diols optionally substituted in available positions by —OH; (C2-C18)alkyl or (C6-C12)aryl esters of glycerol, pentaerythritol, ethylene glycol, propylene glycol, as well as polyethoxylated derivatives of these; (C12-C22)alkyl esters or (C12-C22)ethers of polypropylene glycol; (C12-C22)alkyl esters or (C12-C22) ethers of polypropylene glycol/polyethylene glycol copolymer; and polyether polysiloxane copolymers.

Additional examples of hydrophobic components include cyclic dimethicones, including volatile cyclic silicones such as D3 and D4, polydialkylsiloxanes, polyaryl/alkylsiloxanes, silicone copolyols, long chain (i.e., C8-C36)alkyl and alkenyl esters of long (i.e., C8-C18) straight or branched chain alkyl or alkenyl alcohols or acids, long chain (i.e., C8-C36)alkyl and alkenyl amides of long straight or branched chain (i.e., C8-C36)alkyl or alkenyl amines or acids; hydrocarbons including straight and branched chain alkanes and alkenes such as isoparafins (e.g., isooctane, isododecane, isooctadecane, etc.), squalene, and mineral oil, polysiloxane polyalkylene copolymers, dialkoxy dimethyl polysiloxanes; (C12-C22)alkyl and (C12-C22)alkenyl alcohols, and petroleum derived alkanes such as isoparafins, petrolatum, petrolatum USP, as well as refined natural oils (especially NF or USP grades) such as olive oil NF, cotton seed oil, peanut oil, corn oil, castor oil, sesame oil, safflower oil, soybean oil, and the like, and blends thereof. In certain preferred embodiments, the hydrophobic components useful in the compositions of the present invention include those selected from the group consisting of petrolatum USP and short chain (i.e., C1-C6)alkyl or (C6-C12)aryl esters of long (i.e., C8-C36) straight or branched chain alkyl or alkenyl alcohols or acids and polyethoxylated derivatives of the alcohols; short chain (i.e., C1-C6)alkyl or (C6-C12)aryl esters of (C4-C12)diacids or (C4-C12)diols optionally substituted in available positions by —OH (such as diisopropyladipate, diisopropylsebacate); (C1-C9)alkyl or (C6-C12) aryl esters of glycerol, pentaerythritol, ethylene glycol, propylene glycol (such as glyceryl tricaprylate/caprate); and mixtures thereof. Other useful emollients include (C12-C15) alkyl esters of benzoic acid, fatty alcohols such as stearyl or cetyl alcohol, and lanolin USP or lanolin derivatives. For certain particularly preferred embodiments, the hydrophobic component is petrolatum.

One or more hydrophobic materials may be used in the compositions of the present invention at a suitable level to produce the desired result. In a preferred embodiment (in which the compositions include very little or no water), the hydrophobic component is present in a total amount of at least 50 wt-%, more preferably at least 70 wt-%, and even more preferably at least 80 wt-%, based on the ready to use composition. In a preferred embodiment, the hydrophobic component is present in a total amount of no greater than 99 wt-%, more preferably no greater than 95 wt-%, and even more preferably no greater than 92 wt-%, based on the ready to use composition. When the hydrophobic component is present in the greatest amount it is referred to as a "vehicle." In those formulations where the hydrophobic component(s) and the hydrophilic component(s) are present at the same concentrations, the continuous phase is considered the "vehicle."

Penetration Agents

A penetration agent may also be used to facilitate the diffusion of the composition in whole or in part, but preferably diffusion of at least the antimicrobial component (and optionally any enhancer, secondary active, or surfactant, if present) into or through tissue in order to kill or inactivate microorganisms and reduce inflammation in affected tissues. A penetration agent is an agent used to increase the permeability of the tissue to the antimicrobial component and pharmacologically active agent, if present, to increase the rate at which the antimicrobial and/or secondary active agent diffuses into the affected or adjacent tissues.

Preferably, the antimicrobial component is able to diffuse into any fluid associated with the condition to be treated and kill or inactivate the microorganisms. Furthermore, preferably the antimicrobial component and/or surfactant component are able to reduce the surface tension of the fluid to facilitate kill and expulsion of the fluid from the affected site, e.g., to spread and kill microorganisms between the uretral wall and a catheter and to facilitate drainage of any fluid that may build up extraluminally. A penetration agent may increases permeability by reversibly damaging or by altering the physiochemical nature of the treated tissue to reduce its diffusional resistance.

Preferred penetration agents are non-toxic, nonirritating, non-sensitizing and non-comedogenic, readily emulsifiable in water, good solvents to solubilize the formulation components such as the antimicrobial, enhancer, and surfactant components (if present), has a high positive spreading coefficient, is a good wetting agent for dry and wet tissue and is stable to hydrolysis within pH range of about 3-8. Preferred penetration agents are water insoluble. The penetration enhancing component may be used in concentrations of 0-99%. In some preferred embodiments the penetration agent is the vehicle.

Examples of penetration agents include without limitation: alcohols such as ethanol and isopropanol; polyols such as n-alkanols, limonene, terpenes, dioxolane; glycols such as propylene glycol, dipropyelne glycol, butylenes glycol, and glycerol; sulfoxides such as dimethylsulfoxide (DMSO) and methyl dodecyl sulfoxide; amides such as dimethylformamide and dimethylacetamide; ketones; oleates such as triolein and polyethylene glycol oleates such as PEG-5 oleate; various alkanoic acids such as caprylic acid; lactam compounds such as azone and N-methylpyrrolidone; alkanols such as oleyl alcohol and polyethoxylated oleyl alcohol; dialkylamino acetates, and admixtures thereof. The use of such penetration agents is disclosed, for example, in U.S. Pat. No. 6,093,417. Preferred delivery enhancing components include lauryl alcohol, lauramide DEA, lauryl pyrrolidone-5-carboxylate (e.g., Laurydone); ascorbyl palmitate; glycerol; tetraglycol (alpha-[(tetrahydro-2-furanyl)methyl]-omega-hydroxy-poly(oxy-1,2-ethanediyl)), lauryl glycol (i.e., 1,2-dodecanediol), and mixtures thereof.

Particularly preferred penetration agents are alkyl esters, aralkyl esters, and alkaryl esters such as short chain alkyl or aryl esters (C1-C6) of long chain straight or branched chain alkyl or alkenyl alcohols or acids (C8-C36) and their polyethoxylated derivatives (a particularly preferred subclass are benzoic acid esters of alkyl alcohols such as (C12-C15)alkyl benzoate which is commercially available as FINSOLV, Finetex Inc., Elmwood Park, N.J.); short chain alkyl or aryl esters (C1-C6) of (C4-C12)diacids or diols optionally substituted in available positions by —OH; alkyl or aryl (C1-C9)esters of glycerol, pentaerythritol, ethylene glycol, propylene glycol, as well as polyethoxylated derivatives of these and polyethylene glycol; (C12-C22)alkyl esters or ethers of polypropylene glycol; (C12-C22)alkyl esters or ethers of polypropylene glycol/polyethylene glycol copolymer; and polyether polysiloxane copolymers.

It is noted that many of the surfactants disclosed herein may also significantly improve penetration of the antimicrobial composition or its components. For example, many sulfonated surfactants are well known to disrupt the stratum corneum and help enhance penetration of active ingredients into and through skin. For the purposes of this invention these components are still considered surfactants. Compositions that include a surfactant may not require an addition penetration agent. Similarly some some of the hydrophobic and/or hydrophilic components disclosed herein may also significantly improve penetration of the antimicrobial composition or its components.

It is also noted that many of the antimicrobial lipids are themselves amphipathic and may improve penetration into the treated tissue. Therefore, compositions high in the antimicrobial lipid may not require an additional penetration agent.

In addition, the penetration agent may help the antimicrobial component to penetrate into a polymeric surface of a device.

Optional Additives

Compositions of the present invention may additionally employ adjunct components conventionally found in pharmaceutical compositions in their art-established fashion and at their art-established levels. Thus, for example, the compositions may contain additional compatible pharmaceutically active materials for combination therapy (such as supplementary antimicrobials, anti-parasitic agents, antipruritics, astringents, local anaesthetics, steroids, non-steroidal anti-inflammatory agents, or other anti-inflammatory agents), or may contain materials useful in physically formulating various dosage forms of the present invention, such as excipients, dyes, perfumes, flavorants, taste masks, lubricants, thickening agents, stabilizers, preservatives, or antioxidants.

It will be appreciated by the skilled artisan that the levels or ranges selected for the required or optional components described herein will depend upon whether one is formulating a composition for direct use, or a concentrate for dilution prior to use, as well as the specific component selected, the ultimate end-use of the composition, and other factors well known to the skilled artisan.

It will also be appreciated that additional antiseptics (i.e., disinfectants), or antibiotics may be included and are contemplated. These include, for example, addition of metals such as silver, copper, zinc; iodine and iodophors; chlorhexidine and its various salts such as chlorhexidine digluconate; polyhexamethylenebiguanide, parachlorometaxylenol, triclosan, antimicrobial quaternary amines including polymeric quaternary amines, "azole" antifungal agents including clotrimazole, miconazole, econazole, ketoconazole, and salts thereof; and the like. Antibiotics such as neomycin sulfate, bacitracin, mupirocin, polymyxin, rifampin, tetracycline, and the like, also may be included. Preferred compositions, however, are free of antibiotics due to the chance of resistance formation.

Formulations and Methods of Preparation

Many of the compositions of the present invention have exceptional broad spectrum antimicrobial activity and thus are generally not terminally sterilized but if necessary may be sterilized by a variety of industry standard techniques. For example, it may be preferred to sterilize the compositions in their final packaged form using electron beam. It may also be possible to sterilize the sample by gamma radiation or heat. Other forms of sterilization may be acceptable. It may also be suitable to include preservatives in the formulation to prevent growth of certain organisms. Suitable preservatives include industry standard compounds such as Parabens (methyl, ethyl, propyl, isopropyl, isobutyl, etc.), 2-bromo-2-nitro-1,3-diol; 5-bromo-5-nitro-1,3-dioxane, chlorobutanol, diazolidinyl urea; iodopropylnyl butylcarbamate, phenoxyethanol, halogenated cresols, methylchloroisothiazolinone, and the like, as well as combinations of these compounds.

The compositions of the present invention preferably adhere well to mammalian tissues (particularly, skin, mucosal tissue, and wounds), in order to deliver the antimicrobial to the intended site over a prolonged period even in the presence of perspiration, drainage (e.g., mucosal secretions), or mild lavage. The compositions are typically non-aqueous, although high viscosity compositions can include a large amount of water. The component in the greatest amount (i.e., the vehicle) in the formulations of the invention may be any conventional vehicle commonly used for topical treatment of human or animal skin. The formulations are typically selected from one of the following three types: (1) anhydrous or nearly anhydrous formulations with a hydrophobic vehicle (i.e., the hydrophobic component, which can include one or more hydrophobic compounds, is present in the greatest amount); (2) anhydrous or nearly anhydrous formulations with a hydrophilic vehicle (i.e., the hydrophilic component, which can include one or more hydrophilic compounds, is present in the greatest amount); and (3) highly viscous water-based formulations. These are discussed below.

(1) Anhydrous or Nearly Anhydrous Formulations with a Hydrophobic Vehicle. In certain preferred embodiments of the present invention, the compositions include an antimicrobial component in a hydrophobic vehicle in combination with surfactant(s), an enhancer component, and a small amount of a hydrophilic component. In most instances the enhancers are not soluble in the hydrophobic component at room temperature although they may be at elevated temperatures. The hydrophilic component is generally present in a sufficient amount to stabilize (preferably to solubilize) the enhancer(s) in the composition. For example, when formulating with organic acid enhancers or certain solid surfactants in petrolatum many enhancers and surfactants will dissolve into the petrolatum at temperatures above 85° C.; however, upon cooling, the enhancer and/or surfactant crystals or precipitates back out of solution making it difficult to produce a uniform formulation. If at least 0.1 wt-%, and preferably at least 1.0 wt-%, more preferably at least 5 wt-%, and most preferably at least 10 wt-%, of a hydrophilic compound (e.g., a glycol) is added, a stable formulation can be obtained. It is believed that these formulations produce an emulsion in which the enhancer and/or surfactant is dissolved, emulsified, or dispersed in the hydrophilic component which is emulsified into the hydrophobic component(s). These compositions are stable upon cooling and centrifuging.

The hydrophilic component also helps to stabilize many of the surfactants used in preferred formulations. For example, dioctylsulfosuccinate sodium salt (DOSS) dissolves in glycerin at elevated temperatures and helps keep the DOSS physically stable in the composition. Furthermore, it is believed that incorporation of the hydrophilic component in the formulation improves the antimicrobial activity. The mechanism for this is unknown; however, it may speed the release of the enhancer component and/or the antimicrobial component.

The water content of these formulations is preferably less than 20%, preferably less than 10 wt-%, more preferably less than 5 wt-%, and even more preferably less than 2 wt-%, in order to minimize hydrolysis of any ester based antimicrobial present.

Furthermore, it has been found that it is particularly desirable where the antimicrobial component includes an ester to use the hydroxyacid component on which the antimicrobial component is based as the enhancer and/or hydrophilic component, e.g., a composition comprising 2-ethylhexyl lactate may use lactic acid as the enhancer and/or the hydrophilic component. In this manner, transesterification of the antimicrobial ester with the hydroxy acid compound will not result in additional chemical species present.

These formulations can be relatively easily manufactured by first heating the hydrophobic component to 85° C., adding in the surfactant, hydrophilic component, and enhancer component, cooling to 65° C., and adding the antimicrobial component above its melting point. Alternatively, the enhancer component can be predissolved in the hydrophilic component (optionally along with the surfactant) and added to the hydrophobic component either before or after addition of the antimicrobial component. If either the antimicrobial component or the hydrophobic component are solids at room temperature this is done at the minimum temperature necessary to melt all components. Exposure of ester containing antimicrobial to enhancers and/or hydrophilic components that include either acid or ether groups to elevated temperatures for extended periods of time should be avoided to prevent transesterification reactions.

Thus, the present invention provides methods of manufacture. One preferred method involves: dissolving the enhancer component in the hydrophilic component; combining the hydrophobic vehicle and the hydrophilic component with the enhancer component dissolved therein with mixing to form a mixture; optionally heating the hydrophobic vehicle to a temperature sufficient to form a pourable liquid (which for many hydrophobic vehicles this is above its melting point) before or after combining it with the hydrophilic component and enhancer component; adding the antimicrobial component to the mixture; and cooling the mixture before or after adding the antimicrobial component.

The hydrophilic component may or may not be present in the formulations that include a hydrophobic vehicle. Thus, another preferred method of manufacture involves: combining the enhancer component and the hydrophobic vehicle with mixing to form a mixture; optionally heating the hydrophobic vehicle to a temperature sufficient to form a pourable liquid (which for many hydrophobic vehicles is above its melting point) before or after combining it with the enhancer component; adding the antimicrobial component to the mixture with mixing; and cooling the mixture before or after adding the antimicrobial component.

Surprisingly, it has been found that these compositions are significantly less irritating than formulations using completely hydrophilic components. In blind human trials participants were asked to instill 0.5 gram (g) of ointments based on hydrophobic components (e.g., petrolatum) that include an AHA enhancer, surfactant, and 10% hydrophilic component (e.g., glycerin) as well as ointments based on hydrophilic components (e.g., PEG 400/PEG 1450) using the same enhancer and surfactant. Surprisingly, the ointments based on the hydrophobic component were preferred by 100% of the participants.

The viscosity of these formulations intended for use on skin or in the anterior nares is preferably relatively high to prevent excessive drainage off the treatment site. In this regard the viscosity is preferably at least 500 Centipoise (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). The viscosity can be measured as described below in the Viscosity Test.

Most preferably, the formulations intended for use on skin, anterior nares, or where drainage would be a concern are essentially gelatinous at room temperature, having a significant yield point such that they do not flow readily at temperatures below 35° C. The viscosity is measured using the viscosity test described herein. Certain gelatinous vehicles may also have a characteristic temperature at which they "melt" or begin to dramatically lose viscosity. Preferably this is higher than body temperature also to ensure that excess drainage of the composition of the treatment site does not occur. Therefore, the melting point of the composition is preferably greater than 32° C., more preferably greater than 35° C., and even more preferably greater than 37° C. The melting point is taken as the lowest temperature at which the viscosity becomes dramatically less or is equal to or less than 100,000 cps.

Similarly the viscosity and/or melt temperature can be enhanced by either incorporating a crystalline or semicrystalline hydrophobic carrier such as a higher melting petrolatum, addition of an insoluble filler/thixotrope, or by addition of a polymeric thickener (e.g., a polyethylene wax in a petrolatum vehicle). Polymeric thickeners may be linear, branched, or slightly crosslinked. It is important for comfort that the formulations are relatively soft and that they spread easily to allow easy application, especially over a wound, rash, or infected area or in the anterior nares. A particularly preferred vehicle for use on skin, in the anterior nares, or in other areas where high viscosity is desirable is white petrolatum USP having a melting point greater than 40° C.

(2) Water in Oil Emulsions. Antimicrobial components of this invention can be formulated into water-in-oil emulsions in combination with enhancer(s) and surfactant(s). Particularly preferred compositions comprise at least 35%, preferably at least 40%, more preferably at least 45%, and most preferably at least 50%, by weight oil phase. As used herein the oil phase includes all components which are either not soluble in water or preferentially soluble in the oil(s) present at 23° C. One method of preparing these emulsions is described in International Publication No. WO 2003/028767. Generally speaking, the hydrophobic component (oil) is mixed in Container A along with any emulsifier(s) optionally including polymeric emulsifiers and heated to a temperature sufficient to ensure a homogenous composition and subsequent stable emulsion. The temperature is typically raised to at least 60° C., preferably to at least 80° C., and more preferably to 100° C. or more. In a separate Container B, the hydrophilic ingredients are mixed, including one or more of the following: water, hydrophilic component, enhancer(s), surfactant(s), and acids/bases to adjust the pH of the final composition. The contents of container B are heated to a temperature sufficient to ensure a stable final emulsion composition without significantly degrading any of the components, typically to a temperature greater than 40° C., preferably greater than 50° C., and more preferably greater than 60° C. While hot, container B is added to container A using a high shear mixer. The composition may be continuously mixed until cool (e.g., to a temperature of less than 40° C.) or it can be allowed to sit as long as the contents remain uniformly mixed. If the antimicrobial is heat sensitive, it is added with mixing during the cooling down period. If it is not heat sensitive, it may be added to either container A or container B. The viscosity of these compositions may be adjusted by altering the levels of emulsifier; changing the ratio of water to oil phase; selection of the oil phase (e.g., select from an oil (hydrophobic component), which is more or less viscous); incorporation of a polymeric or particulate thickener, etc.

(3) Hydrophilic Vehicle. Antimicrobial components of this invention can be formulated into a hydrophilic component such as that based on the hydrophilic compounds (discussed above) optionally in combination with the enhancer(s) and surfactant(s). Particularly preferred are polyethylene glycols (PEGs), including blends of different molecular weight PEGs, optionally containing one or more glycols. When using a hydrophilic component as the vehicle (i.e., the component used in the greatest amount, which can include one or more hydrophilic compounds), it should be preferably selected to maintain viscosity and melt temperature characteristics similar to those stated above for the anhydrous or nearly anhydrous formulations using a hydrophobic vehicle.

Similarly the viscosity can be enhanced by either incorporating a crystalline or semicrystalline hydrophilic compound such as a PEG of sufficient molecular weight, addition of an insoluble filler/thixotrope, or by addition of a polymeric thickener. Polymeric thickeners may be linear, branched, or slightly crosslinked. It is desirable for comfort that the formulations are relatively soft and that they spread easily to allow easy application, especially in the anterior nares or over a wound, rash, or infected area. For this reason, a particularly preferred vehicle is based on a blend of a liquid or semisolid PEG (PEG 400-1000) with a more crystalline PEG (PEG 1000-2000). Particularly preferred is a blend of PEG 400 with PEG 1450 in a ratio of 4:1.

In certain preferred embodiments of the present invention, the compositions are in the form of a lotion, ointment, or cream. That is, the compositions are in the form of a relatively viscous state such that they are suitable for application to nasal passageways. Preferably, such compositions have a viscosity of at least 500 Centipoise (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). The viscosity can be measured as described below in the Viscosity Test. Preferred formulations have high viscosity even after application to mammalian tissue at 32-37° C.

(4) Water-based Formulations. Aqueous compositions of the present invention are those in which water is present in the greatest amount, thereby forming the "vehicle." For these systems it is particularly important that a relatively high viscosity be imparted to the composition to ensure that the antimicrobial composition is not rapidly dispersed off the afflicted area. These formulations also adhere well to tissue and thus deliver the antimicrobial to the intended site over a prolonged period even in the presence of perspiration, drainage (e.g., mucosal secretions), or mild lavage. Such a high viscosity can be imparted by a thickener system. The thickener system of the invention is compatible with the antimicrobial composition described above in order to provide suitable antimicrobial efficacy, chemical and physical stability, acceptable cosmetic properties, and appropriate viscosity for retention in the afflicted area.

Preferably, compositions of this invention have a viscosity of at least 500 Centipoise (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). The viscosity can be measured as described below in the Viscosity Test. Preferred formulations have high viscosity even after application to mammalian tissue at 32-37° C. Because certain optional ingredients, such as enhancers, hydrophilic compounds, hydrophobic compounds, and the like, may effect the viscosity (either positively or negatively), the measured viscosity is that of the final composition.

Preferred thickener systems used in the compositions of the present invention are capable of producing viscoelastic compositions that are very stable. By varying the amount and type of thickener, the degree of elasticity can be adjusted from almost a purely viscous composition to a highly elastic and even gel-like composition. If emollients are added, increasing the elasticity and/or yield stress of the system imparts added stability to prevent separation of immiscible emollients. Excessive elasticity, however, is not preferred because an excessively elastic composition usually does not provide a cosmetically appealing product.

Significantly, thickener systems used in the present invention are capable of achieving high viscosities at relatively low total concentrations. The total concentration of the thickener system is preferably less than 8 wt-%, more preferably less than 5 wt-%, and most preferably less than 3 wt-%, based on the total weight of the ready to use composition. Preferably, the total concentration of the thickener system can be as little as 0.5 wt-%, based on the total weight of the composition. For certain embodiments, however, the total concentration of thickener system is greater than 1 wt-%, based on the total weight of the ready to use composition.

The thickener system can include organic polymers or inorganic thixotropes such as silica gel, clays (such as betonite, laponite, hectorite, montmorrillonite and the like), as well as organically modified inorganic particulates materials, and the like. As used herein, an organic polymer is considered part of the thickener system if its presence in the composition results in an increase in the viscosity of the composition. Certain polymers that do not have these characteristics may also be present in the composition but do not contribute significantly to the viscosity of the composition. For purposes of this invention, they are not considered part of the thickener system. For example, certain nonionic polymers such as lower molecular weight polyethylene glycols (e.g., those having a molecular weight of less than 20,000) do not increase the viscosity of the composition significantly. These are considered part of the hydrophilic component, for example, rather than part of the thickener system.

The thickener system can be prepared from one or more nonionic, cationic, anionic, zwitterionic, or associative polymers as long as they are compatible with the antimicrobial and enhancer components of the composition. For example, certain acidic enhancers such as those that include carboxylic acid groups are most effective in their protonated form. This requires that the composition has an acidic pH. For this reason, many anionic thickeners based on neutralized carboxylic acid groups would not be suitable. For example, Carbopol-type thickeners based on polyacrylic acid salts do not typically thicken well at pH values of less than 5 and certainly less than a pH of 4.5. Therefore, at lower pH values (i.e., when acidic enhancers are present) if the aqueous compositions are thickened with anionic polymers, the polymers are preferably based on sulfonic acid, sulfate, phosphonic acid, or phosphate groups. These polymers are able to thicken at much lower pH values due to the lower pKa of these acid groups. Preferred polymers of this class include ARISTOFLEX HMB (ammonium acryloyldimethyl-taurate/beheneth-25 methacrylate crosspolymer) and ARISTOFLEX ASV (ammonium acryloyldimethyltaurate/NVP copolymer) from Clariant Corporation. Other preferred sulfonic acid polymers are those described in U.S. Pat. No. 5,318,955.

Preferably, the compositions that include an acidic enhancer component are thickened using cationic or nonionic thickeners since these perform well at low pH. In addition, many of the nonionic and cationic polymers can tolerate higher levels of salts and other additives and still maintain high viscosity.

A preferred group of nonionic polymeric thickeners include modified celluloses, guar, xanthan gum, and other natural polymers such as polysaccharides and proteins, associative polymers based on nonionic ethylenically unsaturated monomers wherein at least one comonomer has at least 16 carbon atoms, and polymers based on ethylenically unsaturated monomers selected from the group consisting of acrylates, acrylamides, vinyl lactams, vinyl acetate and its hydrolyzed derivatives, methyl vinyl ethers, styrene, and acrylonitrile.

A preferred group of cationic polymeric thickeners include cationically modified celluloses, quaternized natural amino-functional polymers, and polymers based on ethylenically unsaturated monomers selected from the group consisting of acrylates, acrylamides, vinyl lactams, vinyl acetates, methyl vinyl ethers, styrene, and acrylonitrile.

Cationic polymers for use in the compositions of this invention can be selected from both permanently charged quaternary polymers (those polymers with quaternary amines such as Polyquaternium 4, 10, 24, 32, and 37, described below) as well as protonated primary, secondary, and tertiary amine functional polymers that have been protonated with a suitable protonic acid. Preferred protonated cationic polymers are based on tertiary amines. The protonated cationic polymers are preferably protonated with suitable acids that will not result in undue skin irritation. These include, for example, (C1-C10)alkylcarboxylic acids optionally substituted by oxygen (e.g., acetic acid, alpha-hydroxy acids such as lactic acid, gluconic acid, benzoic acid, mandelic acid, and the like), (C1-C10)alkylsulfonic acids (e.g., methylsulfonic acid and ethylsulfonic acid), (C1-C10)alkylhydrogensulfates (e.g., methylhydrogensulfate) and mineral acids (e.g., hydrochloric acid, hydrobromic acid, sulfuric acid, phosphoric acid, and the like).

The charge on protonated cationic polymers is pH dependent. For this reason, in order to ensure the polymer is sufficiently protonated, the pH is adjusted appropriately and should be in the range of preferably 2-9.5, more preferably 2-8, and most preferably 2.5-7.5. The pH of preferred compositions that include acidic enhancers should be lower and is typically 2-5, and preferably 2-4. It should be noted that it is not necessary to have all of the amines on a particular polymer protonated. The level of protonation will to a certain extent be pH dependent. With certain polymers in order to obtain optimum thickening with low skin irritation it may be beneficial to only protonate a small percentage of the available amine groups while with other polymers it may be beneficial to protonate substantially all of the amine groups. This will be easily determined by one skilled in the art.

The quaternary, tertiary, secondary, and primary amine functional polymers may be chosen from natural polymers, modified natural polymers, as well as synthetic polymers. These polymers may be soluble or swellable in the aqueous solvent. Furthermore, these polymers may also possess hydrophobic side chains and thus be associative polymers.

Polymers can be classified as soluble, swellable, or associative in the aqueous compositions. Some polymers may fall into one or more of these classes. For example, certain associative polymers can be soluble in the aqeuous system. Whether they are considered soluble, swellable, or associative in the aqueous system, suitable polymers for use in the compositions of the present invention may be film forming or not. Film forming polymers may retain the active antimicrobial component at the afflicted site for longer periods of time. This may be desirable for certain applications. For example, some film forming polymers may produce compositions that could not be easily washed off with water after being applied and dried.

As used herein, a soluble polymer is one that in dilute solution (i.e., 0.01-0.1 wt-% in the desired aqueous solvent system defined as containing water and any other hydrophilic compounds), after heating for a sufficient time to ensure solubilization of any potentially soluble components, has no significant observable particles of greater than 1 micron in particle size, as determined by light scattering measurements using, for example, Malvern Masterisizer E Laser Particle Size Analyzer available from Malvern Co., Boston, Mass.

As used herein, a swellable polymer is one that in dilute solution (i.e., 0.01-0.1 wt-% in the desired aqueous solvent system), after heating for a sufficient time to ensure solubilization of any potentially soluble components, has a significant (i.e., detectable) number of observable particles of greater than 1 micron in particle size, as determined by light scattering measurements using, for example, Malvern Masterisizer E Laser Particle Size Analyzer.

As used herein, an associative polymer is one that has greater than 2 hydrophobic chains per polymer molecule of greater than 16 carbon atoms. Examples of such polymers are as follows.

Soluble Polymers—Cationic Natural Polymer Derivatives. Cationic modified cellulosic polymers are reported in the literature to be soluble in water. Such polymers have been found to be useful in the present invention. The most preferred modified cellulose products are sold under the trade names CELQUAT (National Starch and Chemicals Corp., Bridgewater, N.J.) and UCARE (Amerchol Corporation, Edison, N.J.). CELQUAT is a copolymer of a polyethoxylated cellulose and dimethyldiallyl ammonium chloride and has the Cosmetic, Toiletry and Fragrance Association (CTFA) designation Polyquaternium-4.

An alkyl modified quaternary ammonium salt of hydroxyethyl cellulose and a trimethyl ammonium chloride substituted epoxide can also be used. The polymer conforms to the CTFA designation Polyquaternium 24 and is commercially available as QUATRISOFT LM-200 from Amerchol Corp., Edison, N.J.

A particularly suitable type of cationic polysaccharide polymer that can be used is a cationic guar gum derivative, such as guar hydroxypropyltrimonium chloride (Commercially available from Rhone-Poulenc under the trade designation JAGUAR).

Soluble Polymers—Cationic Synthetic Polymers. Synthetic cationic linear polymers useful in the present invention are preferably quite high in cationic charge density—generally having greater than 10 wt-% cationic monomer, preferably greater than 25 wt-%, and more preferably greater than 50 wt-%. This ensures a good cosmetic feel and may actually improve water solubility. In general, the polymers useful in the present invention have sufficient molecular weight to achieve thickening at generally less than 5 wt-% polymer, but not too high that the lotion/cream/ointment feels slimy and stringy. While the composition of the polymer will dramatically affect the molecular weight at which sufficient thickening will occur, the polymers preferably have a molecular weight of at least 250,000 daltons, and more preferably at least 500,000 daltons. The polymers preferably have a molecular weight of no greater than 3,000,000 daltons, and more preferably no greater than 1,000,000 daltons. The homopolymers are preferably prepared from methacryloyloxyalkyl trialkyl ammonium salt, acryloyloxyalkyl trialkyl ammonium salt, and/or quaternized dialkylaminoalkylacrylamidine salt. Preferably the polymers are copolymers of at least two monomers selected from the group consisting of trialkylaminoalkyl acrylate and methacrylate salts, dialkyldiallyl ammonium salts, acrylamidoalkyltrialkyl salts, methacrylamidoalkyltrialkyl salts, and alkyl imidazolinium salts, N-vinyl pyrrolidinone, N-vinyl caprolactam, methyl vinyl ether, acrylates, methacrylates, styrene, acrylonitrile, and combinations thereof. Typically, for the salts the counterions are preferably $F^-$, $Cl^-$, $Br^-$, and $CH_3(CH_2)_nSO_4^-$ where n=0-4.

A variety of quaternary copolymers of varying quaternization, can be synthesized based on homo or copolymers of amino acrylates with methyl, ethyl, or propyl side chains. These monomers could also be copolymerized with other nonionic monomers including quaternary acrylic homopolymers, such as homopolymers of 2-methacryloxyethyl trimethylammonium chloride and 2-methacryloxyethyl methyl diethyl ammonium bromide; and copolymers of quaternary acrylate monomers with a water-soluble monomers, such as Petrolite Product No. Q-0043, a proprietary copolymer of a linear quaternary acrylate and acrylamide at high molecular weight (4-5 million MW).

Another useful soluble cationic polymer is N,N-dimethylaminopropyl-N-acrylamidine (which is quaternized with diethylsulfate) bound to a block of polyacrylonitrile. This block copolymer is available under the trade designation Hypan QT-100 from Lipo Chemicals Inc., Paterson, N.J. It is quite effective at thickening aqueous systems and has a good cosmetic feel. This polymer as received, however, has an objectionable amine odor. The odor could probably be masked with the proper fragrance, but is preferably removed prior to formulation (e.g., with a solvent cleaning process) so that the formulation can be supplied without fragrance. Preferred compositions are free of fragrances and colorants.

Suitable cationic polymers include, for example, copolymers of 1-vinyl-2-pyrrolidine and 1-vinyl-3-methyl-imidazolium salt (e.g., chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate, referred to in the industry (CTFA) as Polyquaternium-11. This material is available commercially from ICI Corp., Wayne, N.J., under the trade designation GAFQUAT; cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively.

Soluble Polymers-Nonionic. A variety of cellulosic ethers are reported in the literature to be soluble in water. Materials in this class that are nonionic and have been shown to be useful include: methylhydroxypropylcellulose, available as BENECEL MP 943 from Aqualon, Wilmington, Del.; hydroxypropylcellulose, available as KLUCEL (LF, GF, MF, HF) from Aqualon; hydroxybutylmethylcellulose (3.5% hydroxybutyl and 30% methoxyl) from Scientific Polymer Products, Ontario, N.Y.; and hydroxyethylcelluloses, available under the trade designation NATROSOL from Aqualon. Xanthan gum, guar, locust bean gum, and other polysaccharides may also be suitable. These polymers may be produced from plant sources or can be produced through microbial cell culture. Polyvinyl alcohol (PVA) also may be suitable. For example, PVA made from polyvinyl acetate which has been hydrolyzed to 87% is highly water soluble at room temperature. Those with higher percent hydrolysis become progressively more crystalline and may need to be heated to get into solution. Protein thickeners such as gelatin and pectin may also be useful.

Amine oxide polymers such as those described in U.S. Pat. No. 6,123,933 (Hayama) and those commercially available under the trade designation DIAFORMER Z-711, Z-712, Z-731, and Z-751 from Clariant Corp. are useful. Additionally, zwitterionic polymers, such as methacryloyl ethyl betaine/acrylate copolymer that are commercially available under the trade designation DIAFORMER Z-400 from Clariant Corp. can also be used. Zwitterionic polymers described in U.S. Pat. No. 6,590,051 may also be useful.

Carboxylic acid functional polymers including naturally occurring carboxylic acid functional polymers such as hyaluronic acid and derivatives of natural polymers such as carboxymethylcellulose, alginic acid and other alginate polymers, Fucogel (a polysaccharide consisting of three mono-saccharides, fucose, galactose, and galacturonic acid), hyaluronic acid, and the like, also may be useful. Synthetic polymers may also be useful, such as those based on carboxylic acid, phosphonic acid, or sulfonic acid functional monomers, including but not limited to, polymers derived from acrylic acid, methacrylic acid, maleic anhydride, itaconic anhydride, sodium AMPS (the sodium salt of 2-acrylamido-2-methylpropane sulfonic acid), sulfopropyl acrylate or methacrylate, sulphomethylated acrylamide, allyl sulphonate, sodium vinyl sulphonate, combinations thereof, or other water-soluble forms of these or other polymerizable carboxylic or sulphonic acids.

Swellable Polymers. Many swellable polymers, which are slightly crosslinked, function as viscosifiers in aqueous solvent systems. In general, these swellable polymers are preferred because they tend to be far less "slimy" going on and once the hands perspire and are exposed to water after treatment. Excessive crosslinking will result in polymers that do not swell sufficiently to increase the viscosity of the composition. In order to ensure adequate swelling, if a chemical crosslinker is used, the concentration of crosslinker is quite low, e.g., less than 1000 parts per million (ppm), and preferably less than 500 ppm, based on the weight of the dry polymer.

A class of crosslinked polymers suitable for use in the compositions of the present invention include acrylamide and at least one other quaternary monomer selected from the group consisting of trialkylaminoalkylacrylate and methacrylate salts, dialkyldiallyl ammonium salts, acrylamidoalkyltrialkyl ammonium salts, methacrylamidoalkyltrialkyl ammonium salts, and monomers that include imidazolinium salts. The counterions are preferably $F^-$, $Cl^-$, $Br^-$, and $CH_3(CH_2)_nSO_4^-$ where n=0-4. Other comonomers may also be added including N-vinyl pyrrolidone, N-vinyl caprolactam, methyl vinyl ether, acrylates, methacrylates, styrene, and the like. A particularly preferred polymer is a poly(2-methacryloxyethyl trimethyl ammonium chloride) polydimethylaminoethyl methacrylate, which conforms to the CTFA designation Polyquaternium 37. Another preferred polymer includes acrylamide and methacryloyloxyethyl trimethyl ammonium chloride, which conforms to the CTFA designation Polyquaternium 32. These are commercially available from Allied Colloids Inc. of Suffolk, Va. as SALCARE SC95, SC96, and SC92.

Other swellable polymers (i.e., slightly crosslinked polymers) can be prepared using ionizing radiation to crosslink. For example, polymers of N-vinyl lactams, such as N-vinyl pyrrolidone, when exposed to gamma radiation increase in molecular weight and may actually crosslink. This crosslinking allows for more efficient thickening (less polymer required to achieve a certain viscosity) and an improved cosmetic feel. Other polymers that when exposed to gamma radiation result in crosslinking, include polymers such as LUVIQUAT HM 552 (copolymers of vinylimidazolium methochloride and vinylpyrrolidone, which conforms to the CTFA designation Polyquaternium-16), and GAFQUAT HS-100 (vinylpyrrolidone/methacrylamidopropyltrimethylammonium chloride copolymer which conforms to the CTFA designation Polyquaternium-28).

Chemical crosslinking using polyunsaturated monomers such as diallyl maleate may also prove useful. Other suitable crosslinkers are multi-ethylenically unsaturated compounds wherein the ethylenic groups are vinyl groups (including substituted vinyl groups, such as isopropenyl groups), allyl groups, and/or methallyl groups, which groups are bonded to nitrogen or oxygen atoms. Vinyl, allyl, and methallyl groups, as used herein, include substituted derivatives. Exemplary compounds include divinyl, diallyl, or dimethallyl esters, ethers, amides, or ureas. Specific examples are disclosed in U.S. Pat. No. 5,225,473 (Duan) and U.S. Pat. No. 4,931,282 (Asmus et al.).

A range of crosslinked polyvinylpyrrolidone (PVP) materials have been prepared via covalent crosslinking with diallyl maleate or by radiation crosslinking of linear PVP powders, Crosslinked PVP prepared under these techniques can produce colloidal particles which are highly swellable in aqueous solutions and thereby produce viscous solutions. The polymers are also nonionic and have excellent compatibility with cationic excipients.

Anionic swellable polymeric thickeners may also be useful. As described above preferred anionic polymers for use with antimicrobial compositions which include carboxylic acid functional enhancers (and are thus formulated at lower pH) are polymers having sulfonic acid, sulfonate, phosphonic acid, or phosphate groups.

Associative Polymers. Associative polymers can be used to thicken the compositions of the present invention as well. Such polymers thicken as a result of hydrophobic or Van de Waals association of hydrophobic side chains. Such associative polymers can form viscous to gelled aqueous solutions despite their relatively low molecular weights. Polymers that are alcoholic soluble can be modified by the addition of a long chain hydrophobic group. A preferred class of such associative polymers are based on nonionic ethylenically unsaturated monomers wherein at least one comonomer has at least 16 carbon atoms.

An example is cetyl hydroxyethylcellulose, available as NATROSOL PLUS from Aqualon, which utilizes an associative mechanism to enhance the viscosity it produces. Grafted side chains of cetyl alkyl groups can associate with neighboring alkyl hydrophobes. These interpolymer associations can dramatically increase the viscosification efficiency of the polymer. Longer chain alkyl, alkenyl, and aralkyl groups may also be suitable. For example, another preferred associative polymer is Arsitoflex HMB, which is ammonium acryloyldimethyltaurate/beheneth-25 methacrylate crosspolymer and is available from Clariant Corp.

(5) Neat Compositions. The compositions of the present invention also may be delivered to the treatment site in a neat form or in a volatile solvent that rapidly evaporates to leave behind a neat composition. Such compositions may be solid, semisolid, or liquid. In the case where the compositions are solid, the antimicrobial and/or the enhancer and/or the surfactant may optionally be microencapsulated to either sustain the delivery or facilitate manufacturing a powder, which is easily delivered. Alternatively, the composition can be micronized into a fine powder without the addition of other components or it may optionally contain fillers and other ingredients that facilitate powder manufacture. Suitable powders include, but are not limited to, calcium carbonate, calcium phosphate, various sugars, starches, cellulose derivatives, gelatin, and polymers such as polyethylene glycols.

When hydrophobic antimicrobial lipids are used, a method for micronizing a hydrophobic agent may be used wherein the hydrophobic agent is dissolved in an effective amount of a first solvent that is free of polymer (such as the method described in U.S. Pat. No. 6,746,635). The hydrophobic agent and the solvent form a mixture having a continuous phase. A second solvent and then an aqueous solution are introduced into the mixture. The introduction of the aqueous solution causes precipitation of the hydrophobic agent and produces a composition of micronized hydrophobic agent having an average particle size of 1 micron or less. The particle size for use in delivery to the nose or other tissue may be significantly larger to direct delivery to the proper site. For example, to deliver the antimicrobial powder to the nose, nasal cavities, and/or throat without passing into the lungs, larger particles may be required.

Bioadhesive polymers optionally may be added to neat compositions as well as the other physical forms. Numerous suitable bioadhesive polymers are discussed in International Publication No. WO 93/21906. Representative bioadhesive polymers of particular interest include bioerodible hydrogels described by H. S. Sawhney et al., in Macromolecules, 26:581-587 (1993), including polyhyaluronic acids, casein, gelatin, glutin, polyanhydrides, polyacrylic acid, alginate, chitosan, poly(methyl methacrylates), poly(ethyl methacrylates), poly butylmethacrylate), poly(isobutylmethacrylate), poly(hexylmethacrylate), poly(isodecyl methacrylate), poly (lauryl methacrylate), poly(phenyl methacrylate), poly(methyl acrylate), poly(isopropyl acrylate), poly(isobutyl acrylate), and poly(octadecyl acrylate). Preferred polymers are polyacrylic acid (e.g., CARBOMER polymers) and poly (fumaric-co-sebacic)acid. Other bioadhesive and bioerodible polymers are described in U.S. Pat. No. 6,746,635. Particularly preferred are slightly crosslinked polyacrylic acids such as those sold under the CARBOPOL brand by BF Goodrich.

The antimicrobial compositions also may include suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

The neat compositions according to the present invention may be conveniently delivered in the form of an aerosol spray-presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. Those of skill in the art can readily determine the various parameters and conditions for producing aerosols without resort to undue experimentation. Inhaled medications are preferred in some embodiments because of the direct delivery to the lung. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Techniques for preparing aerosol delivery systems are well known to those of skill in the art. Generally, such systems should utilize components which will not significantly impair the biological properties of the agent (see, for example, Sciarra and Cutie, "Aerosols," in Remington's Pharmaceutical Sciences, 18th edition, 1694-1712 (1990)).

The compounds may also be formulated in rectal or vaginal compositions such as suppositories or retention enemas, e.g., containing conventional suppository bases such as cocoa butter or other glycerides.

Viscosity

The viscosity of the compositions of the present invention depends on the end use. For applications where the composition is intended to penetrate a cavity rapidly such as an ear drop the viscosity is preferably quite low. This may also be true for compositions intended to treat the surface of foods such as meat, fruit, vegetables, eggs, and many other foods. Similarly, for compositions intended to disinfect hard inanimate objects such as medical instruments, floors, counter tops, etc. the viscosity is preferably relatively low to prevent leaving behind thick films of the compositions. For these applications the viscosity may be less than 500 cps and perhaps less than 100 cps, e.g., less than 20 cps.

In many topical applications, however, the viscosity is preferably much higher. Certain preferred compositions of the present invention have a viscosity of at least 500 Centipoise (cps) for ease of application topically. More preferably, compositions of the present invention have a viscosity of at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). Lower viscosity compositions can be used, however, in certain applications, such as for the treatment of middle ear infection and chronic sinusitis. For example, afflictions of the middle ear (e.g., otitis media or infection of the middle ear) may be treated with compositions of the present invention having a viscosity lower than 1000 cps more readily by administration through the nose and into the Eustachian tubes. The viscosity is measured by the Viscosity Test described herein. Preferred compositions meet the above viscosity limitations even when warmed to 32° C. Most preferred compositions meet the above viscosity limitations even when warmed to 35° C., or as high as 37° C.

In some embodiments of the present invention, the compositions have a viscosity of at least 20 cps, preferably at least 100 cps, when measured by the Viscosity Test described herein. Higher viscosities are preferred to reduce migration as well as to provide substantivity (resistance to removal by fluids) to ensure long-term antimicrobial activity.

Delivery Methods and Devices

Antimicrobial compositions of the present invention can be provided to a medical professional in a single composite formulation or in multiple parts. For example, a composition can be provided in two parts (e.g., in two separate containers or two separate compartments of the same container), one part containing the antimicrobial component and one part containing the enhancer. Other components of the composition can be combined with either one of the two parts. Alternatively, the other components can be included in a third part.

In other embodiments, a composition can be provided in two parts and the antimicrobial component can be made in situ. For example, a fatty alcohol may be combined with a hydroxyacid and converted to the ester. This esterification optionally may be added by the use of an enzyme. This may occur on the tissue or prior to application to the tissue.

Topical treatment regimens according to the practice of this invention include applying a safe and effective amount of the compositions described herein directly to the infected or at-risk skin, wound, or mucous membrane; particularly, the nasal nares and passages as well as acute and chronic wounds that are particularly susceptible to microbial contamination.

Compositions of the present invention can be delivered using a variety of techniques. Typically, the compositions are delivered to the skin and/or mucosal tissue in a manner that allows them to penetrate into the skin and/or mucosal tissue, as opposed to through the tissue into the blood stream. This concentrates the compositions locally at the site in need of treatment. This delivery can be accomplished by spraying, dipping, wiping, dropping, pouring, toweling, inhaling, or the like, onto the area to be treated.

In the methods of the present invention, the compositions may be provided as a formulation suitable for delivery to mammalian tissue (e.g., skin and/or mucosal surfaces). Suitable formulations can include, but are not limited to, creams, gels, foams, ointments, lotions, balms, waxes, salves, solutions, suspensions, dispersions, water in oil or oil in water emulsions, microemulsions, pastes, powders, oils, lozenges, boluses, and sprays, and the like.

The compositions may be sprayed from a pressurized container. The pressure may be supplied by an external means such as squeezing the container, through the use of a mechanical pump, or with the use of a propellant. Suitable propellants include chlorofluorocarbons (CFCs), hydrochlorofluorocarbons (HCFCs), hydrofluorocarbons (HFCs), hydrofluoroethers (HFEs), perfluorinated alkanes, and (C1-C5)alkanes, such as propane and butane, as well as nitrous oxide and dimethyl ether. Preferred propellants are lower alkanes such as propane, butane, isobutene, as well as HCFCs.

If delivered as a foam, the composition may be dispensed from an aerating dispenser such as the F2 Finger Pump Foamer available from Air Spray International Pompano Beach, Fla. Alternatively, the foam may be generated using a suitable propellant such as those described above.

In some embodiments, compositions of the present invention can be formulated into various consumer products, such as deodorants, shampoos, shower gels, detergents, household cleaning products, etc.

For very high viscosity formulations the composition may be delivered in essentially a solid dosage form by placing the composition in or on the tissue to be treated. For example, a small suppository type delivery could be placed into the anterior nares for eradication of *Staphylococcus* sp.

Various other modes of administration can be used as well known to one of skill in the art depending on the desired location for contact of the antimicrobial compositions of the present invention. For example, afflictions of the middle ear (e.g., otitis media or infection of the middle ear) may be treated with compositions of the present invention by administration through the nose and into the Eustachian tubes or they can be instilled directly into the middle ear through the tympanic membrane. The formulations may traverse the tympanic membrane with the aid of a syringe or do so by diffusion. Penetration agents may be used to enhance diffusion across the tympanic membrane, for example, as discussed herein. It is noted that the antimicrobial ester itself may enhance the penetration of the composition across tissues and other membranes such as the tympanic membrane, for example.

For application to skin or mucosal tissue, for example, the compositions may be applied directly to the tissue from a collapsible container such as a flexible tube, blow/fill/seal container, pouch, capsule, etc. In this embodiment, the primary container itself is used to dispense the composition directly onto the tissue or it can be used to dispense the composition onto a separate applicator. For example, for delivery to the nose or topical tissue, the composition could be dispensed directly from a tube and spread by a number of means including squeezing the outside of the nose together repeatedly, wiping with the tip of the tube or with a separate device such as a spatula, cotton, rayon, or other natural or synthetic based fiber swab.

Other application devices may also be suitable including applicators with foam tips, brushes, and the like. Importantly, the applicator must be able to deliver the requisite amount of composition to the tissue. Therefore, in most instances applicator devices such as webs and swabs are coated on the applicator web at greater than 50% by weight of the dry web and preferably in excess of 100% by weight of the dry web. (On a swab this would include the weight only of the web and not the applicator stick.)

The collapsible containers may be made in a number of single layer, laminate, or coextruded constructions. Materials of construction may include polyolefins such as low, medium, or high density polyethylene including low and linear low density polyethylene, polypropylene, as well as copolymers of ethylene and/or propylene with other polar or non-polar comonomers; polyamides such as nylons; polyesters such as polyethylene terephalate, polybutyleneterephalate, polyethylenenaphthalate; polyurethanes; polyacrylates; and the like. In some constructions it may be desirable to include a barrier material to prevent evaporation of one or more components of the formulation. Suitable barrier materials include polyesters (e.g., polyethylene terephthalate, polyethylene naphthalate, polybutylene terephalate, and the like), fluorinated layers such as polytetrafluoroethylene (PTFE, e.g., TEFLON), polyamides (e.g., nylon), chlorotrifluoroethylene (ACLAR), polyvinylidene fluoride, as well as copolymers of perflourinated monomers with partially fluorinated monomers such as copolymers of tetrafluoroethylene/hexafluoropropylene/vinylidene fluoride (THV Fluorothermoplastic from Dyneon Company), polyvinylchloride, polyvinylidene chloride (PVDC, e.g., SARAN HB), ethylene vinyl alcohol (EVOH), polyolefins (e.g., polyethylene, high density polyethylene, polypropylene, and combinations thereof). Oriented and biaxially oriented polymers may be particularly preferred.

Particularly preferred barrier constructions include metallic foil barriers such as aluminum foil laminates, HDPE, PET, PETG, PEN laminates of polyester and polyolefin (in particular PET/HDPE or HDPE/PET/HDPE), laminates of PET and EVOH, biaxially oriented nylon, PVDC, Nylon/EVOH/Nylon (OXYSHIELD OUB-R), chlorotrifluoroethylene and laminates thereof, ceramic layer including silicon oxide ($SiO_x$ where x=0.5-2 and preferably 1-2) coated thermoplastics, and ceramic coated PET (CERAMIS available from CCL Container/Tube Division, Oak Ridge, N.J.).

Compositions of the present invention may be applied to a mucosal surface with the use of a delivery device such as cervical caps, diaphragms and solid matrices such as tampons, cotton sponges, cotton swabs, foam sponges, and suppositories.

Accordingly, compositions of the present invention can also be delivered from cloth, sponges, paper products (e.g., paper towels, towellettes, and wipes), tampons, undercast padding, and dental floss, for example.

In some embodiments, an applicator may be used to place the device and/or antimicrobial composition in the proper location, for example, on the mucosal surface of a vagina, nasal cavity, rectum, or the like. Examples of such applicators include, for example, cardboard or plastic tube applicators commonly used for inserting tampons or suppositories.

The compositions of the present invention can be delivered from various substrates for delivery to the tissue. For example, the compositions can be delivered from a wipe or pad which when contacted to tissue will deliver at least a portion of the composition to the tissue. For application to nasal cavities the compositions may be provided by a non-woven swab such as a "Q-tip" brand cotton swab, into a foam tip applicator, and the like. The substrate may be used to deliver the composition essentially instantaneously or may be left in contact with the tissue. For example, a substrate in a tubular form could be delivered to the anterior nares using a suitable applicator and left in the anterior nares. The annular nature of the device is designed to allow delivery of the active while allowing the patient to freely breathe through the nose.

Also, compositions of the present invention can be coated onto medical devices that contact mammalian tissue (e.g., skin, mucous membranes, wounds, etc.). Examples of such devices include catheters such as urinary tract catheters and vascular access catheters.

Antimicrobial compositions of the present invention can be formulated for additional controlled release (beyond that provided by the compositions previously discussed) if desired. For example, the antimicrobial component may be formulated into compatible liposomes, microcapsules, microglobules, microbeads, and/or microspheres such as those made from natural polymers including, but not limited to, polysaccharides, agar, starch and starch derivatives, cellulose and cellulose derivatives, and synthetic polymers such as polyolefins (e.g., polyethylene and polypropylene), polystyrene, polyacrylates, and the like, as well as inorganic materials such as clays and zeolites. The antimicrobial component may also be formulated into multiple emulsions such as oil-in-water-in-oil emulsions or water-in-oil-in-water emulsions where the oil is an organic oil or a silicone base oil. In addition, water soluble or swellable polymers can be combined with the antimicrobial in a soluble or swollen state, dried, and added to the various compositions to further sustain release. If a prolonged release of the antimicrobial is desired it also may be useful to incorporate a hydrophobic component in which the antimicrobial lipid is soluble.

Topical antimicrobial treatment regimens according to the practice of this invention include applying an effective amount of the compositions described herein directly to the infected or at-risk mammalian tissue (particularly, skin or mucous membrane); particularly, the nasal nares and passages that are particularly susceptible to microbial contamination. Compositions of the present invention can be delivered using a variety of techniques. Typically, the compositions are delivered to the mammalian tissue (particularly, the skin and/or mucosal tissue) in a manner that allows them to penetrate into the tissue, as opposed to through the tissue into the blood stream. This concentrates the compositions locally at the site in need thereof. This can be accomplished by spraying, dipping, wiping, dropping, pouring, toweling, or the like, onto the area to be treated.

If a composition of the present invention includes certain poloxamer block copolymers of ethylene oxide and propylene oxide generally having greater than 60 mol-% polyethylene oxide (such as those available under the trade names PLURONIC F127 and F108 from BASF Corp.), as well as certain modified cellulose polymers, and is applied topically, for example, thermally induced gelation can occur. Thus, various components can be selected for use in compositions of the present invention to produce a desired application effect.

The dose and frequency of application will depend on many factors including the condition to be treated, the concentration of antimicrobial and enhancer, the microbe to be killed, etc. Typically, the compositions will be delivered in dosages of at least 10 milligrams per square centimeter ($mg/cm^2$) of tissue, preferably at least 20 $mg/cm^2$ of tissue, more preferably at least 30 $mg/cm^2$ of tissue, and most preferably at least 50 $mg/cm^2$ of tissue, for most applications. Application can be made once, or several (e.g., 2-4) times daily for one or more days. Typically, the composition is applied 1 or 2 times/day for 1-7 days. For example, decolonization of the anterior nares may require a dose of 0.25 gram (g) per nares applied 1-3 times per day for 1-5 days. Treatment of impetigo may require 0.5 g/15 $cm^2$ (33 $mg/cm^2$ of tissue) applied 1-3 times/day for 3-10 days.

Additional Antimicrobial Components and Delivery Systems

The present invention also provides a delivery system for an antimicrobial component (e.g., antimicrobial lipids as well as other antimicrobial agents, particularly antiseptics). Such delivery systems include a hydrophobic component and a hydrophilic component, wherein the composition has a viscosity of at least 500 cps, and further wherein the hydrophobic component forms the greatest portion of the composition by weight. Alternatively, such delivery systems include a hydrophobic component, a hydrophilic component, and a surfactant, wherein the hydrophobic component forms the greatest portion of the composition by weight.

Methods of delivery of antimicrobial components are also provided using such delivery systems (i.e., compositions). Such methods involve applying to a surface a composition that includes a hydrophobic component and a hydrophilic component, herein the composition has a viscosity of at least 500 cps, and further wherein the hydrophobic component forms the greatest portion of the composition by weight. Alternatively, the method can involve applying to a surface a composition that includes a hydrophobic component, a hydrophilic component, and a surfactant, wherein the hydrophobic component forms the greatest portion of the composition by weight.

In such delivery systems, the antimicrobial component can include an antimicrobial component, such as that described herein. Alternatively (or additionally), the antimicrobial component can include other antimicrobial agents, particularly other antiseptics. Examples of suitable antiseptics include, for example, peroxides, (C6-C14)alkyl carboxylic acids and alkyl ester carboxylic acids, antimicrobial natural oils, as described in Applicants' Assignee's Copending U.S. patent application Ser. No. 10/936,133, filed on Sep. 7, 2004; halogenated phenols, diphenyl ethers, bisphenols (including but not limited to p-chloro m-xylenol (PCMX) and triclosan), and halogenated carbanilides described in Applicants' Assignee's Copending U.S. patent application Ser. No. 10/936,171, filed on Sep. 7, 2004; digluconate, diacetate, dimethosulfate, and dilactate salts; polymeric quaternary ammonium compounds such as polyhexamethylenebiguanide; silver and various silver complexes; small molecule quaternary ammonium compounds such as benzalkonium chloride and alkyl substituted derivatives; di-long chain alkyl (C8-C18) quaternary ammonium compounds; cetylpyridinium halides and their derivatives; benzethonium chloride and its alkyl substituted derivatives; and octenidene described in Applicants' Assignee's Copending U.S. patent application Ser. No. 10/936,135, filed on Sep. 7, 2004; and compatible combinations thereof.

In certain embodiments, the antiseptics of this invention may optionally be combined with an effective amount of an antimicrobial lipid antiseptic comprising a (C7-C12) saturated fatty acid ester of a polyhydric alcohol, a (C12-C22) unsaturated fatty acid ester of a polyhydric alcohol, a (C7-C12) saturated fatty ether of a polyhydric alcohol, a (C12-C22) unsaturated fatty ether of a polyhydric alcohol, an alkoxylated derivative thereof, or combinations thereof, wherein the alkoxylated derivative has less than 5 moles of alkoxide per mole of polyhydric alcohol; with the proviso that for polyhydric alcohols other than sucrose, the esters comprise monoesters and the ethers comprise monoethers, and for sucrose the esters comprise monoesters, diesters, or combinations thereof, and the ethers comprise monoethers, diethers, or combinations thereof. Useful antiseptics of this class are further described in applicants' copending application "Antimicrobial Compositions and Methods of Use," U.S. Publication No. 2005/0089539-A1.

The antimicrobial esters of this invention may also be utilized as preservatives in cosmetic and pharmaceutical compositions. These materials are particularly applicable to formulations where hydrolysis of the ester is less of a concern, i.e., where the composition has little or no water or in aqueous composition having a pH of 5-9 and preferably 6-8. The antimicrobial esters are added as a preservative to a food composition, cosmetics, drugs or the like during mixing or manufacturing at a safe and effective level. For a preservative in cosmetics and pharmaceuticals the effective level is defined in accordance with the Microbial Limits Test set out in USP 61 of the United States Pharmacopeia, USP 26, 2003. In a preferred embodiment, the antimicrobial ester(s) are present in the additive composition at a level of about 0.025 to 3%; more preferably about 0.025 to about 1%, and still more preferably about 0.05 to about 0.5% by weight of the preserved composition. Also present can be enhancers as discussed previously at the ratio of enhancer to antimicrobial ester.

It will be appreciated that the preferred levels described above relate to the preparation of an additive composition. The safe and effected level of such components as employed in the final preserved food, cosmetic, drug composition (or the like) vary according to a host of factors including the type of food, the base of the cosmetic, the mode of treatment of the drug, etc., the determination of the final level, i.e., the amount of the preservative composition to be added to the end product, is well within the skill of the artisan. In general, however, the additive composition of the present invention are added to the final product at a level of about 0.01 to about 10% to arrive at the preserved food compositions of the present inventions.

Although the detailed description of illustrative embodiments provided herein (particularly with respect to enhancers, surfactants, other additives, and for making such compositions) specifically refers to an antimicrobial ester component, such description also applies to other antiseptics.

EXAMPLES

Objects and advantages of this invention are further illustrated by the following examples, but the particular materials and amounts thereof recited in these examples, as well as other conditions and details, should not be construed to unduly limit this invention.

Test Protocols

Antimicrobial Kill Rate Test

Antimicrobial compositions were challenged with test cultures of Methicillin Resistant *Staphyloccus aureus* (MRSA) ATCC#33593 (commercially available from American Type Culture Collection, Rockville, Md.), and *Escherichia coli* (*E. coli*), ATCC #11229.

Bacteria Culture Preparation:

Bacteria were grown in Tryptic Soy Broth (TSB) (commercially available from Difco, Detroit, Mich.) at 35° C. for 18-24 hours (hrs). A 0.3 milliliter (mL) culture suspension was spread on the surface of a Tryptic Soy Agar plate that was incubated at 35° C. for 18-24 hrs. Bacterial cells were harvested from the agar plate with a glass L-rod by adding 3 mL of TSB and were transferred into a snap cap 5 mL polypropylene culture tube. The resulting cell suspension was called the working culture.

Liquid Test Procedure:

A 25 ml Erlenmeyer flask containing a magnetic stirring bar was filled with 20.0 ml of a liquid antimicrobial composition. The flask was placed in a temperature controlled water bath equipped with stirring capability. The magnetic stirrer was turned on and temperature of the composition was adjusted to 23° C.+/−2° C.

Exposure of Bacteria to the Compositions:

At the start of each exposure time, 0.1 mL of the bacteria working culture being tested was added to the antimicrobial composition. The exposure times were 1 minute, 3 minutes, 5 minutes, and 10 minutes. At the end of each exposure time, 1 mL of suspension was transferred to a test tube containing 9 mL Letheen broth (VWR Scientific, Batavia, Ill.) at 23° C. After vortexing, the neutralized $10^{-1}$ cell suspension was further diluted to $10^{-2}$ by transferring 1 mL into 9 mL Letheen broth tubes. From each of the two dilutions, 0.1 mL volume was plated onto a TSA plate and spread with the L-rod producing $10^{-2}$ and $10^{-3}$ dilutions. The plates were incubated at 35° C.±2° C. for 48 hours (hrs) and colony-forming units (CFU) were counted and recorded. The procedure was repeated using three to five replicate samples of each composition. The diluted bacterial suspensions were plated in duplicate.

Data Analysis:

Microbial kill rate was reported as a $\log_{10}$ reduction which was determined by calculating the difference between the $\log_{10}$ of the initial inoculum count and the $\log_{10}$ of the inoculum count after exposure to compositions or components of the composition for 1-minute ($T_1$), 3-minute ($T_3$), 5-minute ($T_5$), and 10-minute ($T_{10}$) intervals.

The two duplicate plates at the selected dilution level were averaged and the initial inoculum count was calculated using the following formula:

Initial Inoculum Count=$T_0$=Ave. CFU of replicates×1/dilution level×0.005

Where the sample inoculums were diluted (0.1 ml in 10 ml of the compositions, the initial inoculum were reduced by 0.1 ml/10 ml, which equals 0.010).

For the test plates of each organism at each time period, the CFU's on all the $10^{-2}$ and $10^{-3}$ plates were counted. The dilution level that had counts between 25 and 250 was determined. The two duplicate plates at the selected dilution level were averaged and the test plate count at the given time was calculated using the following formula:

$T_1$, $T_3$, $T_5$, and $T_{10}$=CFU of 3 replicates×1/dilution level where the plate count of 3 replicates were at 2 minute, 5 minute, and 10 minute intervals, respectively.

For the compositions the log reduction was determined by taking the logarithm to the base 10 of $T_0$, $T_1$, $T_2$, $T_5$, and $T_{10}$ and using the following formulas:

Log reduction at 1 minutes $\log_{10} T_0 - \log_{10} T_1$,

Log reduction at 3 minutes $\log_{10} T_0 - \log_{10} T_3$,

Log reduction at 5 minutes=$\log_{10} T_0 - \log_{10} T_5$

Log reduction at 10 minutes=$\log_{10} T_0 - \log_{10} T_{10}$

The average of the replicates was calculated by averaging the log reductions at each time period.

When standard dilution procedures result in the most dilute plate having too many colonies to count, an estimate of upper limit of detection was calculated based on initial inoculum and dilutions. This number is reported as a result that is less than the limit, for example <2.04 would indicate that 2.04 was the upper level of possible log reduction but the value could be as low as 0.

Purity and Aging Using Gas Chromatography

This method was used to test the purity of the antimicrobial lipids or to check for chemical stability in a composition after aging. Antimicrobial Compositions were prepared and while in a well-mixed, liquid state.

Testing Concentration of an Antimicrobial Lipid in a Composition:

If the composition was a solid or ointment at room temperature it was poured into individual vials while still warm and allowed to solidify. For aging tests the zero time ($T_0$) vials were refrigerated at 4° C. and the other vials were placed in a LAB LINE Orbital Environmental Incubator and incubated at either 23° C. or 40° C. and 65° C. at 200 RPM. Compositions incubated at 65° C. were in the liquid state. These compositions were incubated with and without shaking to see if agitation contributed to loss of the antimicrobial lipid. One vial of each composition was removed after 7 days and after 4 weeks. After they were removed, they were shaken until they solidified and refrigerated at 4° C. until assayed.

The internal standard, which was used for all extractions, contained 0.4 mg/mL monodecyl glycerol ($GMC_{10}$) from Sigma-Aldrich in chloroform and was prepared and stored in a clean glass bottle which was sealed with a TEFLON lined screw cap. At the time of assay, methanol was mixed with the stock standard in the ratio of 2 parts chloroform to 1 part methanol giving a stock internal standard which was 0.267 milligram per milliliter (mg/mL) in $GMC_{10}$.

If a standard was available the following procedure was used. If a standard was not available the percentage was given in weight percent. When a standard was available, the stock standard (1.8 mg/mL) was prepared by adding 18 mg of the standard to a tared 10 mL volumetric flask, recording the exact weight, filling it to the mark with the stock internal standard, and mixing it well. The solution was transferred to a clean glass vial, which was sealed with a TEFLON lined screw cap.

The working standard was diluted using volumetric pipettes, additional stock internal standard, and clean glass vials according to the following scheme.

| Standard level | Standard | Volume of Standard | Volume of Internal Standard | Antimicrobial lipid standard (mg/mL) |
| --- | --- | --- | --- | --- |
| 1 | Stock | 5 | 5 | 0.9 |
| 2 | Standard 1 | 2 | 4 | 0.3 |
| 3 | Stock | 1 | 8 | 0.2 |
| 4 | Standard 3 | 3 | 3 | 0.1 |

The dilutions were stored in clean glass vials and sealed with TEFLON lined screw caps.

All test samples and matrices were allowed to reach room temperature before assay. They were mixed well by stirring with clean glass rods. Using graduated pipettes and clean glass vials which held 7-8 ml, the extractions were performed as follows. Triplicate 50 mg samples of each aged composition were added to tared vials and the exact weights recorded. (For samples that were emulsions with a larger droplet size, larger samples were needed to ensure a uniform sample. In those cases, a larger sample size was obtained and processed proportionately.) To these 5.0 mL of internal standard were added. The samples were mixed until they dissolved or were evenly dispersed and then 1.7 mL of 0.4 weight percent potassium chloride solution was added to each. The vials were capped, vortexed for 1 minute, and then centrifuged at top speed on a clinical centrifuge (IEC) until 2 clear phases resulted (3-5 minutes). The lower phase (organic) was separated from the upper phase (aqueous) by suction using a Pasteur Pipette, which had been inserted through the upper phase. It was transferred to a second vial containing a small amount (approximately 200 milligrams (mg)) of sodium sulfate in order to dry the sample. A portion was then transferred to an auto sampler for GC analysis.

Single extracts of each of the four standards were made in the same manner as the samples except that 50 mg of formulation matrix (formulated without the antimicrobial lipid), with the difference made up with another component (normally the vehicle in the formulation)) was added to each extraction vial followed by 5.0 mL of each of the working standards. An internal standard blank was also extracted as well as a sample matrix without any internal standard.

The order of analysis was Internal Standard blank, standards (lowest to highest), solvent blank, samples (in random order), and calibration checks every 16 injections and at the end (level 2 standard). Each sample and standard was injected once.

The Gas Chromatography Conditions were:

| | |
|---|---|
| Instrument | HP 5890 or 6890 |
| Column | 15 meter ZB-5, 0.25 micon (μm) film 0.25 mm ID |
| Carrier | He, $1.52 \times 10^5$ N/m$^2$ (22 pounds per square inch (psi)) constant pressure (6890-constant flow 1 millilters per minute (mL/min)) |
| Injection | 1.5 microliter (μL) split 1:60, injector temp 300° C. |
| Liner | Restek SILTEK deactivated liner with SILTEK deactivated glass wool (Cat. No. 22406-213.5) |
| Program | 50° C. initial, 7° C./min to 200° C., 20° C./min to 300° C., hold 10 minutes (min) |
| Detector | FID at 300° C. |

The triplicate samples of each time point were prepared and analyzed once each. The area ratio of antimicrobial lipid/internal standard (GMC$_{10}$) was converted into mg antimicrobial lipid/sample using the standard curves, which was then divided by the sample weight (100 mg) and multiplied by 100 to obtain a weight percent of antimicrobial lipid in the sample. The weight percent from each of the triplicate samples was then averaged and a standard deviation was obtained.

Good linearity was obtained with correlation coefficient, R>0.99 over the range of analysis.

Samples that were checked for purity were diluted into chloroform to about 2 mg/mL. If a standard was available it was checked as well. An internal standard was added when in did not interfere with the analysis. A suitable internal standard was GMC10 or CHYSTAPHYL 98 available from Chemic Labs, Canton, Mass.

Examples 1-6 and Comparative Example A

Antimicrobial compositions were prepared using the components shown in Table 1. DOSS and EDTA were added to the water and mixed to dissolve and form a solution. Next, IPA and PLURONIC were added and the mixture stirred until the PLURONIC dissolved. Finally the ester was added to form the test formulation. All of the formulations in Table 1 contained 10% PLURONIC, 1% DOSS and 10% isopropyl alcohol in addition to the components listed with water making up the remaining portion of the formulation.

TABLE 1

| Example No. | Ester | Ester Purity (wt-% by GC) | Wt-% Ester | EDTA |
|---|---|---|---|---|
| 1 | CHRYSTAPHYL 98-Lauryl lactate | >98 | 3 | 0.2 |
| 2 | CHRYSTAPHYL 98-Lauryl lactate | >98 | 1 | 0.2 |
| 3 | CHRYSTAPHYL 98-Lauryl lactate | >98 | 3 | 0 |
| 4 | DERMOL ML-myristyl lactate | 61 | 3 | 0.2 |
| Comparative A | None | | 0 | 0.2 |
| 5 | DERMOL OL-oleyl lactate | 65 | 3 | 0.2 |
| 6 | DERMOL TDSA-Tridecyl salicylate | ND* | 3 | 0.2 |

*The GC results for this compound was a very broad peak. Individual peaks could not be determined. The sample was not pure.

The compositions of Examples 1-4 and Comparative Example A were evaluated using the Antimicrobiol Kill Test and the results are shown in Table 2.

| GLOSSARY of COMPONENTS | | | |
|---|---|---|---|
| Acronym | Trade Name | Description | Source/Address |
| DOSS | 50% DOSS | 50% Dioctyl Sodium Sulfosuccinate in PEG-400 | Cytec Industries/West Paterson, NJ |
| EDTA | EDTA (Na)$_2$ | Sodium salt of ethylenediamine tetraacetic acid | W. R. Grace/Nashua, NH |
| PLURONIC | PLURONIC P-65 | Poloxamer/block copolymer of propylene oxide and ethylene oxide | BASF Corp./Parsippany, NJ |
| | CERAPHYL 31 ISP | Lauryl Lactate 48% | ISP, Lombard IL |
| | PELEMOL LL-Pheonix | Lauryl Lactate 75% | Pheonix Chemical, Sommerville, NJ |
| | CHRYSTAPHYL 98 | Lauryl Lactate 98% | Chemic Labs, Canton, MA |
| | PURASOLV EHL | 2ethylhexyllactate | Purac America, Lincolnshire, IL |
| | DERMOL OL | oleyl lactate | Alzo, Sayreville, NJ |
| | DERMOL TDSA | Tridecyl salicylate | Alzo, Sayreville, NJ |
| | DERMOL ML | myristyl lacate | Alzo, Sayreville, NJ |
| IPA | | Isopropal alcohol, Reagent grade | VWR International West Chester, PA |

TABLE 2

Antimicrobial Kill Test Results at 10 Minutes exposure time

| Example Formulation tested | Log Reduction of *S. aureus* (ATCC 33593) Initial inoculum 8.26 Log |
|---|---|
| 1 | 3.58 |
| 2 | 2.5 |
| 3 | <2* |
| 4 | 2.5 |
| Comparative A | <2* |
| 5 | <2* |
| 6 | <2* |

*The entry of <2 resulted from high initial inoculums and lack of antimicrobial activity in the time length tested that lead to colony counts too numerous to count even on the highest dilution plate. This prevented an exact log reduction from being determined. The log reduction was somewhere between 0 and 2 logs. Approximately 2 log was the lower limit of detection.

Examples 7-11 and Comparative B

Antimicrobial compositions were prepared using the components shown in Table 3. For the formulation that contains IPA, the procedure was as follows. DOSS, PLURONIC P65 and lipid ester were added to IPA and mixed to dissolve forming a solution. Next, EDTA was added to water and the mixture stirred until EDTA dissolved. Then the ester containing IPA solution was added to the resulting water solution to form the test formulation. For formulations that do not contain IPA, the mixing procedure was the same as described in Example 1. All of the formulations in Table 3 contained 10% PLURONIC in addition to the components listed with water making up the remaining portion of the formulation.

TABLE 3

| Example No. | Ester | Ester purity by GC | Ester | IPA | DOSS | EDTA |
|---|---|---|---|---|---|---|
| 7 | Lauryl Lactate (CERAPHYL 31) | 48 | 3 | 10 | 1 | 0.2 |
| 8 | Lauryl Lactate (PELEMOL LL) | 75 | 3 | 10 | 1 | 0.2 |
| 9 | Lauryl Lactate (PELEMOL LL) | 75 | 3 | 0 | 0 | 0 |
| 10 | 2ethylhexyllactate | Nd | 3 | 10 | 1 | 0.2 |
| 11 | 2ethylhexyllactate | Nd | 3 | 0 | 0 | 0 |
| Comparative B | None | Na | 0 | 10 | 1 | 0.2 |

Nd—not determined.
Na—not applicable

The compositions of Examples 7-11 were evaluated using the Antimicrobiol Kill Test and the results are shown in Table 4a-c.

TABLE 4a

Antimicrobial Kill Test Results

| Example Formulation | Log Reduction of *S. aureus* (ATCC 33593) Initial inoculum 7.95 log | | |
|---|---|---|---|
| | After 1 minute | After 3 minutes | After5 minutes |
| 8 | 4.63 | 4.22 | 5.95 |
| 9 | <2.41 | <2.41 | <2.41 |
| 10 | 4.32 | 5.95 | 5.95 |
| 11 | <2.41 | <2.41 | 3.35 |
| Comparative B | <2.04 | <2.04 | <2.04 |

TABLE 4b

Antimicrobial Kill Test Results

| Example Formulation | Log Reduction of *S. aureus* (ATCC 33593) Initial inoculum 5.24 log | | | |
|---|---|---|---|---|
| | After 1 minute | After 3 minutes | After 5 minutes | After 10 minutes |
| 8 | 3.24 | 3.24 | 3.24 | 3.24 |
| 9 | 1.2 | 1.3 | 1.17 | 1.44 |
| 11 | 3.18 | 3.24 | 3.24 | 3.24 |

TABLE 4c

Antimicrobial Kill Test Results

| Example Formulation | Log Reduction of *E. coli* (ATCC11229) Initial inoculum 7.59 log | | |
|---|---|---|---|
| | After 1 minute | After 3 minutes | After5 minutes |
| 7 | <2.04 | <2.04 | <2.04 |
| 10 | 5.59 | 5.59 | 5.59 |
| Comparative B | <2.04 | <2.04 | <2.04 |

TABLE 4d

Antimicrobial Kill Test Results

| Example Formulation | Log Reduction of *E. coli* (ATCC11229) Initial inoculum 5.81 log | | | |
|---|---|---|---|---|
| | After 1 minute | After 3 minutes | After 5 minutes | After 10 minutes |
| 8 | <0.27 | <0.27 | <0.27 | 0.38 |
| 9 | <0.27 | <0.27 | <0.27 | <0.27 |
| 11 | 1.49 | 3.58 | 3.39 | 3.81 |

Example 12

Purity Determination by GC was done on commercially obtained samples using the method defined in Test Protocols.

Figure 1B:
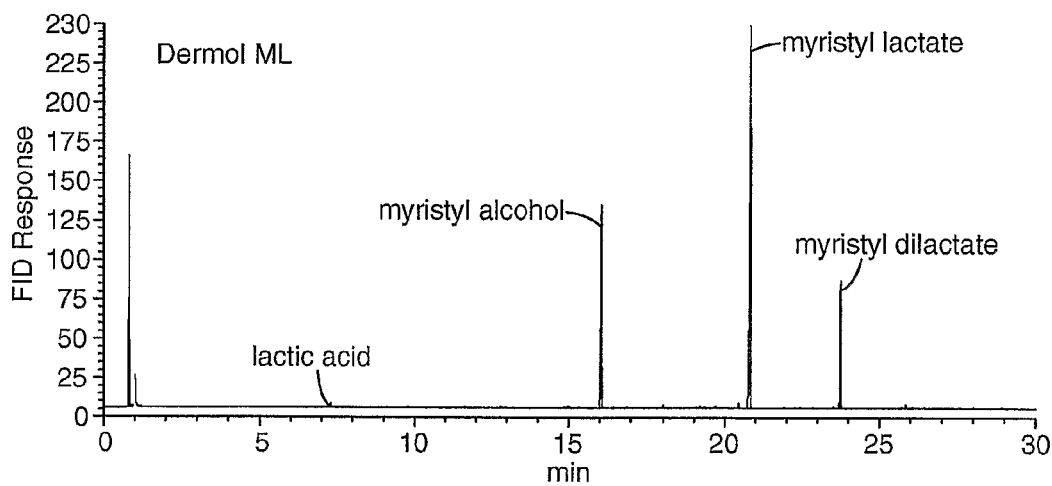
Figure 1C:
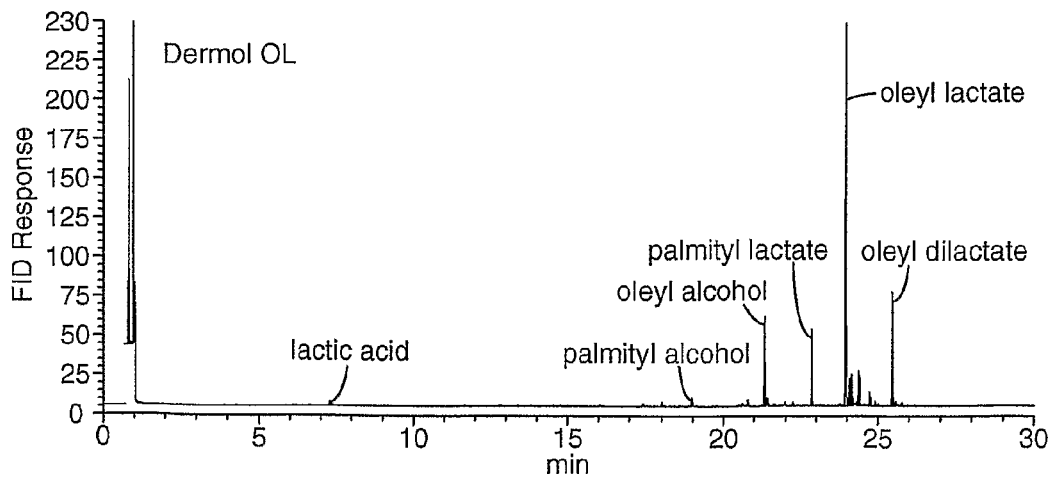

Alcohols and lactic acid were identified by retention time matching versus known standards and GC/MS spectra of the samples. Ester identification was made by GC/MS spectra of the samples. Weight percentages of alcohols and lactic acid were determined by comparing area response of component peaks in the samples with response factors obtained from standards of known concentration. Weight percentages of esters were determined by obtaining the area percent of each ester compared to the total ester area and multiplying that by the remaining weight percentage after removal of the alcohol and acid weight percentages. Areas of unidentified components were summed and reported as percentage of total area. Results are in Table 5 and the GC chromatograms are shown in FIG. 1(*a-c*).

TABLE 5

Purity by GC of Lipid Esters

| | Weight Percent of Identified Components | | |
|---|---|---|---|
| Component | CERAPHYL 31 | DERMOL ML | DERMOL OL |
| lauryl alcohol | 6.75 | ND | ND |
| Myristyl alcohol | 3.01 | 22.40 | ND |

TABLE 5-continued

Purity by GC of Lipid Esters

| | Weight Percent of Identified Components | | |
|---|---|---|---|
| Component | CERAPHYL 31 | DERMOL ML | DERMOL OL |
| palmityl alcohol | 0.61 | ND | 0.74 |
| oleyl alcohol | ND | ND | 12.73 |
| lactic acid | 12.07 | 8.21 | 8.06 |
| lauryl lactate | 44.17 | ND | ND |
| lauryl dilactate | 4.13 | ND | ND |
| Myristyl lactate | 17.17 | 61.23 | ND |
| Myristyl dilactate | ND | 8.15 | ND |
| palmityl lactate | 8.90 | ND | 6.11 |
| palmityl dilactate | 3.20 | ND | ND |
| oleyl lactate | ND | ND | 64.57 |
| oleyl dilactate | ND | ND | 7.79 |
| TOTAL (excluding unknowns) | 100.00 | 99.99 | 100.00 |
| unknowns (in area %) | 1.4 | 1.9 | 14 |

ND-Component was not detected in GC chromatogram.

Example 13-14 and Comparative C

Antimicrobial Efficacy on Hard Surfaces

Antimicrobial compositions were prepared using the components shown in Table 6.

The procedure for preparing the formulations was the same as described in Examples 7-11. The formulations were evaluated to disinfect hard, inanimate surfaces such as stainless steel or glass. Formulation 13-14 as well as Comparative Formulation C are contained in Table 6. All of the formulations in Table 6 contained 10% PLURONIC in addition to the components listed, with water making up the remaining portion of the formulation. The solutions were shaken well until a milky emulsion formed. The emulsion compositions were used immediately after being made.

TABLE 6

| | Components (Weight percent) | | | |
|---|---|---|---|---|
| Example No. | PURASOLV EHL | EDTA | DOSS | IPA |
| 13 | 3 | 0.2 | 1 | 10 |
| 14 | 3 | 0 | 0 | 0 |
| Comparative C | 0 | 0.2 | 1 | 10 |

Inoculum and Testing Procedure:

The procedure from AOAC Official Methods (AOAC Official Method 991.49, 6.2.05. was used for testing disinfectants against the following organisms: *Staphylococcus aureus* (MRSA) ATCC#33593) and *E. coli* (ATCC#11229). Initial Inoculum: *S. aureus* (MRSA) 7.84 logs (10 minute, 1 and 24 hour exposures), *S. aureus* (MRSA) 8.63 logs (5 and 30 minute exposures) and *E. coli:* 7.48 logs (all exposure times).

Briefly, in this test, hollow stainless steel or glass cylinders (penicylinders) were exposed and coated with the challenge bacteria from the initial inoculum solution for 15 minutes. The penicylinders were then removed from the inoculum and dried for 45 minutes. The penicylinders with the dried bacteria inoculum were dipped into the antimicrobial formulation for a set period of time, ranging from 5 minutes to 24 hours, minutes, removed and placed into neutralizer solution (letheen broth) for 30 seconds and then put into TSB for 24 hours. At the end of 24 hours the tubes containing the penicylinders were checked for turbidity and scored as either growth (fail) or no growth (pass). Ten inoculated glass carriers were evaluated for each time point. The results are reported in Table 7 (*E. coli*) and Table 8 (*S. aureus*, MRSA) below with the number with growth over total reported with associated pass/fail rating.

TABLE 7

| | Hard Surface Inoculated with *E. coli* | | | | |
|---|---|---|---|---|---|
| Antimicrobial Lipid Solution | Time Exposed to Antimicrobial Solution | | | | |
| | 5 minutes | 10 minutes | 30 minutes | 1 hour | 24 hours |
| Example 13 | 0/10, pass | 0/10, pass | NR | 0/10, pass | 0/10, pass |
| Example 14 | NR | 9/10, fail | 0/10, pass | 1/10, pass | 0/10, pass |
| Comparative C | NR | 10/10, fail | NR | 10/10, fail | 10/10, fail |

NR—Sample point was not run.

TABLE 8

| | Hard Surface Inoculated with *S. aureus* (MRSA | | | | |
|---|---|---|---|---|---|
| Antimicrobial Lipid Solution | Time Exposed to Antimicrobial Solution | | | | |
| | 5 minutes | 10 minutes | 30 minutes | 1 hour | 24 hours |
| Example 13 | 8/10, fail | 0/10, pass | NR | 0/10, pass | 0/10, pass |
| Example 14 | NR | 9/10, fail | 6/10, fail | 1/10, pass | 0/10, pass |
| Comparative C | NR | 10/10, fail | NR | 10/10, fail | 0/10, pass |

NR—Sample point was not run

Treated inoculated surfaces showed little or no growth on the 10 test pieces for the each of the 2 different bacteria tested (*Staphylococcus aureus* (MRSA) 33593 and *E. coli* (ATCC No. 11229)) with the antimicrobial lipid solution at times less than 1 hour. The comparative composition without lipid showed no effect at an hour. The results indicate that the antimicrobial lipid formulations are efficient hard surface disinfectants.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An antimicrobial composition comprising:
an effective amount of an antimicrobial component comprising a (C7-C14)saturated fatty alcohol ester of a (C2-C8)hydroxycarboxylic acid, a (C8-C22)mono- or poly-unsaturated fatty alcohol ester of a (C2-C8) hydroxycarboxylic acid, an alkoxylated derivative of either of the foregoing, or combinations thereof, wherein the alkoxylated derivative has less than 5 moles of alkoxide per mole of hydroxycarboxylic acid; and the composition further comprises an effective amount of an enhancer component selected from the group consisting of alpha hydroxyacids present in an amount of at least 0.25 wt/wt %, beta hydroxyacids present in an amount of at least 0.1 wt/wt %, a chelating agent present in an amount of at least 0.1 wt/wt %, a (C1-C4)alkyl carboxylic acid present in an amount of at least 0.1 wt/wt %, a (C6-C12)aryl carboxylic acid present in an amount of at least 0.1 wt/wt %, a (C6-C12)aralkyl carboxylic acid present in an amount of at least 0.1 wt/wt %, a (C6-C12)alkaryl carboxylic acid present in an amount of at least 0.1 wt/wt %, or combinations thereof; with the proviso that the composition does not include parabens or phenoxyethanol;

wherein the effective amount of the antimicrobial component in the composition is at least 0.25% by weight;

wherein water is present in less than 10 wt-%, and wherein the fatty alcohol ester in the antimicrobial component is at least 70% pure.

2. The composition of claim 1 wherein the antimicrobial component comprises (C8-C12) fatty alcohol esters of glycolic acid, lactic acid, 3-hydroxybutanoic acid, or combinations thereof.

3. The composition of claim 1 further comprising a surfactant component.

4. The composition of claim 1 further comprising a hydrophilic component.

5. The composition of claim 1 having at least 3 log reduction in test bacteria in 10 minutes when evaluated by the Antimicrobial Kill Rate Test.

6. The composition of claim 3, wherein the surfactant component does not comprise an ethoxylated sorbitan fatty acid ester.

7. The composition of claim 1, wherein the enhancer is a chelating agent present in an amount of at least 1%.

8. The composition of claim 1, wherein the enhancer is a chelating agent and a ratio of the concentration of the chelating agent to the antimicrobial component in the composition is within a range of 1:1 to 1:10.

9. The composition of claim 1, wherein the fatty alcohol ester in the antimicrobial component is at least 80% pure.

10. An antimicrobial composition comprising:

an effective amount of an antimicrobial component comprising a (C7-C14)saturated fatty alcohol ester of a (C2-C8)hydroxycarboxylic acid, a (C8-C22)mono- or poly-unsaturated fatty alcohol ester of a (C2-C8) hydroxycarboxylic acid, an alkoxylated derivative of either of the foregoing, or combinations thereof, wherein the alkoxylated derivative has less than 5 moles of alkoxide per mole of hydroxycarboxylic acid; and the composition further comprises an effective amount of an enhancer component selected from the group consisting of alpha hydroxyacids present in an amount of at least 0.25 wt/wt %, beta hydroxyacids present in an amount of at least 0.1 wt/wt %, a chelating agent present in an amount of at least 0.1 wt/wt %, a (C1-C4)alkyl carboxylic acid present in an amount of at least 0.1 wt/wt %, a (C6-C12)aralkyl carboxylic acid present in an amount of at least 0.1 wt/wt %, a (C6-C12)alkaryl carboxylic acid present in an amount of at least 0.1 wt/wt %, or combinations thereof; with the proviso that the composition does not include parabens or phenoxyethanol;

wherein the effective amount of the antimicrobial component in the composition is at least 0.25% by weight;

wherein water is present in less than 10 wt-%, and wherein the fatty alcohol ester in the antimicrobial component is at least 70% pure.

* * * * *